United States Patent
Lee et al.

(10) Patent No.: US 10,059,949 B2
(45) Date of Patent: Aug. 28, 2018

(54) TREATMENT OF AGE-RELATED MACULAR DEGENERATION USING RNA COMPLEXES THAT TARGET MYD88 OR TLR3

(71) Applicant: OliX Pharmaceuticals, Inc., Seoul (KR)

(72) Inventors: Dong Ki Lee, Seoul (KR); Sun Woo Hong, Seoul (KR); Isu Hong, Seoul (KR); Jihye Hwang, Geonggi-Do (KR)

(73) Assignee: OliX Pharmaceuticals, Inc., Suwon-Si (KR)

( * ) Notice: Subject to any disclaimer, the term of this patent is extended or adjusted under 35 U.S.C. 154(b) by 0 days.

(21) Appl. No.: 15/352,322

(22) Filed: Nov. 15, 2016

(65) Prior Publication Data

US 2017/0137828 A1    May 18, 2017

Related U.S. Application Data

(60) Provisional application No. 62/255,878, filed on Nov. 16, 2015.

(51) Int. Cl.
*C12N 15/113* (2010.01)

(52) U.S. Cl.
CPC ........ *C12N 15/1138* (2013.01); *C12N 15/113* (2013.01); *C12N 2310/14* (2013.01); *C12N 2310/315* (2013.01); *C12N 2310/321* (2013.01); *C12N 2320/32* (2013.01)

(58) Field of Classification Search
None
See application file for complete search history.

(56) References Cited

U.S. PATENT DOCUMENTS

| | | |
|---|---|---|
| 2005/0282188 A1 | 12/2005 | Haeberli et al. |
| 2013/0035368 A1 | 2/2013 | Avkin-Nachum et al. |
| 2013/0190387 A1 * | 7/2013 | Feinstein .......... A61K 31/7088 514/44 A |

FOREIGN PATENT DOCUMENTS

| | | | |
|---|---|---|---|
| IL | WO2015015498 | * | 2/2015 |
| WO | WO-2009/105260 A2 | | 8/2009 |
| WO | WO-2012/078536 A2 | | 6/2012 |
| WO | WO-2014/043291 A1 | | 3/2014 |

OTHER PUBLICATIONS

Soutschek, et al. (2004) Therapeutic silencing of an endogenous gene by systemic administration of modified siRNAs. Nature, v. 432:173-8.*
Ambati et al., "Mechanisms of Age-Related Macular Degeneration," Neuron, 75: 26-39 (2012).
International Search Report and Written Opinion for International Application No. PCT/IB2016/001745 dated Mar. 24, 2017.
Patel et al., "A Novel Protective Role for the Innate Immunity Toll-Like Receptor 3 (TLR3) in the Retina via Stat3," Mol Cell Neurosci, 63: 38-48 (2014).

* cited by examiner

*Primary Examiner* — Jennifer Pitrak McDonald
(74) *Attorney, Agent, or Firm* — Foley Hoag LLP; David P. Halstead; Brendan T. Jones

(57) ABSTRACT

In certain aspects, provided herein are RNA complexes that inhibit Myeloid differentiation primary response gene 88 (MyD88) and/or Toll-like receptor 3 (TLR3) and are useful in the treatment of age-related macular degeneration (AMD). In certain aspects, provided herein are pharmaceutical compositions comprising such RNA complexes and methods of using such RNA complexes and pharmaceutical compositions.

20 Claims, 20 Drawing Sheets

Specification includes a Sequence Listing.

SEQUENCE LISTING

<160> NUMBER OF SEQ ID NOS: 414

<210> SEQ ID NO 1
<211> LENGTH: 2862
<212> TYPE: DNA

<213> ORGANISM: Homo sapiens

<400> SEQUENCE: 1

| | | | | | |
|---|---|---|---|---|---|
| agattcctac | ttcttacgcc | ccccacatca | cccgcctcga | gacctcaagg | gtagaggtgg | 60 |
| gcaccccgc | ctccgcactt | ttgctcgggg | ctccagattg | tagggcaggg | cggcgcttct | 120 |
| cggaaagcga | aagccggcgg | ggcggggcgg | gtgccgcagg | agaaagagga | agcgctggca | 180 |
| gacaatgcga | cccgaccgcg | ctgaggctcc | aggaccgccc | gccatggctg | caggaggtcc | 240 |
| cggcgcgggg | tctgcggccc | cggtctcctc | cacatcctcc | cttccctgg | ctgctctcaa | 300 |
| catgcgagtg | cggcgccgcc | tgtctctgtt | cttgaacgtg | cggacacagg | tggcggcga | 360 |
| ctggaccgcg | ctggcggagg | agatggactt | tgagtacttg | agatccggc | aactggagac | 420 |
| acaagcggac | cccactggca | ggctgctgga | cgcctggcag | ggacgccctg | cgcctctgt | 480 |
| aggccgactg | ctcgagctgc | ttaccaagct | gggccgcgac | gacgtgctgc | tggagctggg | 540 |
| acccagcatt | gaggaggatt | gccaaaagta | tatcttgaag | cagcagcagg | aggaggctga | 600 |
| gaagcccttta | caggtggccg | ctgtagacag | cagtgtccca | cggacagcag | agctggcggg | 660 |
| catcaccaca | cttgatgacc | ccctggggca | tatgcctgag | cgtttcgatg | ccttcatctg | 720 |
| ctattgcccc | agcgacatcc | agtttgtgca | ggagatgatc | cggcaactgg | aacagacaaa | 780 |
| ctatcgactg | aagttgtgtg | tgtctgaccg | cgatgtcctg | cctggcacct | gtgtctggtc | 840 |
| tattgctagt | gagctcatcg | aaaagaggtg | ccgccggatg | gtggtggttg | tctctgatga | 900 |
| ttacctgcag | agcaaggaat | gtgacttcca | gaccaaattt | gcactcagcc | tctctccagg | 960 |
| tgcccatcag | aagcgactga | tccccatcaa | gtacaaggca | atgaagaaag | agttccccag | 1020 |
| catcctgagg | ttcatcactg | tctgcgacta | caccaacccc | tgcaccaaat | cttggttctg | 1080 |
| gactcgcctt | gccaaggcct | tgtccctgcc | ctgaagactg | ttctgaggcc | ctgggtgtgt | 1140 |
| gtgtatctgt | ctgcctgtcc | atgtacttct | gccctgcctc | ctcctttcgt | tgtaggagga | 1200 |
| atctgtgctc | tacttacctc | tcaattcctg | gagatgccaa | cttcacagac | acgtctgcag | 1260 |
| cagctggaca | tcacatttca | tgtcctgcat | ggaaccagtg | gctgtgagtg | gcatgtccac | 1320 |
| ttgctggatt | atcagccagg | acactataga | acaggaccag | ctgagactaa | gaaggaccag | 1380 |
| cagagccagc | tcagctctga | gccattcaca | catcttcacc | ctcagtttcc | tcacttgagg | 1440 |
| agtgggatgg | ggagaacaga | gagtagctgt | gtttgaatcc | ctgtaggaaa | tggtgaagca | 1500 |
| tagctctggg | tctcctgggg | gagaccaggc | ttggctgcgg | gagagctggc | tgttgctgga | 1560 |
| ctacatgctg | gccactgctg | tgaccacgac | actgctgggg | cagcttcttc | cacagtgatg | 1620 |
| cctactgatg | cttcagtgcc | tctgcacacc | gcccattcca | cttcctcctt | ccccacaggg | 1680 |
| caggtggga | agcagtttgg | cccagcccaa | ggagacccca | ccttgagcct | tatttcctaa | 1740 |
| tgggtccacc | tctcatctgc | atctttcaca | cctcccagct | tctgcccaac | cttcagcagt | 1800 |
| gacaagtccc | caagagactc | gcctgagcag | cttgggctgc | ttttcatttc | cacctgtcag | 1860 |
| gatgcctgtg | gtcatgctct | cagctccacc | tggcatgaga | agggatcctg | gcctctggca | 1920 |
| tattcatcaa | gtatgagttc | tggggatgag | tcactgtaat | gatgtgagca | gggagccttc | 1980 |
| ctccctgggc | cacctgcaga | gagctttccc | accaactttg | taccttgatt | gccttacaaa | 2040 |
| gttatttgtt | tacaaacagc | gaccatataa | aagcctcctg | ccccaaagct | tgtgggcaca | 2100 |
| tgggcacata | cagactcaca | tacagacaca | cacatatatg | tacagacatg | tactctcaca | 2160 |
| cacacaggca | ccagcataca | cacgtttttc | taggtacagc | tcccaggaac | agctaggtgg | 2220 |
| gaaagtccca | tcactgaggg | agcctaacca | tgtccctgaa | caaaaattgg | gcactcatct | 2280 |

-continued

| | |
|---|---|
| attcctttc tcttgtgtcc ctactcattg aaaccaaact ctggaaagga cccaatgtac | 2340 |
| cagtatttat acctctaatg aagcacagag agaggaagag agctgcttaa actcacacaa | 2400 |
| caatgaactg cagacacagc tgttctctcc ctctctcctt cccagagcaa tttatacttt | 2460 |
| accctcaggc tgtcctctgg ggagaaggtg ccatggtctt aggtgtctgt gccccaggac | 2520 |
| agaccctagg accctaaatc aatagaaaa tgcatatctt tgctccactt tcagccaggc | 2580 |
| tggagcaagg taccttttct taggatcttg ggagggaatg gatgcccctc tctgcatgat | 2640 |
| cttgttgagg catttagctg ccatgcacct gtcccccttt aatactgggc attttaaagc | 2700 |
| catctcaaga ggcatcttct acatgttttg tacgcattaa aataatttca aagatatctg | 2760 |
| agaaaagccg atatttgcca ttcttcctat atcctggaat atatcttgca tcctgagttt | 2820 |
| ataataataa ataatattct accttggaaa aaaaaaaaaa aa | 2862 |

<210> SEQ ID NO 2
<211> LENGTH: 3057
<212> TYPE: DNA
<213> ORGANISM: Homo sapiens

<400> SEQUENCE: 2

| | |
|---|---|
| cactttcgag agtgccgtct atttgccaca cacttccctg atgaaatgtc tggatttgga | 60 |
| ctaaagaaaa aaggaaaggc tagcagtcat ccaacagaat catgagacag actttgcctt | 120 |
| gtatctactt ttggggggc cttttgccct ttgggatgct gtgtgcatcc tccaccacca | 180 |
| agtgcactgt tagccatgaa gttgctgact gcagccacct gaagttgact caggtacccg | 240 |
| atgatctacc cacaaacata acagtgttga accttaccca taatcaactc agaagattac | 300 |
| cagccgccaa cttcacaagg tatagccagc taactagctt ggatgtagga tttaacacca | 360 |
| tctcaaaact ggagccagaa ttgtgccaga aacttcccat gttaaaagtt ttgaacctcc | 420 |
| agcacaatga gctatctcaa cttctgata aaacctttgc cttctgcacg aatttgactg | 480 |
| aactccatct catgtccaac tcaatccaga aaattaaaaa taatccctt gtcaagcaga | 540 |
| agaattaat cacattagat ctgtctcata atggcttgtc atctacaaaa ttaggaactc | 600 |
| aggttcagct ggaaaatctc caagagcttc tattatcaaa caataaaatt caagcgctaa | 660 |
| aaagtgaaga actggatatc tttgccaatt catctttaaa aaaattagag ttgtcatcga | 720 |
| atcaaattaa agagttttct ccagggtgtt tcacgcaatt ggaagatta tttggcctct | 780 |
| ttctgaacaa tgtccagctg ggtcccagcc ttacagagaa gctatgtttg gaattagcaa | 840 |
| acacaagcat tcggaatctg tctctgagta acagccagct gtccaccacc agcaatacaa | 900 |
| ctttcttggg actaaagtgg acaaatctca ctatgctcga tctttcctac aacaacttaa | 960 |
| atgtggttgg taacgattcc tttgcttggc ttccacaact agaatatttc ttcctagagt | 1020 |
| ataataatat acagcatttg ttttctcact cttttgcacgg gcttttcaat gtgaggtacc | 1080 |
| tgaattgaa acggtctttt actaaacaaa gtatttccct tgcctcactc cccaagattg | 1140 |
| atgattttc ttttcagtgg ctaaaatgtt tggagcacct aacatggaa gataatgata | 1200 |
| ttccaggcat aaaaagcaat atgttcacag gattgataaa cctgaaatac ttaagtctat | 1260 |
| ccaactcctt tacaagtttg cgaactttga caaatgaaac atttgtatca cttgctcatt | 1320 |
| ctcccttaca catactcaac ctaaccaaga ataaaatctc aaaaatagag agtgatgctt | 1380 |
| tctcttggtt gggccaccta gaagtacttg acctgggcct taatgaaatt gggcaagaac | 1440 |
| tcacaggcca ggaatggaga ggtctagaaa atattttcga aatctatctt tcctacaaca | 1500 |

```
agtacctgca gctgactagg aactcctttg ccttggtccc aagccttcaa cgactgatgc    1560
tccgaagggt ggcccttaaa aatgtggata gctctccttc accattccag cctcttcgta    1620
acttgaccat tctggatcta agcaacaaca acatagccaa cataaatgat gacatgttgg    1680
agggtcttga gaaactagaa attctcgatt tgcagcataa caacttagca cggctctgga    1740
aacacgcaaa ccctggtggt cccatttatt tcctaaaggg tctgtctcac ctccacatcc    1800
ttaacttgga gtccaacggc tttgacgaga tcccagttga ggtcttcaag gatttatttg    1860
aactaaagat catcgattta ggattgaata atttaaacac acttccagca tctgtcttta    1920
ataatcaggt gtctctaaag tcattgaacc ttcagaagaa tctcataaca tccgttgaga    1980
agaaggtttt cgggccagct ttcaggaacc tgactgagtt agatatgcgc tttaatccct    2040
ttgattgcac gtgtgaaagt attgcctggt ttgttaattg gattaacgag acccatacca    2100
acatccctga gctgtcaagc cactaccttt gcaacactcc acctcactat catgggttcc    2160
cagtgagact ttttgataca tcatcttgca aagacagtgc cccctttgaa ctcttttttca    2220 tgatcaatac cagtatcctg ttgattttta tctttattgt acttctcatc cactttgagg    2280
gctggaggat atctttttat tggaatgttt cagtacatcg agttcttggt ttcaaagaaa    2340
tagacagaca gacagaacag tttgaatatg cagcatatat aattcatgcc tataaagata    2400
aggattgggt ctgggaacat ttctcttcaa tggaaaagga agaccaatct ctcaaatttt    2460
gtctggaaga aagggacttt gaggcgggtg ttttttgaact agaagcaatt gttaacagca    2520
tcaaaagaag cagaaaaatt attttttgtta taacacacca tctattaaaa gacccattat    2580
gcaaaagatt caaggtacat catgcagttc aacaagctat tgaacaaaat ctggattcca    2640
ttatattggt tttccttgag gagattccag attataaact gaaccatgca ctctgtttgc    2700
gaagaggaat gtttaaatct cactgcatct tgaactggcc agttcagaaa gaacggatag    2760
gtgcctttcg tcataaattg caagtagcac ttggatccaa aaactctgta cattaaattt    2820
atttaaatat tcaattagca aaggagaaac tttctcaatt taaaaagttc tatggcaaat    2880
ttaagttttc cataaaggtg ttataatttg tttattcata tttgtaaatg attatattct    2940
atcacaatta catctcttct aggaaaatgt gtctccttat ttcaggccta tttttgacaa    3000
ttgacttaat tttacccaaa ataaaacata taagcacgta aaaaaaaaaa aaaaaa       3057
```

<210> SEQ ID NO 3
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcggccgac uggacc                                                    16

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gguccagucg gccgccacc                                                 19

```
<210> SEQ ID NO 5
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uggcggccga cuggac                                                    16

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guccagucgg ccgccaccu                                                 19

<210> SEQ ID NO 7
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
guggcggccg acugga                                                    16

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uccagucggc cgccaccug                                                 19

<210> SEQ ID NO 9
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cuggcggagg agaugg                                                    16

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ccaucuccuc cgccagcgc                                                 19

<210> SEQ ID NO 11
```

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gcuggcggag gagaug                                                     16

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
caucuccucc gccagcgcg                                                  19

<210> SEQ ID NO 13
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
aguacuugga gauccg                                                     16

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
cggaucucca aguacucaa                                                  19

<210> SEQ ID NO 15
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gaguacuugg agaucc                                                     16

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ggaucuccaa guacucaaa                                                  19

<210> SEQ ID NO 17
<211> LENGTH: 16
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gccuuuacag guggcc                                                    16

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ggccaccugu aaaggcuuc                                                 19

<210> SEQ ID NO 19
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
agccuuuaca gguggc                                                    16

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gccaccugua aaggcuucu                                                 19

<210> SEQ ID NO 21
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
aagccuuuac aggugg                                                    16

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ccaccuguaa aggcuucuc                                                 19

<210> SEQ ID NO 23
<211> LENGTH: 16
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 23
gaagccuuua caggug                                                    16

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
caccuguaaa ggcuucuca                                                 19

<210> SEQ ID NO 25
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
agaagccuuu acaggu                                                    16

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
accuguaaag gcuucucag                                                 19

<210> SEQ ID NO 27
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
agaugauccg gcaacu                                                    16

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
aguugccgga ucaucuccu                                                 19

<210> SEQ ID NO 29
<211> LENGTH: 16
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 29
gagaugaucc ggcaac                                                      16

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
guugccggau caucuccug                                                   19

<210> SEQ ID NO 31
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ggagaugauc cggcaa                                                      16

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uugccggauc aucuccugc                                                   19

<210> SEQ ID NO 33
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
aggagaugau ccggca                                                      16

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ugccggauca ucuccugca                                                   19

<210> SEQ ID NO 35
<211> LENGTH: 16
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 35
caggagauga uccggc                                                        16

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
gccggaucau cuccugcac                                                     19

<210> SEQ ID NO 37
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
gcaggagaug auccgg                                                        16

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ccggaucauc uccugcaca                                                     19

<210> SEQ ID NO 39
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ugcaggagau gauccg                                                        16

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cggaucaucu ccugcacaa                                                     19

<210> SEQ ID NO 41
<211> LENGTH: 16
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 41
gugcaggaga ugaucc                                                          16

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ggaucaucuc cugcacaaa                                                       19

<210> SEQ ID NO 43
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ugugcaggag augauc                                                          16

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gaucaucucc ugcacaaac                                                       19

<210> SEQ ID NO 45
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
uugugcagga gaugau                                                          16

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
aucaucuccu gcacaaacu                                                       19

<210> SEQ ID NO 47
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uuugugcagg agauga                                                    16

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ucaucuccug cacaaacug                                                 19

<210> SEQ ID NO 49
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
guuugugcag gagaug                                                    16

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
caucuccugc acaaacugg                                                 19

<210> SEQ ID NO 51
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
aguuugugca ggagau                                                    16

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
aucuccugca caaacugga                                                 19

<210> SEQ ID NO 53
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 53
gugacuucca gaccaa                                                      16

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
uuggucugga agucacauu                                                   19

<210> SEQ ID NO 55
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ugugacuucc agacca                                                      16

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uggucuggaa gucacauuc                                                   19

<210> SEQ ID NO 57
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
augugacuuc cagacc                                                      16

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
ggucuggaag ucacauucc                                                   19

<210> SEQ ID NO 59
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
```

```
aaugugacuu ccagac                                           16
```

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60

```
gucuggaagu cacauuccu                                        19
```

<210> SEQ ID NO 61
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61

```
gaaugugacu uccaga                                           16
```

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62

```
ucuggaaguc acauuccuu                                        19
```

<210> SEQ ID NO 63
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63

```
ggaaugugac uuccag                                           16
```

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64

```
cuggaaguca cauuccuug                                        19
```

<210> SEQ ID NO 65
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
aggaauguga cuucca                                              16

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uggaagucac auccuugc                                            19

<210> SEQ ID NO 67
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
aaggaaugug acuucc                                              16

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
ggaagucaca uccuugcu                                            19

<210> SEQ ID NO 69
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
caaggaaugu gacuuc                                              16

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
gaagucacau uccuugcuc                                           19

<210> SEQ ID NO 71
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gcaaggaaug ugacuu                                              16

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
aagucacauu ccuugcucu                                           19

<210> SEQ ID NO 73
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
agcaaggaau gugacu                                              16

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
agucacauuc cuugcucug                                           19

<210> SEQ ID NO 75
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gagcaaggaa ugugac                                              16

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
gucacauucc uugcucugc                                           19

<210> SEQ ID NO 77
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
agagcaagga auguga                                              16

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ucacauuccu ugcucugca                                               19

<210> SEQ ID NO 79
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
cagagcaagg aaugug                                                  16

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cacauuccuu gcucugcag                                               19

<210> SEQ ID NO 81
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gucccugccc ugaaga                                                  16

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ucuucagggc agggacaag                                               19

<210> SEQ ID NO 83
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ugucccugcc cugaag                                                  16

```
<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
cuucagggca gggacaagg                                                      19

<210> SEQ ID NO 85
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uugucccugc ccugaa                                                         16

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
uucagggcag ggacaaggc                                                      19

<210> SEQ ID NO 87
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gcaccugugu cugguc                                                         16

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
gaccagacac aggugccag                                                      19

<210> SEQ ID NO 89
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ggcaccugug ucuggu                                                         16

<210> SEQ ID NO 90
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
accagacaca ggugccagg                                                      19

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gagtcaacgg atttggtcgt                                                     20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gacaagcttc ccgttctcag                                                     20

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
aagttatttg tttacaaaca gcgacca                                             27

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggaagaatgg caaatatcgg ct                                                  22

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
uuggucugga agucacauuc c                                                   21

<210> SEQ ID NO 96
<211> LENGTH: 31
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
uuggucugga agucacauuc cuugcucugc a                                31

<210> SEQ ID NO 97
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ugugacuucc agacca                                                 16

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
uggucuggaa gucacauucc u                                           21

<210> SEQ ID NO 99
<211> LENGTH: 31
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uggucuggaa gucacauucc uugcucugca g                                31

<210> SEQ ID NO 100
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
gugacuucca gaccaa                                                 16

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uuggucugga agucacauu                                              19

<210> SEQ ID NO 102
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 102
uuggucugga agucacauuc c                                               21

<210> SEQ ID NO 103
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
ugugacuucc agacca                                                     16

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
uggucuggaa gucacauuc                                                  19

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
uggucuggaa gucacauucc u                                               21

<210> SEQ ID NO 106
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
gugacuucca gaccaa                                                     16

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
uuggucugga agucacauuc c                                               21

<210> SEQ ID NO 108
<211> LENGTH: 16
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 108
gugacuucca gaccaa                                                        16

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
uuggucugga agucacauuc c                                                  21

<210> SEQ ID NO 110
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
gugacuucca gaccaa                                                        16

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
uuggucugga agucacauuc c                                                  21

<210> SEQ ID NO 112
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
gugacuucca gaccaa                                                        16

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uuggucugga agucacauuc c                                                  21

<210> SEQ ID NO 114
<211> LENGTH: 16
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 114
gugacuucca gaccaa                                                       16

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
uuggucugga agucacauuc c                                                 21

<210> SEQ ID NO 116
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gugacuucca gaccaa                                                       16

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
uuggucugga agucacauuc c                                                 21

<210> SEQ ID NO 118
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
gugacuucca gaccaa                                                       16

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uuggucugga agucacauuc c                                                 21

<210> SEQ ID NO 120
<211> LENGTH: 16
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 120
gugacuucca gaccaa                                                      16

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
uuggucugga agucacauuc c                                                21

<210> SEQ ID NO 122
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gugacuucca gaccaa                                                      16

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
uuggucugga agucacauuc c                                                21

<210> SEQ ID NO 124
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gugacuucca gaccaa                                                      16

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
uuggucugga agucacauuc c                                                21

<210> SEQ ID NO 126
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
ugugacuucc agacca                                                    16

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
uggucuggaa gucacauucc u                                              21

<210> SEQ ID NO 128
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ugugacuucc agacca                                                    16

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
uggucuggaa gucacauucc u                                              21

<210> SEQ ID NO 130
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ugugacuucc agacca                                                    16

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
uggucuggaa gucacauucc u                                              21

<210> SEQ ID NO 132
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ugugacuucc agacca                                                    16

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uggucuggaa gucacauucc u                                              21

<210> SEQ ID NO 134
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
ugugacuucc agacca                                                    16

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
uggucuggaa gucacauucc u                                              21

<210> SEQ ID NO 136
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ugugacuucc agacca                                                    16

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
uggucuggaa gucacauucc u                                              21

<210> SEQ ID NO 138
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138

```
ugugacuucc agacca                                            16

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
uggucuggaa gucacauucc u                                      21

<210> SEQ ID NO 140
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
ugugacuucc agacca                                            16

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
uggucuggaa gucacauucc u                                      21

<210> SEQ ID NO 142
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ugugacuucc agacca                                            16

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
uggucuggaa gucacauucc u                                      21

<210> SEQ ID NO 144
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
```
ugugacuucc agacca                                                        16

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uggucuggaa gucacauucc u                                                  21

<210> SEQ ID NO 146
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
gugacuucca gaccaa                                                        16

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
uuggucugga agucacauuc c                                                  21

<210> SEQ ID NO 148
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
gugacuucca gaccaa                                                        16

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
uuggucugga agucacauuc c                                                  21

<210> SEQ ID NO 150
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
gugacuucca gaccaa                                                        16

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
uuggucugga agucacauuc c                                              21

<210> SEQ ID NO 152
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gugacuucca gaccaa                                                    16

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
uuggucugga agucacauuc c                                              21

<210> SEQ ID NO 154
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gugacuucca gaccaa                                                    16

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
uuggucugga agucacauuc c                                              21

<210> SEQ ID NO 156
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
gugacuucca gaccaa                                                    16

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
uuggucugga agucacauuc c                                              21

<210> SEQ ID NO 158
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
gugacuucca gaccaa                                                    16

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
uuggucugga agucacauuc c                                              21

<210> SEQ ID NO 160
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
gugacuucca gaccaa                                                    16

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
uuggucugga agucacauuc c                                              21

<210> SEQ ID NO 162
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
ugugacuucc agacca                                                    16

```
<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
uggucuggaa gucacauucc u                                                  21

<210> SEQ ID NO 164
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
ugugacuucc agacca                                                        16

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
uggucuggaa gucacauucc u                                                  21

<210> SEQ ID NO 166
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ugugacuucc agacca                                                        16

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
uggucuggaa gucacauucc u                                                  21

<210> SEQ ID NO 168
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ugugacuucc agacca                                                        16

<210> SEQ ID NO 169
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
uggucuggaa gucacauucc u                                                  21

<210> SEQ ID NO 170
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
gugacuucca gaccaa                                                        16

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
uuggucugga agucacauuc c                                                  21

<210> SEQ ID NO 172
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
gugacuucca gaccaa                                                        16

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
uuggucugga agucacauu                                                     19

<210> SEQ ID NO 174
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
ugugacuucc agacca                                                        16

<210> SEQ ID NO 175
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uggucuggaa gucacauucc u                                              21

<210> SEQ ID NO 176
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
ugugacuucc agacca                                                    16

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uggucuggaa gucacauuc                                                 19

<210> SEQ ID NO 178
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
aucuuuccua caacaa                                                    16

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
uuguuguagg aaagaucgag c                                              21

<210> SEQ ID NO 180
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
ucuuuccuac aacaac                                                    16

<210> SEQ ID NO 181
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 181
guuguuguag gaaagaucga g                                              21

<210> SEQ ID NO 182
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
ggcccuuaaa aaugug                                                    16

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
cacauuuuua agggccaccc u                                              21

<210> SEQ ID NO 184
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
gcccuuaaaa augugg                                                    16

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
ccacauuuuu aagggccacc c                                              21

<210> SEQ ID NO 186
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
cccuuaaaaa ugugga                                                    16

<210> SEQ ID NO 187
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 187
uccacauuuu uaagggccac c                                              21

<210> SEQ ID NO 188
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
ccuuaaaaau guggau                                                    16

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
auccacauuu uuaagggcca c                                              21

<210> SEQ ID NO 190
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
cuuaaaaaug uggaua                                                    16

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
uauccacauu uuuaagggcc a                                              21

<210> SEQ ID NO 192
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
ucguaacuug accauu                                                    16

<210> SEQ ID NO 193
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 193
aauggucaag uuacgaagag g                                              21

<210> SEQ ID NO 194
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
cguaacuuga ccauuc                                                    16

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
gaauggucaa guuacgaaga g                                              21

<210> SEQ ID NO 196
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
guaacuugac cauucu                                                    16

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
agaaugguca aguuacgaag a                                              21

<210> SEQ ID NO 198
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
uaacuugacc auucug                                                    16

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 199
cagaaugguc aaguuacgaa g					21

<210> SEQ ID NO 200
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
aacuugacca uucugg					16

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
ccagaauggu caaguuacga a					21

<210> SEQ ID NO 202
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
acuugaccau ucugga					16

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
uccagaaugg ucaaguuacg a					21

<210> SEQ ID NO 204
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
aacaacaaca uagcca					16

<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 205
uggcuauguu guuguugcuu a                                              21

<210> SEQ ID NO 206
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
acaacaacau agccaa                                                    16

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
uuggcuaugu uguuguugcu u                                              21

<210> SEQ ID NO 208
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
caacaacaua gccaac                                                    16

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
guuggcuaug uuguuguugc u                                              21

<210> SEQ ID NO 210
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
aacaacauag ccaaca                                                    16

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 211
uguuggcuau guuguuguug c                                              21

<210> SEQ ID NO 212
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
acaacauagc caacau                                                    16

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
auguuggcua uguuguuguu g                                              21

<210> SEQ ID NO 214
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
caacauagcc aacaua                                                    16

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
uauguuggcu auguuguugu u                                              21

<210> SEQ ID NO 216
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
aacauagcca acauaa                                                    16

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
```
uuauguuggc uauguuguug u    21

<210> SEQ ID NO 218
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
acauagccaa cauaaa    16

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
uuuauguugg cuauguuguu g    21

<210> SEQ ID NO 220
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
auagccaaca uaaaug    16

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
cauuuauguu ggcuauguug u    21

<210> SEQ ID NO 222
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
uagccaacau aaauga    16

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
ucauuuaugu uggcuauguu g                                              21

<210> SEQ ID NO 224
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
aaucucucaa auuuug                                                    16

<210> SEQ ID NO 225
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
caaaauuuga gagauugguc u                                              21

<210> SEQ ID NO 226
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
ugcacucugu uugcga                                                    16

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
ucgcaaacag agugcauggu u                                              21

<210> SEQ ID NO 228
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
gcacucuguu ugcgaa                                                    16

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
uucgcaaaca gagugcaugg u                                              21

<210> SEQ ID NO 230
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
cacucuguuu gcgaag                                                     16

<210> SEQ ID NO 231
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
cuucgcaaac agagugcaug g                                               21

<210> SEQ ID NO 232
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
acucuguuug cgaaga                                                     16

<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ucuucgcaaa cagagugcau g                                               21

<210> SEQ ID NO 234
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
cucuguuugc gaagag                                                     16

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
cucuucgcaa acagagugca u                                               21

<210> SEQ ID NO 236
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
ucuguuugcg aagagg                                                   16

<210> SEQ ID NO 237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
ccucuucgca aacagagugc a                                             21

<210> SEQ ID NO 238
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
cuguuugcga agagga                                                   16

<210> SEQ ID NO 239
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
uccucuucgc aaacagagug c                                             21

<210> SEQ ID NO 240
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
uguuugcgaa gaggaa                                                   16

<210> SEQ ID NO 241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
uuccucuucg caaacagagu g                                             21

<210> SEQ ID NO 242
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 242
guuugcgaag aggaau                                           16

<210> SEQ ID NO 243
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 243
auuccucuuc gcaaacagag u                                     21

<210> SEQ ID NO 244
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 244
uuugcgaaga ggaaug                                           16

<210> SEQ ID NO 245
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 245
cauuccucuu cgcaaacaga g                                     21

<210> SEQ ID NO 246
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 246
uugcgaagag gaaugu                                           16

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 247
acauuccucu ucgcaaacag a                                     21

<210> SEQ ID NO 248

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
ugcgaagagg aauguu                                                    16

<210> SEQ ID NO 249
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
aacauuccuc uucgcaaaca g                                              21

<210> SEQ ID NO 250
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
gcgaagagga auguuu                                                    16

<210> SEQ ID NO 251
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
aaacauuccu cuucgcaaac a                                              21

<210> SEQ ID NO 252
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
cgaagaggaa uguuua                                                    16

<210> SEQ ID NO 253
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
uaaacauucc ucuucgcaaa c                                              21

<210> SEQ ID NO 254
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
gaagaggaau guuuaa                                                          16

<210> SEQ ID NO 255
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
uuaaacauuc cucuucgcaa a                                                    21

<210> SEQ ID NO 256
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
aagaggaaug uuuaaa                                                          16

<210> SEQ ID NO 257
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
uuuaaacauu ccucuucgca a                                                    21

<210> SEQ ID NO 258
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
agaggaaugu uuaaau                                                          16

<210> SEQ ID NO 259
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
auuuaaacau uccucuucgc a                                                    21

<210> SEQ ID NO 260
<211> LENGTH: 16
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 260
gaggaauguu uaaauc                                                    16

<210> SEQ ID NO 261
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
gauuuaaaca uuccucuucg c                                              21

<210> SEQ ID NO 262
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
aggaauguuu aaaucu                                                    16

<210> SEQ ID NO 263
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
agauuuaaac auuccucuuc g                                              21

<210> SEQ ID NO 264
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
ggaauguuua aaucuc                                                    16

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
gagauuuaaa cauuccucuu c                                              21

<210> SEQ ID NO 266
<211> LENGTH: 16
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 266
cuugaacugg ccaguu                                                        16

<210> SEQ ID NO 267
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
aacuggccag uucaagaugc a                                                  21

<210> SEQ ID NO 268
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
uugaacuggc caguuc                                                        16

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
gaacuggcca guucaagaug c                                                  21

<210> SEQ ID NO 270
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
ugaacuggcc aguuca                                                        16

<210> SEQ ID NO 271
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
ugaacuggcc aguucaagau g                                                  21

<210> SEQ ID NO 272
<211> LENGTH: 16
<212> TYPE: RNA
<213> ORGANISM: Artificial Sequence
<220> FEATURE:
```

<223> OTHER INFORMATION: Description of Artificial Sequence: Synthetic
oligonucleotide

<400> SEQUENCE: 272
gaacuggcca guucag                                                      16

<210> SEQ ID NO 273
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 273
cugaacuggc caguucaaga u                                                21

<210> SEQ ID NO 274
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 274
aacuggccag uucaga                                                      16

<210> SEQ ID NO 275
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 275
ucugaacugg ccaguucaag a                                                21

<210> SEQ ID NO 276
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 276
acuggccagu ucagaa                                                      16

<210> SEQ ID NO 277
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 277
uucugaacug gccaguucaa g                                                21

<210> SEQ ID NO 278
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 278
cuggccaguu cagaaa                                                  16

<210> SEQ ID NO 279
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
uuucugaacu ggccaguuca a                                            21

<210> SEQ ID NO 280
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
uggccaguuc agaaag                                                  16

<210> SEQ ID NO 281
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
cuuucugaac uggccaguuc a                                            21

<210> SEQ ID NO 282
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
ggccaguuca gaaaga                                                  16

<210> SEQ ID NO 283
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
ucuuucugaa cuggccaguu c                                            21

<210> SEQ ID NO 284
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
gccaguucag aaagaa                                                         16

<210> SEQ ID NO 285
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
uucuuucuga acuggccagu u                                                   21

<210> SEQ ID NO 286
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ccaguucaga aagaac                                                         16

<210> SEQ ID NO 287
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
guucuuucug aacuggccag u                                                   21

<210> SEQ ID NO 288
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
caguucagaa agaacg                                                         16

<210> SEQ ID NO 289
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
cguucuuucu gaacuggcca g                                                   21

<210> SEQ ID NO 290
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 290
aguucagaaa gaacgg                                                   16

<210> SEQ ID NO 291
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
ccguucuuuc ugaacuggcc a                                             21

<210> SEQ ID NO 292
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
guucagaaag aacgga                                                   16

<210> SEQ ID NO 293
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
uccguucuuu cugaacuggc c                                             21

<210> SEQ ID NO 294
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
uucagaaaga acggau                                                   16

<210> SEQ ID NO 295
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
auccguucuu ucugaacugg c                                             21

<210> SEQ ID NO 296
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
```
ucagaaagaa cggaua                                             16

<210> SEQ ID NO 297
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
uauccguucu uucugaacug g                                       21

<210> SEQ ID NO 298
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
aauugcaagu agcacu                                             16

<210> SEQ ID NO 299
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
agugcuacuu gcaauuuaug a                                       21

<210> SEQ ID NO 300
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
auugcaagua gcacuu                                             16

<210> SEQ ID NO 301
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
aagugcuacu ugcaauuuau g                                       21

<210> SEQ ID NO 302
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
uugcaaguag cacuug                                                     16

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
caagugcuac uugcaauuua u                                               21

<210> SEQ ID NO 304
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ugcaaguagc acuugg                                                     16

<210> SEQ ID NO 305
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
ccaagugcua cuugcaauuu a                                               21

<210> SEQ ID NO 306
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
gcaaguagca cuugga                                                     16

<210> SEQ ID NO 307
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
uccaagugcu acuugcaauu u                                               21

<210> SEQ ID NO 308
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
caaguagcac uuggau                                                     16

<210> SEQ ID NO 309
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
auccaagugc uacuugcaau u                                              21

<210> SEQ ID NO 310
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
aaguagcacu uggauc                                                    16

<210> SEQ ID NO 311
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
gauccaagug cuacuugcaa u                                              21

<210> SEQ ID NO 312
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
ugcccccuuu gaacuc                                                    16

<210> SEQ ID NO 313
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
gaguucaaag ggggcacugu c                                              21

<210> SEQ ID NO 314
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
ucugggaaca uuucuc                                                    16

<210> SEQ ID NO 315
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
gagaaauguu cccagaccca a                                            21

<210> SEQ ID NO 316
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
cagcaucaaa agaagc                                                  16

<210> SEQ ID NO 317
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
gcuucuuuug augcuguuaa c                                            21

<210> SEQ ID NO 318
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
cacgugugaa aguauu                                                  16

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
aauacuuuca cacgugcaau c                                            21

<210> SEQ ID NO 320
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
gucucaccuc cacauc                                                  16

```
<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
gauguggagg ugagacagac c                                              21

<210> SEQ ID NO 322
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
ugucucaccu ccacau                                                    16

<210> SEQ ID NO 323
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
auguggaggu gagacagacc c                                              21

<210> SEQ ID NO 324
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
agauucaagg uacauc                                                    16

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
gauguaccuu gaaucuuuug c                                              21

<210> SEQ ID NO 326
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
ggaaacacgc aaaccc                                                    16

<210> SEQ ID NO 327
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
ggguuugcgu guuccagag c                                              21

<210> SEQ ID NO 328
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
uggaaacacg caaacc                                                   16

<210> SEQ ID NO 329
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
gguuugcgug uuccagagc c                                              21

<210> SEQ ID NO 330
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
uugagaaacu agaaau                                                   16

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
auuucuaguu ucucaagacc c                                             21

<210> SEQ ID NO 332
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
cuugagaaac uagaaa                                                   16

<210> SEQ ID NO 333
<211> LENGTH: 21
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
uuucuaguuu cucaagaccc u                                              21

<210> SEQ ID NO 334
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
aacauccguu gagaag                                                    16

<210> SEQ ID NO 335
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
cuucucaacg gauguuauga g                                              21

<210> SEQ ID NO 336
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
gugcccccuu ugaacu                                                    16

<210> SEQ ID NO 337
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
aguucaaagg gggcacuguc u                                              21

<210> SEQ ID NO 338
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338 agugccccu uugaac                                                     16

<210> SEQ ID NO 339
<211> LENGTH: 21
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 339
guucaaaggg ggcacugucu u                                             21

<210> SEQ ID NO 340
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
cagugccccc uuugaa                                                   16

<210> SEQ ID NO 341
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
uucaaagggg gcacugucuu u                                             21

<210> SEQ ID NO 342
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
ggaggauauc uuuuua                                                   16

<210> SEQ ID NO 343
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
uaaaaagaua uccuccagcc c                                             21

<210> SEQ ID NO 344
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
uggaggauau cuuuuu                                                   16

<210> SEQ ID NO 345
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 345
aaaaagauau ccuccagccc u                                              21

<210> SEQ ID NO 346
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
acugaaccau gcacuc                                                    16

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
gagugcaugg uucaguuuau a                                              21

<210> SEQ ID NO 348
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
ugaaccaugc acucug                                                    16

<210> SEQ ID NO 349
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
cagagugcau gguucaguuu a                                              21

<210> SEQ ID NO 350
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
gaaccaugca cucugu                                                    16

<210> SEQ ID NO 351
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 351
acagagugca ugguucaguu u                                          21

<210> SEQ ID NO 352
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
aaccaugcac ucuguu                                                16

<210> SEQ ID NO 353
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
aacagagugc augguucagu u                                          21

<210> SEQ ID NO 354
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
accaugcacu cuguuu                                                16

<210> SEQ ID NO 355
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
aaacagagug caugguucag u                                          21

<210> SEQ ID NO 356
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
ccaugcacuc uguuug                                                16

<210> SEQ ID NO 357
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 357
caaacagagu gcaugguuca g                                              21

<210> SEQ ID NO 358
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
caugcacucu guuugc                                                    16

<210> SEQ ID NO 359
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
gcaaacagag ugcaugguuc a                                              21

<210> SEQ ID NO 360
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
cugcaucuug aacugg                                                    16

<210> SEQ ID NO 361
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
ccaguucaag augcagugag a                                              21

<210> SEQ ID NO 362
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
acugcaucuu gaacug                                                    16

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 363
caguucaaga ugcagugaga u                                              21

<210> SEQ ID NO 364
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
cacugcaucu ugaacu                                                    16

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
aguucaagau gcagugagau u                                              21

<210> SEQ ID NO 366
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
ucacugcauc uugaac                                                    16

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
guucaagaug cagugagauu u                                              21

<210> SEQ ID NO 368
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
uaaauugcaa guagca                                                    16

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
ugcuacuugc aauuuaugac g                                              21

<210> SEQ ID NO 370
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
auaaauugca aguagc                                                    16

<210> SEQ ID NO 371
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
gcuacuugca auuuaugacg a                                              21

<210> SEQ ID NO 372
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
cgucauaaau ugcaag                                                    16

<210> SEQ ID NO 373
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
cuugcaauuu augacgaaag g                                              21

<210> SEQ ID NO 374
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
ucgucauaaa uugcaa                                                    16

<210> SEQ ID NO 375
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375

-continued

```
uugcaauuua ugacgaaagg c                                            21

<210> SEQ ID NO 376
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
uucgucauaa auugca                                                  16

<210> SEQ ID NO 377
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
ugcaauuuau gacgaaaggc a                                            21

<210> SEQ ID NO 378
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
ugcacucugu uugcga                                                  16

<210> SEQ ID NO 379
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
ucgcaaacag agugcauggu u                                            21

<210> SEQ ID NO 380
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
ucgcaaacag agugcauggu u                                            21

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
```
ucgcaaacag agugcauggu u                                              21

<210> SEQ ID NO 382
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
acucuguuug cgaaga                                                    16

<210> SEQ ID NO 383
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
ucuucgcaaa cagagugcau g                                              21

<210> SEQ ID NO 384
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
ucuucgcaaa cagagugcau g                                              21

<210> SEQ ID NO 385
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
ucuucgcaaa cagagugcau g                                              21

<210> SEQ ID NO 386
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
uguuugcgaa gaggaa                                                    16

<210> SEQ ID NO 387
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387 uucccucuucg caaacagagu g                                             21

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
uuccucuucg caaacagagu g                                              21

<210> SEQ ID NO 389
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
uuccucuucg caaacagagu g                                              21

<210> SEQ ID NO 390
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
guuugcgaag aggaau                                                    16

<210> SEQ ID NO 391
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
auuccucuuc gcaaacagag u                                              21

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
auuccucuuc gcaaacagag u                                              21

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
auuccucuuc gcaaacagag u                                              21

<210> SEQ ID NO 394
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
gaagaggaau guuuaa                                                       16

<210> SEQ ID NO 395
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
uuaaacauuc cucuucgcaa a                                                 21

<210> SEQ ID NO 396
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
uuaaacauuc cucuucgcaa a                                                 21

<210> SEQ ID NO 397
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
uuaaacauuc cucuucgcaa a                                                 21

<210> SEQ ID NO 398
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
ggccaguuca gaaaga                                                       16

<210> SEQ ID NO 399
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
ucuuucugaa cuggccaguu c                                                 21

```
<210> SEQ ID NO 400
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
ucuuucugaa cuggccaguu c                                              21

<210> SEQ ID NO 401
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
ucuuucugaa cuggccaguu c                                              21

<210> SEQ ID NO 402
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
guucagaaag aacgga                                                    16

<210> SEQ ID NO 403
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
uccguucuuu cugaacuggc c                                              21

<210> SEQ ID NO 404
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
uccguucuuu cugaacuggc c                                              21

<210> SEQ ID NO 405
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
uccguucuuu cugaacuggc c                                              21

<210> SEQ ID NO 406
```

```
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
ucagaaagaa cggaua                                                        16

<210> SEQ ID NO 407
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
uauccguucu uucugaacug g                                                  21

<210> SEQ ID NO 408
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
uauccguucu uucugaacug g                                                  21

<210> SEQ ID NO 409
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
uauccguucu uucugaacug g                                                  21

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410
tgcccccttt gaactctttt                                                    20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411
aaaaacaccc gcctcaaagt                                                    20

<210> SEQ ID NO 412
<211> LENGTH: 16
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
gaagaggaau guuuaa                                                          16

<210> SEQ ID NO 413
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
uuaaacauuc cucuucgca                                                       19

<210> SEQ ID NO 414
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
uuaaacauuc cucuucgcaa a                                                    21
```

TREATMENT OF AGE-RELATED MACULAR DEGENERATION USING RNA COMPLEXES THAT TARGET MYD88 OR TLR3

RELATED APPLICATIONS

This application claims the benefit of priority to U.S. Provisional Patent Application Ser. No. 62/255,878, filed Nov. 16, 2015, which is hereby incorporated by reference in its entirety.

SEQUENCE LISTING

The instant application contains a Sequence Listing which has been filed electronically in ASCII format and is hereby incorporated by reference in its entirety. Said ASCII copy, created on Jul. 27, 2017, is named OPH-00601(32896-00601)_SL.txt and is 105,629 bytes in size.

BACKGROUND

Age-related macular degeneration (AMD) is a disease that results from the degeneration of the retinal pigmented epithelium lining in the eye's macula, which leads to vision loss. The macula is a small area in the retina made up of the light-sensitive tissues lining the back of the eye and plays a critical role in central vision. AMD is one of the leading causes of blindness worldwide.

AMD occurs in "wet" and "dry" forms. Wet AMD is the result of abnormal blood vessel growth in the retina. In wet AMD, increased amount of vascular endothelial growth factor (VEGF) contributes to this neovascularization, so therapeutic options include the use of VEGF inhibitors are used. However, many patients treated with VEGF inhibitors develop geographic atrophy (GA), which is a primary symptom of late dry macular degeneration, within a few years of treatment. The disease pathogenesis of dry AMD is unclear and no medical treatment is currently available for dry AMD. Therefore, the development of therapeutics that can treat both wet and dry macular degeneration needed.

SUMMARY

MyD88 and TLR3 play important roles in the onset of both dry AMD and wet AMD. Unlike VEGF antibodies, which are ineffective at treating dry macular degeneration, a therapeutic agent targeting MyD88 or TLR3 can be used to treat both wet and dry macular degeneration.

In certain aspects, provided herein are RNA complexes that inhibit Myeloid differentiation primary response gene 88 (MyD88) and/or Toll-like receptor 3 (TLR3) and are useful in the treatment of age-related macular degeneration (AMD) (e.g., wet and/or dry AMD). In certain aspects, provided herein are pharmaceutical compositions comprising such RNA complexes and methods of using such RNA complexes and pharmaceutical compositions.

In certain aspects, provided herein is an RNA complex comprising an antisense strand having sequence complementarity to a MyD88 mRNA sequence (e.g., a human MyD88 mRNA sequence) and a sense strand having sequence complementarity to the antisense strand. In some embodiments, the RNA complex is capable of inhibiting MyD88 expression by a cell. In certain embodiments, the RNA complex is capable of inhibiting MyD88 production by a cell. In some embodiments, the RNA complex is an asymmetric short interfering RNA (an asiRNA). In some embodiments, the RNA complex is a long asymmetric short interfering RNA (a lasiRNA).

In some embodiments, the antisense strand is at least 19 nucleotides (nt) in length. In some such embodiments, the antisense strand is 19 to 21 nt in length (i.e., 19, 20 or 21 nt in length). In other such embodiments, the antisense strand is at least 24 nt in length (e.g., 24 to 121 nt in length), e.g., 31 nt in length. In certain embodiments, at least 13, 14, 15, 16, 17, 18, 19, 20 or 21 nt of the antisense strand are complementary to the MyD88 mRNA sequence. In some embodiments, the sense strand is 15 to 17 nt in length (i.e., 15 nt in length, 16 nt in length or 17 nt in length). In certain embodiments, at least 15 nt, at least 16 nt or at least 17 nt of the sense strand are complementary to the sequence of the antisense strand. Representative RNA complexes include the RNA complexes listed in Table 1, Table 2, Table 3, Table 4, Table 5 or Table 6.

In certain aspects, provided herein is an RNA complex comprising an antisense strand having sequence complementarity to a TLR3 mRNA sequence (e.g., a human TLR3 mRNA sequence) and a sense strand having sequence complementarity to the antisense strand. In some embodiments, the RNA complex is capable of inhibiting TLR3 expression by a cell. In certain embodiments, the RNA complex is capable of inhibiting TLR3 production by a cell. In some embodiments, the RNA complex is an asymmetric short interfering RNA (an asiRNA). In some embodiments, the RNA complex is a long asymmetric short interfering RNA (a lasiRNA).

In some embodiments, the antisense strand is at least 19 nucleotides (nt) in length. In some such embodiments, the antisense strand is 19 to 21 nt in length (i.e., 19, 20 or 21 nt in length). In other such embodiments, the antisense strand is at least 24 nt in length (e.g., 24 to 121 nt in length). In certain embodiments, at least 13, 14, 15, 16, 17, 18, 19, 20 or 21 nt of the antisense strand are complementary to the TLR3 mRNA sequence. In some embodiments, the sense strand is 15 to 17 nt in length (i.e., 15 nt in length, 16 nt in length or 17 nt in length). In certain embodiments, at least 15 nt, at least 16 nt or at least 17 nt of the sense strand are complementary to the sequence of the antisense strand. Representative RNA complexes include the RNA complexes listed in Table 7, Table 8 or Table 10.

In some embodiments, the RNA complex provided herein comprises a chemical modification, wherein the modification facilitates the penetration of a cellular membrane in the absence of a delivery vehicle. In some embodiments, the modification is a 2'-O-methylated nucleoside, a phosphorothioate bond and/or a cholesterol moiety. In some such embodiments, the 2'-O-methyl nucleoside is positioned at the 3' terminus of the sense strand. In some such embodiments, the 3' terminal region of the sense strand comprises a plurality of 2'-O-methylated nucleosides (e.g., 2, 3, 4, 5 or 6 2'-O-methylated nucleosides within 6 nucleosides of the 3' terminus). In other embodiments, the 2'-O-methyl nucleoside is positioned at the 3' terminus of the antisense strand. In some such embodiments, 3' terminal region of the antisense strand comprises a plurality of 2'-O-methylated nucleosides (e.g., 2, 3, 4, 5 or 6 2'-O-methylated nucleosides within 6 nucleosides of the 3' terminus). In some embodiments, both the 3' terminal region of the sense strand and the 3' terminal region of the antisense strand comprise a plurality of 2'-O-methylated nucleosides. Representative RNA complexes include the modified RNA complexes listed in Table 3, Table 4, Table 5, Table 6, Table 8 or Table 10. In certain embodiments, the RNA complex is not cytotoxic.

In some embodiments, the RNA complex provided herein comprises a phosphorothioate bond. In some embodiments, at least 25%, 30%, 35%, 40%, 45%, 50%, 55%, 60%, 65%, 70%, 75%, 80%, 85%, 90% or 95% of the bonds between the ribonucleotides in the sense strand of the RNA complex are phosphorothioate bonds. In some such embodiments, all of the bonds between the ribonucleotides in the sense strand of the RNA complex are phosphorothioate bonds. Similarly, in some embodiments, at least 25%, 30%, 35%, 40%, 45%, 50%, 55%, 60%, 65%, 70%, 75%, 80%, 85%, 90% or 95% of the bonds between the ribonucleotides in the antisense strand of the RNA complex are phosphorothioate bonds. In some such embodiments, all of the bonds between the ribonucleotides in the antisense strand of the RNA complex are phosphorothioate bonds.

In some embodiments, the RNA complex provided herein comprises a cholesterol moiety. In some embodiments, the cholesterol moiety is attached to the 3' terminus of the sense strand.

In certain aspects, provided herein is a pharmaceutical composition comprising an RNA complex provided herein and a pharmaceutically acceptable carrier. In certain embodiments, the pharmaceutical composition is formulated for administration to the eye (e.g., as an eye drop). In some embodiments, the pharmaceutical composition is formulated for intravitreal delivery.

In certain aspects, provided herein is a method of inhibiting MyD88 and/or TLR3 expression by a cell comprising contacting the cell with an RNA complex and/or a pharmaceutical composition provided herein. In some embodiments, the cell is present in the eye of a human subject (e.g., a human subject with wet or dry AMD). In certain aspects, provided herein is a method of treating a human subject for AMD (e.g., wet AMD and/or dry AMD) comprising administering to the subject, e.g., to the eye, an RNA complex and/or pharmaceutical composition provided herein. In some embodiments, the RNA complex and/or a pharmaceutical composition is administered to the eye by intravitreal injection.

DETAILED DESCRIPTION

General

Figure 1:
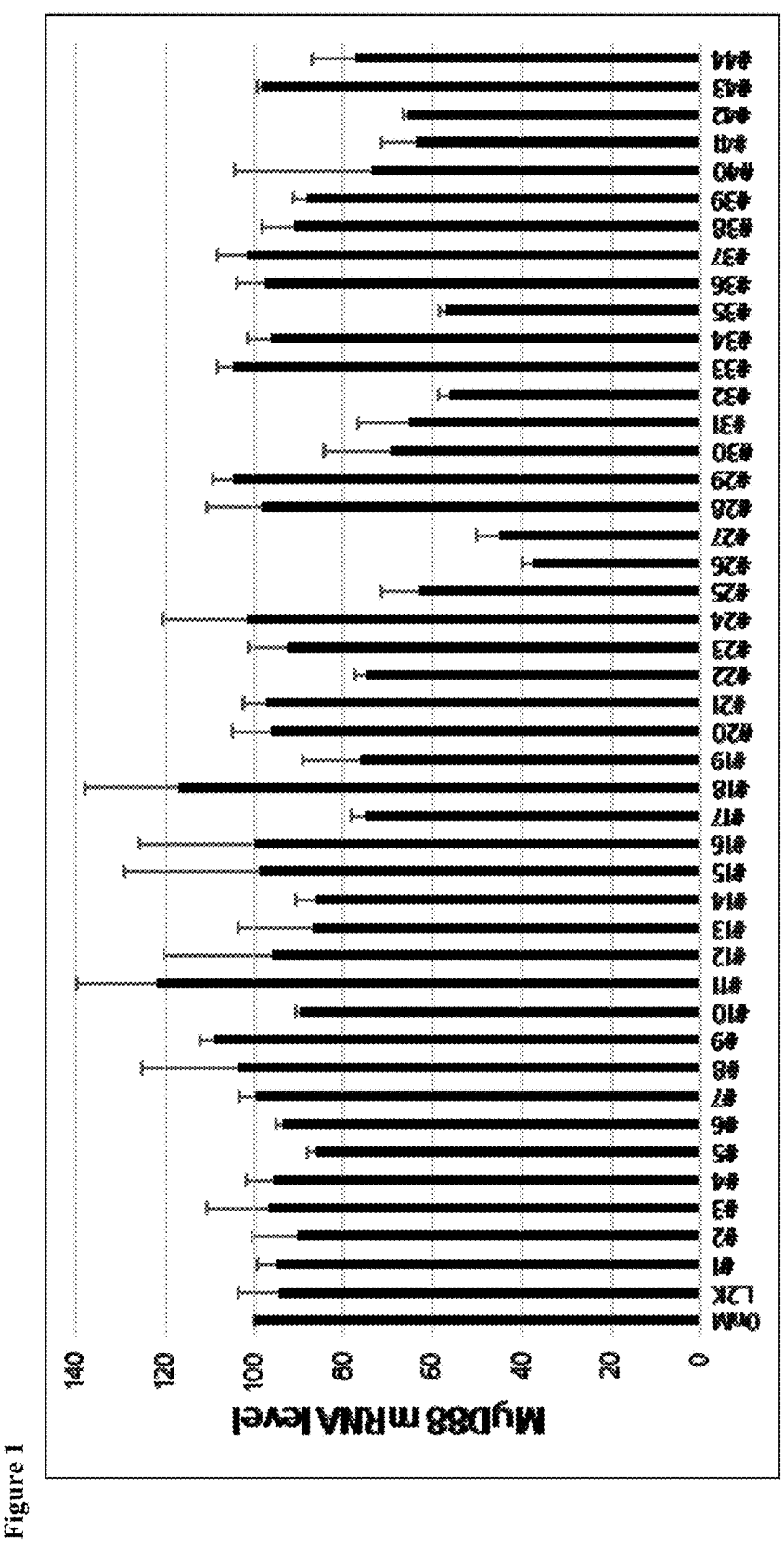
FIG. 1 shows the gene silencing efficiency of exemplary asiRNAs that target MyD88. The asiRNAs were transfected into HeLa cells at a concentration of 0.3 nM, and, after 24 hours, the degree of MyD88 mRNA expression was determined using real-time PCR. The mean and standard deviation of three repeat experiments are depicted.

In certain aspects, provided herein are asymmetric RNA complexes (e.g., asiRNAs or lasiRNAs) that inhibit MyD88 and/or TLR3 expression and are therefore useful for the treatment of AMD (e.g., wet AMD and/or dry AMD). In some embodiments, the RNA complexes are chemically modified to be capable of penetrating a cell without need for a transfection vehicle. In some embodiments, the RNA complex is an RNA complex listed in Table 1, Table 2, Table 3, Table 4, Table 5, Table 6, Table 8 or Table 10. In certain aspects, provided herein are pharmaceutical compositions comprising such RNA complexes and methods of using such RNA complexes and pharmaceutical compositions.

MyD88 is a protein that plays an important role in the onset of both dry AMD and wet AMD as one of the proteins that activate the immune response. Unlike previous AMD therapies that target VEGF, which are ineffective at treating dry macular degeneration, therapies targeting MyD88 can be used to treat both wet and dry AMD. An exemplary human MyD88 cDNA sequence is provided below.

Human MyD88 cDNA Sequence.

(SEQ ID NO: 1)

```
   1 agattcctac ttcttacgcc ccccacatca cccgcctcga gacctcaagg gtagaggtgg
  61 gcacccccgc ctccgcactt ttgctcgggg ctccagattg tagggcaggg cggcgcttct
 121 cggaaagcga aagccggcgg ggcggggcgg gtgccgcagg agaaagagga agcgctggca
 181 gacaatgcga cccgaccgcg ctgaggctcc aggaccgccc gccatggctg caggaggtcc
 241 cggcgcgggg tctgcggccc cggtctcctc cacatcctcc cttcccctgg ctgctctcaa
 301 catgcgagtg cggcgccgcc tgtctctgtt cttgaacgtg cggacacagg tggcggccga
 361 ctggaccgcg ctggcggagg agatggactt tgagtacttg gagatccggc aactggagac
 421 acaagcggac cccactggca ggctgctgga cgcctggcag ggacgccctg gcgcctctgt
 481 aggccgactg ctcgagctgc ttaccaagct gggccgcgac gacgtgctgc tggagctggg
 541 acccagcatt gaggaggatt gccaaaagta tatcttgaag cagcagcagg aggaggctga
 601 gaagccttta caggtggccg ctgtagacag cagtgtccca cggacagcag agctggcggg
 661 catcaccaca cttgatgacc ccctggggca tatgcctgag cgtttcgatg ccttcatctg
 721 ctattgcccc agcgacatcc agtttgtgca ggagatgatc cggcaactgg aacagacaaa
 781 ctatcgactg aagttgtgtg tgtctgaccg cgatgtcctg cctggcacct gtgtctggtc
 841 tattgctagt gagctcatcg aaaagaggtg ccgccggatg gtggtggttg tctctgatga
 901 ttacctgcag agcaaggaat gtgacttcca gaccaaattt gcactcagcc tctctccagg
 961 tgcccatcag aagcgactga tccccatcaa gtacaaggca atgaagaaag agttccccag
1021 catcctgagg ttcatcactg tctgcgacta caccaacccc tgcaccaaat cttggttctg
1081 gactcgcctt gccaaggcct tgtccctgcc ctgaagactg ttctgaggcc ctgggtgtgt
1141 gtgtatctgt ctgcctgtcc atgtacttct gccctgcctc ctcctttcgt tgtaggagga
1201 atctgtgctc tacttacctc tcaattcctg gagatgccaa cttcacagac acgtctgcag
```

-continued

```
1261 cagctggaca tcacatttca tgtcctgcat ggaaccagtg gctgtgagtg gcatgtccac 1321 ttgctggatt atcagccagg acactataga acaggaccag ctgagactaa gaaggaccag 1381 cagagccagc tcagctctga gccattcaca catcttcacc ctcagtttcc tcacttgagg 1441 agtgggatgg ggagaacaga gagtagctgt gtttgaatcc ctgtaggaaa tggtgaagca 1501 tagctctggg tctcctgggg gagaccaggc ttggctgcgg gagagctggc tgttgctgga 1561 ctacatgctg gccactgctg tgaccacgac actgctgggg cagcttcttc cacagtgatg 1621 cctactgatg cttcagtgcc tctgcacacc gcccattcca cttcctcctt ccccacaggg 1681 caggtgggga agcagtttgg cccagcccaa ggagacccca ccttgagcct tatttcctaa 1741 tgggtccacc tctcatctgc atctttcaca cctcccagct tctgcccaac cttcagcagt 1801 gacaagtccc caagagactc gcctgagcag cttgggctgc ttttcatttc cacctgtcag 1861 gatgcctgtg gtcatgctct cagctccacc tggcatgaga agggatcctg gcctctggca 1921 tattcatcaa gtatgagttc tggggatgag tcactgtaat gatgtgagca gggagccttc 1981 ctccctgggc cacctgcaga gagctttccc accaactttg taccttgatt gccttacaaa 2041 gttatttgtt tacaaacagc gaccatataa aagcctcctg ccccaaagct tgtgggcaca 2101 tgggcacata cagactcaca tacagacaca cacatatatg tacagacatg tactctcaca 2161 cacacaggca ccagcataca cacgtttttc taggtacagc tcccaggaac agctaggtgg 2221 gaaagtccca tcactgaggg agcctaacca tgtccctgaa caaaaattgg gcactcatct 2281 attccttttc tcttgtgtcc ctactcattg aaaccaaact ctggaaagga cccaatgtac 2341 cagtatttat acctctaatg aagcacagag agaggaagag agctgcttaa actcacacaa 2401 caatgaactg cagacacagc tgttctctcc ctctctcctt cccagagcaa tttatacttt 2461 accctcaggc tgtcctctgg ggagaaggtg ccatggtctt aggtgtctgt gccccaggac 2521 agaccctagg accctaaatc caatagaaaa tgcatatctt tgctccactt tcagccaggc 2581 tggagcaagg taccttttct taggatcttg ggagggaatg gatgcccctc tctgcatgat 2641 cttgttgagg catttagctg ccatgcacct gtccccttt aatactgggc attttaaagc 2701 catctcaaga ggcatcttct acatgttttg tacgcattaa aataatttca aagatatctg 2761 agaaaagccg atatttgcca ttcttcctat atcctggaat atatcttgca tcctgagttt 2821 ataataataa ataatattct accttggaaa aaaaaaaaa aa
```

Toll-like receptor 3 (TLR3) plays a pivotal role in innate immune system as a type 1 transmembrane signaling molecule. TLR3 ligands include double-stranded RNA formed by the proliferation of RNA virus and polyinosinic-polycytidylic (polyI:C), a dsRNA analogue. In individuals suffering from dry AMD, alu-RNAs, a type of dsRNA, accumulate in retinal epithelial cells. Compared to a healthy individuals, people suffering from wet AMD had high expression of levels of TLR3 in peripheral blood mononuclear cells, indicating that TLR3 is closely associated in the pathogenesis of both dry and wet AMD. An exemplary human MyD88 cDNA sequence is provided below.

Human TLR3 cDNA Sequence.

(SEQ ID NO: 2)
```
  1 cactttcgag agtgccgtct atttgccaca cacttccctg atgaaatgtc tggatttgga 61 ctaaagaaaa aaggaaaggc tagcagtcat ccaacagaat catgagacag actttgcctt 121 gtatctactt tgggggggc cttttgccct tgggatgct gtgtgcatcc tccaccacca 181 agtgcactgt tagccatgaa gttgctgact gcagccacct gaagttgact caggtacccg 241 atgatctacc cacaaacata acagtgttga accttaccca taatcaactc agaagattac 301 cagccgccaa cttcacaagg tatagccagc taactagctt ggatgtagga tttaacacca 361 tctcaaaact ggagccagaa ttgtgccaga aacttcccat gttaaaagtt ttgaacctcc
```

-continued

```
 421 agcacaatga gctatctcaa ctttctgata aaaccttttgc cttctgcacg aatttgactg 481 aactccatct catgtccaac tcaatccaga aaattaaaaa taatcccttt gtcaagcaga 541 agaatttaat cacattagat ctgtctcata atggcttgtc atctacaaaa ttaggaactc 601 aggttcagct ggaaaatctc caagagcttc tattatcaaa caataaaatt caagcgctaa 661 aaagtgaaga actggatatc tttgccaatt catctttaaa aaaattagag ttgtcatcga 721 atcaaattaa agagttttct ccagggtgtt ttcacgcaat tggaagatta tttggcctct 781 ttctgaacaa tgtccagctg ggtcccagcc ttacagagaa gctatgtttg gaattagcaa 841 acacaagcat tcggaatctg tctctgagta acagccagct gtccaccacc agcaatacaa 901 ctttcttggg actaaagtgg acaaatctca ctatgctcga tctttcctac aacaacttaa 961 atgtggttgg taacgattcc tttgcttggc ttccacaact agaatatttc ttcctagagt 1021 ataataatat acagcatttg ttttctcact ctttgcacgg gcttttcaat gtgaggtacc 1081 tgaatttgaa acggtctttt actaaacaaa gtatttccct tgcctcactc cccaagattg 1141 atgattttc ttttcagtgg ctaaaatgtt tggagcacct taacatggaa gataatgata 1201 ttccaggcat aaaaagcaat atgttcacag gattgataaa cctgaaatac ttaagtctat 1261 ccaactcctt tacaagtttg cgaactttga caaatgaaac atttgtatca cttgctcatt 1321 ctcccttaca catactcaac ctaaccaaga ataaaatctc aaaaatagag agtgatgctt 1381 tctcttggtt gggccaccta gaagtacttg acctgggcct taatgaaatt gggcaagaac 1441 tcacaggcca ggaatggaga ggtctagaaa atattttcga aatctatctt tcctacaaca 1501 agtacctgca gctgactagg aactcctttg ccttggtccc aagccttcaa cgactgatgc 1561 tccgaagggt ggcccttaaa aatgtggata gctctccttc accattccag cctcttcgta 1621 acttgaccat tctggatcta agcaacaaca acatagccaa cataaatgat gacatgttgg 1681 agggtcttga gaaactagaa attctcgatt tgcagcataa caacttagca cggctctgga 1741 aacacgcaaa ccctggtggt cccatttatt cctaaaggg tctgtctcac ctccacatcc 1801 ttaacttgga gtccaacggc tttgacgaga tcccagttga ggtcttcaag gatttatttg 1861 aactaaagat catcgattta ggattgaata atttaaacac acttccagca tctgtcttta 1921 ataatcaggt gtctctaaag tcattgaacc ttcagaagaa tctcataaca tccgttgaga 1981 agaaggtttt cgggccagct ttcaggaacc tgactgagtt agatatgcgc tttaatccct 2041 ttgattgcac gtgtgaaagt attgcctggt ttgttaattg gattaacgag acccatacca 2101 acatccctga gctgtcaagc cactaccttt gcaacactcc acctcactat catgggttcc 2161 cagtgagact ttttgataca tcatcttgca aagacagtgc ccccttttgaa ctcttttca 2221 tgatcaatac cagtatcctg ttgattttta tctttattgt acttctcatc cactttgagg 2281 gctggaggat atcttttat tggaatgttt cagtacatcg agttcttggt ttcaaagaaa 2341 tagacagaca gacagaacag tttgaatatg cagcatatat aattcatgcc tataaagata 2401 aggattgggt ctgggaacat ttctcttcaa tggaaaagga agaccaatct ctcaaatttt 2461 gtctggaaga aagggacttt gaggcgggtg ttttttgaact agaagcaatt gttaacagca 2521 tcaaaagaag cagaaaaatt attttttgtta taacacacca tctattaaaa gacccattat 2581 gcaaaagatt caaggtacat catgcagttc aacaagctat tgaacaaaat ctggattcca 2641 ttatattggt ttttccttgag gagattccag attataaact gaaccatgca ctctgtttgc 2701 gaagaggaat gtttaaatct cactgcatct tgaactggcc agttcagaaa gaacggatag 2761 gtgccttttcg tcataaattg caagtagcac ttggatccaa aaactctgta cattaaattt 2821 atttaaatat tcaattagca aaggagaaac tttctcaatt taaaaagttc tatggcaaat
```

```
-continued
2881 ttaagttttc cataaaggtg ttataatttg tttattcata tttgtaaatg attatattct 2941 atcacaatta catctcttct aggaaaatgt gtctccttat ttcaggccta tttttgacaa 3001 ttgacttaat tttacccaaa ataaaacata taagcacgta aaaaaaaaaa aaaaaaa
```

In some embodiments, the RNA complexes described herein are asiRNAs or lasiRNAs. As used herein, the term asiRNA refers to double-stranded asymmetrical short interfering RNA molecules that have a 19-21 nt antisense strand and a 13-17 nt sense strand. Additional information on asiRNAs can be found in U.S. Pat. Pub. No. 2012/0238017 and in Chang et al., *Mol. Ther.* 17:725-732 (2009), each of which is hereby incorporated by reference in its entirety. As used herein, the term lasiRNA refers to double-stranded long asymmetrical interfering RNA molecules that have a 13-21 nt sense strand and an antisense strand of greater than 24 nt. Additional information on lasiRNAs can be found in U.S. Pat. Pub. No. 2013/0273657, which is hereby incorporated by reference in its entirety.

In some embodiments, the RNA complexes described herein are delivered to cells using a delivery vehicle, such as liposomes, cationic polymers, cell penetrating peptides (CPPs), protein transduction domains (PTDs), antibodies and/or aptamers. In some embodiments, the RNA complex described herein is chemically modified so as to not require the use of such delivery vehicles to mediate MyD88 and/or TLR3 inhibition in a cell. Such RNA complexes are referred to herein as cell-penetrating asiRNAs (cp-asiRNAs) or cell-penetrating lasiRNAs (cp-lasiRNAs).

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering.

As used herein, the terms "interfering nucleic acid," "inhibiting nucleic acid" are used interchangeably. Interfering nucleic acids generally include a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. Interfering RNA molecules include, but are not limited to, antisense molecules, siRNA molecules, asiRNA molecules, lasiRNA molecules, single-stranded siRNA molecules, miRNA molecules and shRNA molecules. Such an interfering nucleic acids can be designed to block or inhibit translation of mRNA or to inhibit natural pre-mRNA splice processing, or induce degradation of targeted mRNAs, and may be said to be "directed to" or "targeted against" a target sequence with which it hybridizes. Interfering nucleic acids may include, for example, peptide nucleic acids (PNAs), locked nucleic acids (LNAs), 2'-O-Methyl oligonucleotides and RNA interference agents (siRNA agents). RNAi molecules generally act by forming a herteroduplex with the target molecule, which is selectively degraded or "knocked down," hence inactivating the target RNA. Under some conditions, an interfering RNA molecule can also inactivate a target transcript by repressing transcript translation and/or inhibiting transcription of the transcript. An interfering nucleic acid is more generally said to be "targeted against" a biologically relevant target, such as a protein, when it is targeted against the nucleic acid of the target in the manner described above.

The terms "polynucleotide", and "nucleic acid" are used interchangeably. They refer to a polymeric form of nucleotides, whether deoxyribonucleotides, ribonucleotides, or analogs thereof, in any combination and of any length. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. A polynucleotide may be further modified, such as by conjugation with a labeling component. In all nucleic acid sequences provided herein, U nucleotides are interchangeable with T nucleotides.

The phrase "pharmaceutically-acceptable carrier" as used herein means a pharmaceutically-acceptable material, composition or vehicle, such as a liquid or solid filler, diluent, excipient, or solvent encapsulating material.

An oligonucleotide "specifically hybridizes" to a target polynucleotide if the oligomer hybridizes to the target under physiological conditions, with a Tm substantially greater than 45° C., or at least 50° C., or at least 60° C.-80° C. or higher. Such hybridization corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

As used herein, a therapeutic that "prevents" a disorder or condition refers to a compound that, when administered to a statistical sample prior to the onset of the disorder or condition, reduces the occurrence of the disorder or condition in the treated sample relative to an untreated control sample, or delays the onset or reduces the severity of one or more symptoms of the disorder or condition relative to the untreated control sample.

RNA Complexes

In certain aspects, provided herein are RNA complexes that target MyD88 or TLR3 mRNA and inhibit MyD88 or TLR3 expression by a cell. The nucleic acid sequence of human MyD88 and TLR3 mRNA is provided in the sequence listing at the end of the disclosure.

In certain aspects, provided herein is an RNA complex comprising an antisense strand having sequence complementarity to a MyD88 or TLR3 mRNA sequence (e.g., a human MyD88 or TLR3 mRNA sequence) and a sense strand having sequence complementarity to the antisense strand. In some embodiments, the RNA complex is capable of inhibiting MyD88 or TLR3 expression by a cell. In some embodiments, the RNA complex is an asymmetric short interfering RNA (an asiRNA). In some embodiments, the RNA complex is a long asymmetric short interfering RNA (a lasiRNA). In some embodiments, the RNA complex is an RNA complex listed in Table 1, Table 2, Table 3, Table 4, Table 5, Table 6, Table 8 or Table 10. The RNA complexes described herein can contain RNA bases, non-RNA bases or a mixture of RNA bases and non-RNA bases. For example, certain RNA complexes provided herein can be primarily composed of RNA bases but also contain DNA bases or non-naturally occurring nucleotides.

In some embodiments, the antisense strand is at least 19 nucleotides (nt) in length. In some embodiments, the antisense strand is 19 to 21 nt in length (i.e., 19, 20 or 21 nt in length). In some embodiments, at least 13, 14, 15, 16, 17, 18, 19, 20 or 21 nt of the antisense strand are complementary to the MyD88 or TLR3 mRNA sequence. Perfect complementarity is not necessary. In some embodiments, the antisense strand is perfectly complementary to the MyD88 or TLR3 mRNA sequence.

In some embodiments, the antisense strand is at least 24 nt in length (e.g., at least 25 nt in length, at least 26 nt in length, at least 27 nt in length, at least 28 nt in length, at least 29 nt in length, at least 30 nt in length or at least 31 nt in length). In some embodiments, the antisense strand is no greater than 124 nt in length (e.g., no greater than 100 nt in length, no greater than 90 nt in length, no greater than 80 nt in length, no greater than 70 nt in length, no greater than 60 nt in length, no greater than 50 nt in length or no greater than 40 nt in length. In some embodiments, the antisense strand is 31 nt in length. In some embodiments, at least 16, 17, 18, 19, 20, 21, 22, 23, 24, 25, 26, 27, 29, 29, 30 or 31 nt of the antisense strand are complementary to the MyD88 or TLR3 mRNA sequence. Perfect complementarity is not necessary. In some embodiments, the antisense strand is perfectly complementary to the MyD88 or TLR3 mRNA sequence.

In some embodiments, the sense strand is 15 to 17 nt in length (i.e., 15 nt in length, 16 nt in length or 17 nt in length). In some embodiments, at least 15 nt, at least 16 nt or at least 17 nt of the sense strand are complementary to the sequence of the antisense strand. In some embodiments the sense strand is perfectly complementary to the sequence of the antisense strand.

In some embodiments, the antisense strand and the sense strand form a complex in which the 5' end of the antisense strand and the 3' end of the sense strand form a blunt end. In some embodiments, the antisense strand and the sense strand form a complex in which the 5' end of the antisense strand overhangs the 3' end of the sense strand (e.g., by 1, 2, 3, 4 or 5 nt). In some embodiments, the antisense strand and the sense strand form a complex in which the 5' end of the sense strand overhangs the 3' end of the antisense strand (e.g., by 1, 2, 3, 4 or 5 nt).

In some embodiments, the antisense strand and/or the sense strand of the RNA complex has a sense strand sequence and/or an antisense strand sequence selected from the sequences listed in Table 1, Table 2, Table 3, Table 4, Table 5, Table 6, Table 8 or Table 10.

In some embodiments, the RNA complex provided herein comprises a chemical modification, wherein the modification facilitates the penetration of a cellular membrane in the absence of a delivery vehicle. In some embodiments, the modification is a 2'-O-methylated nucleoside, a phosphorothioate bond or a cholesterol moiety. In some embodiments, the RNA complex is a modified RNA complex listed in Table 2 or Table 4. In certain embodiments, the RNA complex is not cytotoxic.

The RNA complexes described herein can employ a variety of oligonucleotide chemistries. Examples of oligonucleotide chemistries include, without limitation, peptide nucleic acid (PNA), linked nucleic acid (LNA), phosphorothioate, 2'O-Me-modified oligonucleotides, and morpholino chemistries, including combinations of any of the foregoing. In general, PNA and LNA chemistries can utilize shorter targeting sequences because of their relatively high target binding strength relative to 2'O-Me oligonucleotides. Phosphorothioate and 2'O-Me-modified chemistries are often combined to generate 2'O-Me-modified oligonucleotides having a phosphorothioate backbone. See, e.g., PCT Publication Nos. WO/2013/112053 and WO/2009/008725, each of which is hereby incorporated by reference in its entirety.

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition. The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969,766, 7,211,668, 7,022,851, 7,125,994, 7,145,006 and 7,179,896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is incorporated by reference in its entirety.

Interfering nucleic acids may also contain "locked nucleic acid" subunits (LNAs). "LNAs" are a member of a class of modifications called bridged nucleic acid (BNA). BNA is characterized by a covalent linkage that locks the conformation of the ribose ring in a C3-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., *Chemical Communications* (1998) 455; *Tetrahedron* (1998) 54:3607, and Accounts of Chem. Research (1999) 32:301); Obika, et al., *Tetrahedron Letters* (1997) 38:8735; (1998) 39:5401, and *Bioorganic Medicinal Chemistry* (2008) 16:9230. Compounds provided herein may incorporate one or more LNAs; in some cases, the compounds may be entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. One embodiment is an LNA-containing compound where each LNA subunit is separated by a DNA subunit. Certain compounds are composed of alternating LNA and DNA subunits where the intersubunit linker is phosphorothioate.

In certain embodiments, the RNA complex is linked to a cholesterol moiety. In some embodiments, the cholesterol moiety is attached to the 3' terminus of the sense strand. In some embodiments, the cholesterol moiety is attached to the 3' terminus of the antisense strand. In some embodiments, the cholesterol moiety is attached to the 5' terminus of the sense strand. In some embodiments, the cholesterol moiety is attached to the 5' terminus of the antisense strand.

In some embodiments, the RNA complex comprises a 2'-O-methylated nucleoside. 2'-O-methylated nucleosides carry a methyl group at the 2'-OH residue of the ribose molecule. 2'-O-Me-RNAs show the same (or similar) behavior as RNA, but are protected against nuclease degradation. 2'-O-Me-RNAs can also be combined with phosphothioate oligonucleotides (PTOs) for further stabilization. 2'-O-Me-RNAs (phosphodiester or phosphothioate) can be synthesized according to routine techniques in the art (see, e.g., Yoo et al., *Nucleic Acids Res.* 32:2008-16, 2004, which is hereby incorporated by reference).

In some embodiments, the 2'-O-methyl nucleoside is positioned at the 3' terminus of the sense strand. In some embodiments, 3' terminal region of the sense strand comprises a plurality of 2'-O-methylated nucleosides (e.g., 2, 3, 4, 5 or 6 2'-O-methylated nucleosides within 6 nucleosides of the 3' terminus). In some embodiments, the 2'-O-methyl nucleoside is positioned at the 3' terminus of the antisense strand. In some embodiments, 3' terminal region of the antisense strand comprises a plurality of 2'-O-methylated nucleosides (e.g., 2, 3, 4, 5 or 6 2'-O-methylated nucleosides within 6 nucleosides of the 3' terminus). In some embodiments, both the 3' terminal region of the sense strand and the 3' terminal region of the antisense strand comprise a plurality of 2'-O-methylated nucleosides. In some embodiments, the sense strand comprises 2'-O-methylated nucleosides that alternate with unmodified nucleosides. In some embodiments, the sense strand comprises a contiguous sequence of 2, 3, 4, 5, 6, 7 or 8 2'-O-methylated nucleosides that alternate with unmodified nucleosides. In some embodiments, the anti-sense strand comprises 2'-O-methylated nucleosides that alternate with unmodified nucleosides. In some embodiments, the anti-sense strand comprises a contiguous sequence of 2, 3, 4, 5, 6, 7 or 8 2'-O-methylated nucleosides that alternate with unmodified nucleosides.

In some embodiments, the RNA complex comprises a phosphorothioate bond. "Phosphorothioates" (or S-oligos) are a variant of normal DNA in which one of the nonbridging oxygens is replaced by a sulfur. The sulfurization of the internucleotide bond reduces the action of endo- and exo-nucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1,2-benzodithiol-3-one 1,1-dioxide (BDTD) (see, e.g., Iyer et al., *J. Org. Chem.* 55, 4693-4699, 1990). The latter methods avoid the problem of elemental sulfur's insolubility in most organic solvents and the toxicity of carbon disulfide. The TETD and BDTD methods also yield higher purity phosphorothioates.

In some embodiments, at least 25%, 30%, 35%, 40%, 45%, 50%, 55%, 60%, 65%, 70%, 75%, 80%, 85%, 90% or 95% of the bonds between the ribonucleotides in the sense strand of the RNA complex are phosphorothioate bonds. In some embodiments, all of the bonds between the ribonucleotides in the sense strand of the RNA complex are phosphorothioate bonds.

In some embodiments, at least 25%, 30%, 35%, 40%, 45%, 50%, 55%, 60%, 65%, 70%, 75%, 80%, 85%, 90% or 95% of the bonds between the ribonucleotides in the anti-sense strand of the RNA complex are phosphorothioate bonds. In some embodiments, all of the bonds between the ribonucleotides in the antisense strand of the RNA complex are phosphorothioate bonds.

The RNA complexes described herein may be contacted with a cell or administered to an organism (e.g., a human). Alternatively, constructs and/or vectors encoding the RNA complexes may be contacted with or introduced into a cell or organism. In certain embodiments, a viral, retroviral or lentiviral vector is used.

The RNA complexes described herein can be prepared by any appropriate method known in the art. For example, in some embodiments, the RNA complexes described herein are prepared by chemical synthesis or in vitro transcription.

In certain aspects, provided herein is a pharmaceutical composition comprising an RNA complex provided herein and a pharmaceutically acceptable carrier. In certain embodiments, the pharmaceutical composition is formulated for delivery to the eye (e.g., as an eye drop). In some embodiments, the pharmaceutical composition is formulated for intravitreal delivery.

In some embodiments, the pharmaceutical composition further comprises a second agent for treatment of AMD (e.g., an anti-VEGF therapeutic, such as bevacizumab, ranibizumab, pegaptanib and/or aflibercept). In certain embodiments, the pharmaceutical composition does not comprise a transfection vehicle. In some embodiments, the pharmaceutical composition comprises a delivery vehicle (e.g., liposomes, cationic polymers, cell penetrating peptides (CPPs), protein transduction domains (PTDs), antibodies and/or aptamers). In some embodiments, the composition includes a combination of multiple (e.g., two or more) of the RNA complexes described herein.

Methods of preparing these formulations or compositions include the step of bringing into association an RNA complex described herein with the carrier and, optionally, one or more accessory ingredients. In general, the formulations are prepared by uniformly and intimately bringing into association an agent described herein with liquid carriers.

Therapeutic Methods

In certain aspects, provided herein is a method of inhibiting MyD88 and/or TLR3 expression by a cell comprising contacting the cell with an RNA complex provided herein. In some embodiments, the RNA complex is a modified RNA complex and the cell is contacted with the RNA complex in the absence of a transfection vehicle. In some embodiments, the cell is contacted with the RNA complex in the presence of a delivery vehicle (e.g., a liposome, cationic polymer, cell penetrating peptide (CPPs), protein transduction domain (PTDs), antibody and/or aptamer). In some embodiments, the cell is present in the eye of a human subject. In some embodiments, the subject has AMD (e.g., wet AMD or dry AMD).

In certain aspects, provided herein is a method of treating a human subject for AMD (e.g., wet AMD or dry AMD) comprising administering to the subject an RNA complex or pharmaceutical composition provided herein. In certain embodiments, the RNA complex or pharmaceutical composition is administered to the eye of the subject. In some embodiments, the RNA complex or pharmaceutical composition self-administered by the subject.

In the present methods, an RNA complex described herein can be administered to the subject, for example, as nucleic acid without delivery vehicle (e.g., for cp-asiRNAs and cp-lasiRNAs), in combination with a delivery reagent, and/or as a nucleic acid comprising sequences that express the RNA complex described herein. In some embodiments, any nucleic acid delivery method known in the art can be used in the methods described herein. Suitable delivery reagents include, but are not limited to, e.g., the Mirus Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. *Nucleic Acids Res.*, 32(13):e109 (2004); Hanai et al. *Ann NY Acad Sci.*, 1082:9-17 (2006); and Kawata et al. *Mol Cancer Ther.*, 7(9):2904-12 (2008); each of which is incorporated herein in their entirety. Exemplary interfering nucleic acid delivery systems are provided in U.S. Pat. Nos. 8,283,461, 8,313,772, 8,501,930. 8,426,554, 8,268,798 and 8,324,366, each of which is hereby incorporated by reference in its entirety.

In some embodiments of the methods described herein, liposomes are used to deliver an RNA complex described herein to a subject. Liposomes suitable for use in the methods described herein can be formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are herein incorporated by reference.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure.

Opsonization-inhibiting moieties for use in preparing the liposomes described herein are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference.

In some embodiments, opsonization inhibiting moieties suitable for modifying liposomes are water-soluble polymers with a number-average molecular weight from about 500 to about 40,000 daltons, or from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. In some embodiments, the opsonization-inhibiting moiety is a PEG, PPG, or derivatives thereof. Liposomes modified with PEG or PEG-derivatives are sometimes called "PEGylated liposomes."

The pharmaceutical compositions disclosed herein may be delivered by any suitable route of administration, including topically, intravitreally, orally and parenterally. In certain embodiments the pharmaceutical compositions are delivered generally (e.g., via oral or parenteral administration). In certain other embodiments the pharmaceutical compositions are delivered locally through direct administration to the eye.

Actual dosage levels of the RNA complexes in the pharmaceutical compositions may be varied so as to obtain an amount of RNA complex that is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician having ordinary skill in the art can readily determine and prescribe the effective amount of the pharmaceutical composition required. For example, the physician or veterinarian could prescribe and/or administer doses of the agents employed in the pharmaceutical composition at levels lower than that required in order to achieve the desired therapeutic effect and gradually increase the dosage until the desired effect is achieved.

In general, a suitable daily dose of an RNA complex described herein will be that amount of the RNA complex which is the lowest dose effective to produce a therapeutic effect. Such an effective dose will generally depend upon the factors described above.

EXEMPLIFICATION

Example 1: Screening for MyD88-Specific Asymmetric Small Interfering RNAs

To identify asymmetric small interfering RNAs (asiRNAs) that inhibit MyD88 with high efficiency, 44 asiRNAs were synthesized and screened. The nucleic acid sequences of the screened asiRNAs are provided in Table 1.

TABLE 1

Nucleic acid sequences for exemplary MyD88-targeting asiRNA.

| asiRNA SEQUENCE | SEQ ID NO: |
|---|---|
| MyD88#1(S): 5' GGCGGCCGACUGGACC 3' | 3 |
| MyD88#1(AS): 5' GGUCCAGUCGGCCGCCACC 3' | 4 |
| MyD88#2(S): 5' UGGCGGCCGACUGGAC 3' | 5 |
| MyD88#2(AS): 5' GUCCAGUCGGCCGCCACCU 3' | 6 |
| MyD88#3(S): 5' GUGGCGGCCGACUGGA 3' | 7 |
| MyD88#3(AS): 5' UCCAGUCGGCCGCCACCUG 3' | 8 |
| MyD88#4(S): 5' CUGGCGGAGGAGAUGG 3' | 9 |
| MyD88#4(AS): 5' CCAUCUCCUCCGCCAGCGC 3' | 10 |
| MyD88#5(S): 5' GCUGGCGGAGGAGAUG 3' | 11 |
| MyD88#5(AS): 5' CAUCUCCUCCGCCAGCGCG 3' | 12 |
| MyD88#6(S): 5' AGUACUUGGAGAUCCG 3' | 13 |
| MyD88#6(AS): 5' CGGAUCUCCAAGUACUCAA 3' | 14 |
| MyD88#7(S): 5' GAGUACUUGGAGAUCC 3' | 15 |
| MyD88#7(AS): 5' GGAUCUCCAAGUACUCAAA 3' | 16 |
| MyD88#8(S): 5' GCCUUUACAGGUGGCC 3' | 17 |
| MyD88#8(AS): 5' GGCCACCUGUAAAGGCUUC 3' | 18 |
| MyD88#9(S): 5' AGCCUUUACAGGUGGC 3' | 19 |
| MyD88#9(AS): 5' GCCACCUGUAAAGGCUUCU 3' | 20 |
| MyD88#10(S): 5' AAGCCUUUACAGGUGG 3' | 21 |

TABLE 1-continued

Nucleic acid sequences for exemplary MyD88-targeting asiRNA.

| asiRNA SEQUENCE | SEQ ID NO: |
|---|---|
| MyD88#10(AS): 5' CCACCUGUAAAGGCUUCUC 3' | 22 |
| MyD88#11(S): 5' GAAGCCUUUACAGGUG 3' | 23 |
| MyD88#11(AS): 5' CACCUGUAAAGGCUUCUCA 3' | 24 |
| MyD88#12(S): 5' AGAAGCCUUUACAGGU 3' | 25 |
| MyD88#12(AS): 5' ACCUGUAAAGGCUUCUCAG 3' | 26 |
| MyD88#13(S): 5' AGAUGAUCCGGCAACU 3' | 27 |
| MyD88#13(AS): 5' AGUUGCCGGAUCAUCUCCU 3' | 28 |
| MyD88#14(S): 5' GAGAUGAUCCGGCAAC 3' | 29 |
| MyD88#14(AS): 5' GUUGCCGGAUCAUCUCCUG 3' | 30 |
| MyD88#15(S): 5' GGAGAUGAUCCGGCAA 3' | 31 |
| MyD88#15(AS): 5' UUGCCGGAUCAUCUCCUGC 3' | 32 |
| MyD88#16(S): 5' AGGAGAUGAUCCGGCA 3' | 33 |
| MyD88#16(AS): 5' UGCCGGAUCAUCUCCUGCA 3' | 34 |
| MyD88#17(S): 5' CAGGAGAUGAUCCGGC 3' | 35 |
| MyD88#17(AS): 5' GCCGGAUCAUCUCCUGCAC 3' | 36 |
| MyD88#18(S): 5' GCAGGAGAUGAUCCGG 3' | 37 |
| MyD88#18(AS): 5' CCGGAUCAUCUCCUGCACA 3' | 38 |
| MyD88#19(S): 5' UGCAGGAGAUGAUCCG 3' | 39 |
| MyD88#19(AS): 5' CGGAUCAUCUCCUGCACAA 3' | 40 |
| MyD88#20(S): 5' GUGCAGGAGAUGAUCC 3' | 41 |
| MyD88#20(AS): 5' GGAUCAUCUCCUGCACAAA 3' | 42 |
| MyD88#21(S): 5' UGUGCAGGAGAUGAUC 3' | 43 |
| MyD88#21(AS): 5' GAUCAUCUCCUGCACAAAC 3' | 44 |
| MyD88#22(S): 5' UUGUGCAGGAGAUGAU 3' | 45 |
| MyD88#22(AS): 5' AUCAUCUCCUGCACAAACU 3' | 46 |
| MyD88#23(S): 5' UUUGUGCAGGAGAUGA 3' | 47 |
| MyD88#23(AS): 5' UCAUCUCCUGCACAAACUG 3' | 48 |
| MyD88#24(S): 5' GUUUGUGCAGGAGAUG 3' | 49 |
| MyD88#24(AS): 5' CAUCUCCUGCACAAACUGG 3' | 50 |

TABLE 1-continued

Nucleic acid sequences for exemplary MyD88-targeting asiRNA.

| asiRNA SEQUENCE | SEQ ID NO: |
|---|---|
| MyD88#25(S): 5' AGUUUGUGCAGGAGAU 3' | 51 |
| MyD88#25(AS): 5' AUCUCCUGCACAAACUGGA 3' | 52 |
| MyD88#26(S): 5' GUGACUUCCAGACCAA 3' | 53 |
| MyD88#26(AS): 5' UUGGUCUGGAAGUCACAUU 3' | 54 |
| MyD88#27(S): 5' UGUGACUUCCAGACCA 3' | 55 |
| MyD88#27(AS): 5' UGGUCUGGAAGUCACAUUC 3' | 56 |
| MyD88#28(S): 5' AUGUGACUUCCAGACC 3' | 57 |
| MyD88#28(AS): 5' GGUCUGGAAGUCACAUUCC 3' | 58 |
| MyD88#29(S): 5' AAUGUGACUUCCAGAC 3' | 59 |
| MyD88#29(AS): 5' GUCUGGAAGUCACAUUCCU 3' | 60 |
| MyD88#30(S): 5' GAAUGUGACUUCCAGA 3' | 61 |
| MyD88#30(AS): 5' UCUGGAAGUCACAUUCCUU 3' | 62 |
| MyD88#31(S): 5' GGAAUGUGACUUCCAG 3' | 63 |
| MyD88#31(AS): 5' CUGGAAGUCACAUUCCUUG 3' | 64 |
| MyD88#32(S): 5' AGGAAUGUGACUUCCA 3' | 65 |
| MyD88#32(AS): 5' UGGAAGUCACAUUCCUUGC 3' | 66 |
| MyD88#33(S): 5' AAGGAAUGUGACUUCC 3' | 67 |
| MyD88#33(AS): 5' GGAAGUCACAUUCCUUGCU 3' | 68 |
| MyD88#34(S): 5' CAAGGAAUGUGACUUC 3' | 69 |
| MyD88#34(AS): 5' GAAGUCACAUUCCUUGCUC 3' | 70 |
| MyD88#35(S): 5' GCAAGGAAUGUGACUU 3' | 71 |
| MyD88#35(AS): 5' AAGUCACAUUCCUUGCUCU 3' | 72 |
| MyD88#36(S): 5' AGCAAGGAAUGUGACU 3' | 73 |
| MyD88#36(AS): 5' AGUCACAUUCCUUGCUCUG 3' | 74 |
| MyD88#37(S): 5' GAGCAAGGAAUGUGAC 3' | 75 |
| MyD88#37(AS): 5' GUCACAUUCCUUGCUCUGC 3' | 76 |
| MyD88#38(S): 5' AGAGCAAGGAAUGUGA 3' | 77 |
| MyD88#38(AS): 5' UCACAUUCCUUGCUCUGCA 3' | 78 |
| MyD88#39(S): 5' CAGAGCAAGGAAUGUG 3' | 79 |
| MyD88#39(AS): 5' CACAUUCCUUGCUCUGCAG 3' | 80 |
| MyD88#40(S): 5' GUCCCUGCCCUGAAGA 3' | 81 |
| MyD88#40(AS): 5' UCUUCAGGGCAGGGACAAG 3' | 82 |
| MyD88#41(S): 5' UGUCCCUGCCCUGAAG 3' | 83 |
| MyD88#41(AS): 5' CUUCAGGGCAGGGACAAGG 3' | 84 |
| MyD88#42(S): 5' UUGUCCCUGCCCUGAA 3' | 85 |
| MyD88#42(AS): 5' UUCAGGGCAGGGACAAGGC 3' | 86 |
| MyD88#43(S): 5' GCACCUGUGUCUGGUC 3' | 87 |
| MyD88#43(AS): 5' GACCAGACACAGGUGCCAG 3' | 88 |
| MyD88#44(S): 5' GGCACCUGUGUCUGGU 3' | 89 |
| MyD88#44(AS): 5' ACCAGACACAGGUGCCAGG 3' | 90 |

The asiRNAs listed in Table 1 were incubated at 95° C. for 2 minutes and at 37° C. for 1 hour in 1×siRNA duplex buffer (STpharm). Proper strand annealing was confirmed via gel electrophoresis. For the screen, HeLa cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. One day prior to transfection, 2.0×10$^4$ HeLa cells were seeded in 24-well plates. The HeLa cells were transfected with 0.3 nM of the asiRNAs using Lipofectamine 2000 (Invitrogen) according to the manufacturer's instructions.

The MyD88 mRNA levels in the transfected cells were measured 24 hours after transfection using real-time PCR. Specifically, total RNA were extracted using RNAiso Plus (TaKaRa), and then 500 ng of the extracted RNA was used for cDNA synthesis using the High-capacity cDNA reverse transcription kit (Applied Biosystems), according to the manufacturer's instructions. The synthesized cDNA was diluted and then quantitative real-time PCR was performed using the StepOne real-time PCR system (Applied Biosystems) according to manufacturer's instructions. Amplification of the MyD88 gene was detected using a power SYBR Premix Ex Taq (TaKaRa). GAPDH was amplified as an internal control. The following primer sequences were used:

Human GAPDH-forward (SEQ ID NO: 91)
5'-GAG TCA ACG GAT TTG GTC GT-3'

Human GAPDH-reverse (SEQ ID NO: 92)
5'-GAC AAG CTT CCC GTT CTC AG-3'

-continued

```
Human MyD88-forward              (SEQ ID NO: 93)
5'-AAG TTA TTT GTT TAC AAA CAG CGA CCA-3'

Human MyD88-reverse              (SEQ ID NO: 94)
5'-GGA AGA ATG GCA AAT ATC GGC T-3'
```

The level of MyD88 inhibition by each of the 44 asiRNAs is provided in FIG. 1. Three of the asiRNA sequences, asiMyD88(26), asiMyD88(27) and asiMyD88(32), were selected for use in follow-up studies.

Example 2: Inhibition of MyD88 mRNA Expression Level Using MyD88-Targeting asiRNAs Three of the asiRNA sequences, asiMyD88(26), asiMyD88(27) and asiMyD88(32), were tested for their ability to inhibit MyD88 expression at different concentrations. The asiRNAs were incubated at 95° C. for 2 minutes and at 37° C. for 1 hour in 1×siRNA duplex buffer (STpharm). Proper strand annealing was confirmed via gel electrophoresis. For the screen, HeLa cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. One day prior to transfection, $2.0 \times 10^4$ HeLa cells were seeded in 24-well plates. The HeLa cells were transfected with asiRNAs using Lipofectamine 2000 (Invitrogen) according to the manufacturer's instructions.

Figure 2:
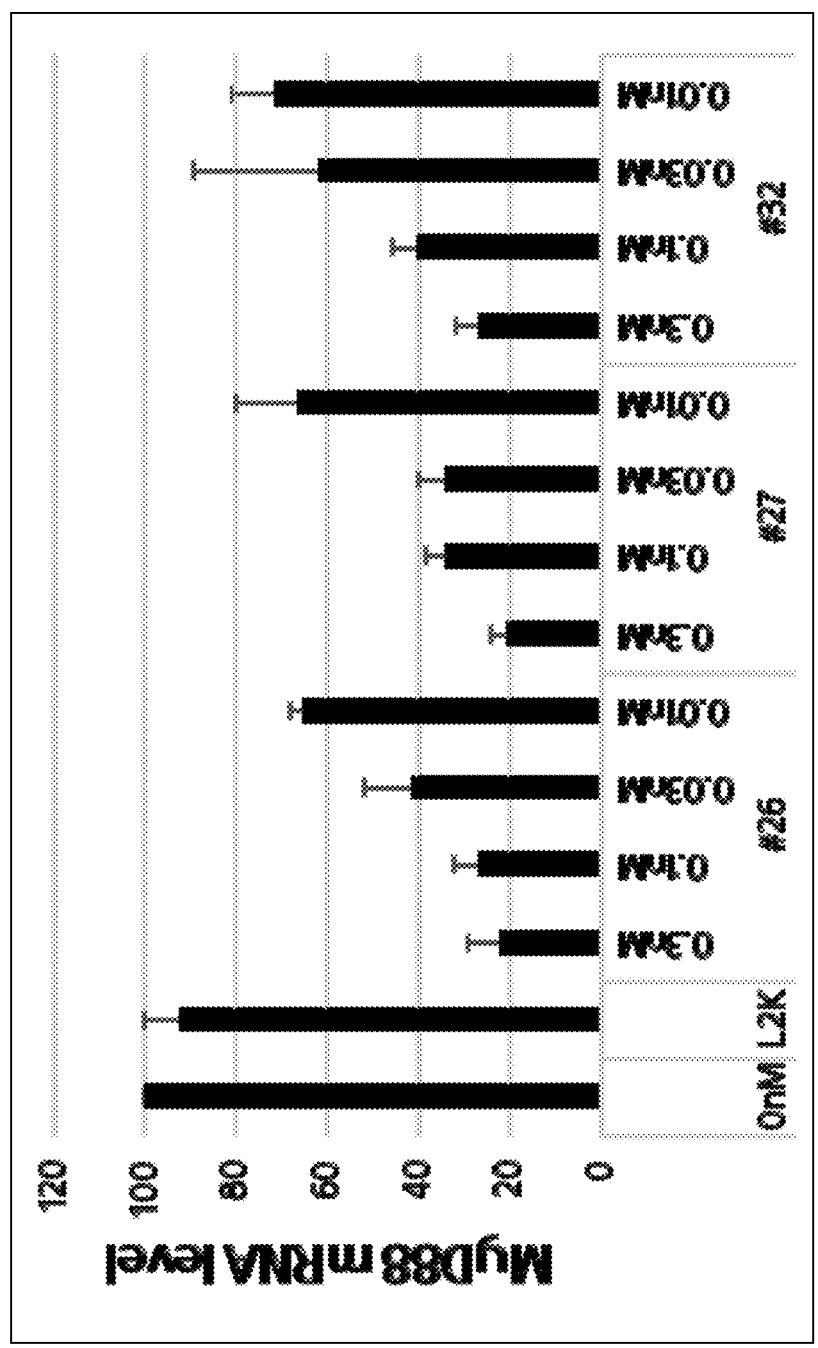
FIG. 2 shows the gene silencing efficiency of exemplary asiRNAs that target MyD88. The asiRNAs were transfected into HeLa cells at a concentration of 0.3 nM, 0.1 nM, 0.03 nM and 0.01 nM, and, after 24 hours, the degree of MyD88 mRNA expression was determined using real-time PCR. The mean and standard deviation of three repeat experiments are depicted.

The level of MyD88 inhibition by the different concentrations of the 3 asiRNAs is provided in FIG. 2. As seen in FIG. 2, low concentration of asiMyD88(26) and asiMyD88(27) exhibited the highest levels of MyD88 inhibition. asiMyD88(26) and asiMyD88(27) were selected for use in follow-up studies.

Example 3: Modification of asiRNAs

A variety of potential asiMyD88 structures having different antisense strand lengths were synthesized and tested for their ability to inhibit MyD88 expression. (Table 2)

TABLE 2

Additional asiRNA sequences.

```
MyD88#26(S):                            (SEQ ID
5' GUGACUUCCAGACCAA 3'                  NO: 53)

MyD88#26(19AS):                         (SEQ ID
5' UUGGUCUGGAAGUCACAUU 3'               NO: 54)

MyD88#26(21AS):                         (SEQ ID
5' UUGGUCUGGAAGUCACAUUCC 3'             NO: 95)

MyD88#26(31AS):                         (SEQ ID
5' UUGGUCUGGAAGUCACAUUCCUUGCUCUGCA 3'   NO: 96)

MyD88#27(S):                            (SEQ ID
5' UGUGACUUCCAGACCA 3'                  NO: 97)

MyD88#27(19AS):                         (SEQ ID
5' UGGUCUGGAAGUCACAUUC 3'               NO: 56)

MyD88#27(21AS):                         (SEQ ID
5' UGGUCUGGAAGUCACAUUCCU 3'             NO: 98)

MyD88#27(31AS):                         (SEQ ID
5' UGGUCUGGAAGUCACAUUCCUUGCUCUGCAG 3'   NO: 99)
```

The asiRNAs listed in Table 2 were incubated at 95° C. for 2 minutes and at 37° C. for 1 hour in 1×siRNA duplex buffer (STpharm). Proper strand annealing was confirmed via gel electrophoresis. For the screen, HeLa cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. One day prior to transfection, $2.0 \times 10^4$ HeLa cells were seeded in 24-well plates. The HeLa cells were transfected with 0.3 nM of the asiRNAs using Lipofectamine 2000 (Invitrogen) according to the manufacturer's instructions.

The MyD88 mRNA levels in the transfected cells were measured 24 hours after transfection using real-time RT-PCR. Specifically, total RNA were extracted using RNAiso Plus(TaKaRa), and then 500 ng of the extracted RNA was used for cDNA synthesis using the High-capacity cDNA reverse transcription kit (Applied Biosystems), according to the manufacturer's instructions. The synthesized cDNA was diluted and then quantitative real-time PCR was performed using the StepOne real-time PCR system (Applied Biosystems) according to manufacturer's instructions. Amplification of the MyD88 gene was detected using a power SYBR Premix Ex Taq (TaKaRa). GAPDH was amplified as an internal control.

Figure 3:
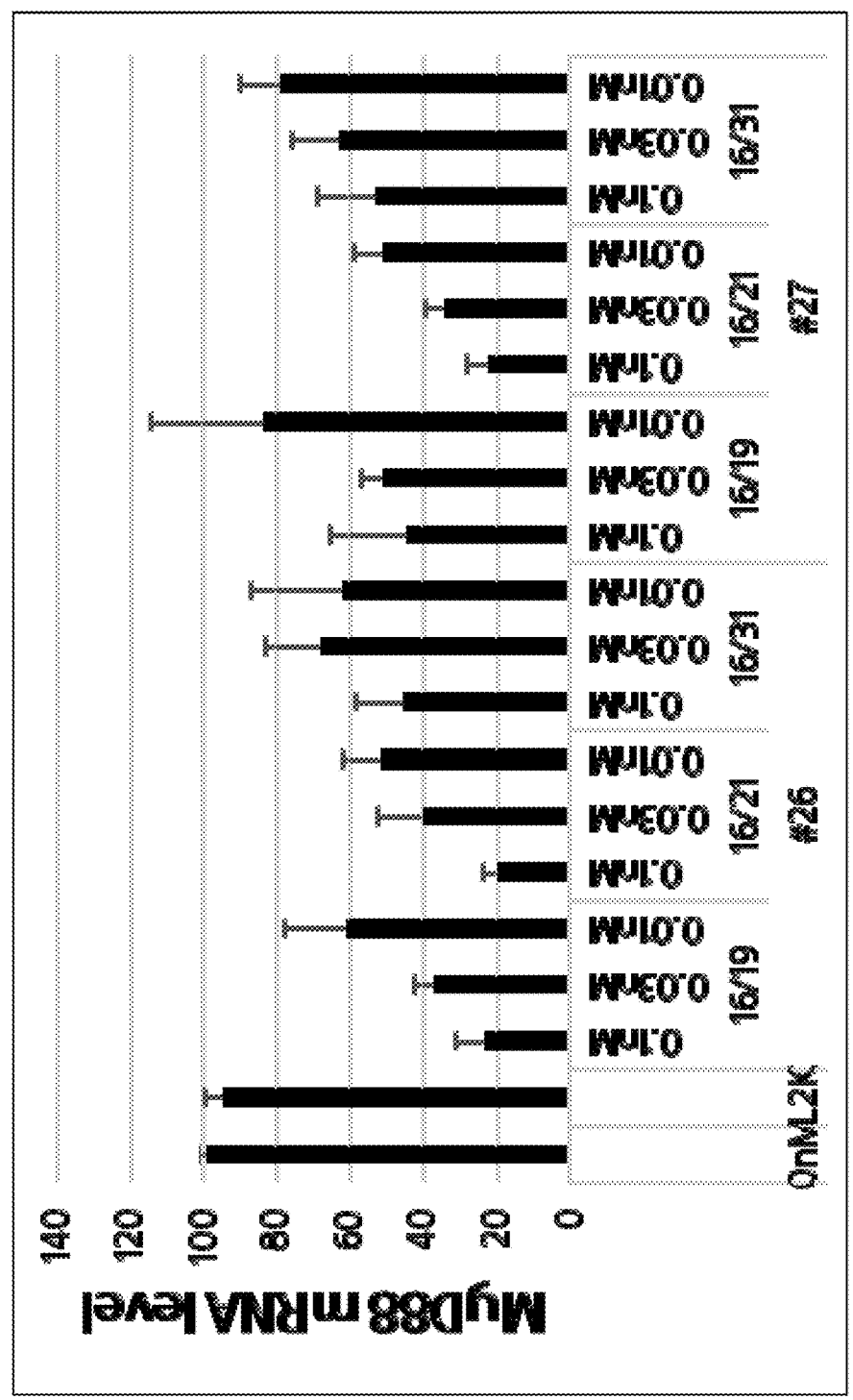
FIG. 3 shows the gene silencing effect of exemplary asiRNAs having different antisense strand lengths (19, 21 or 31 nucleotides) that target MyD88. The asiRNAs were transfected into HeLa cells at a concentration of 0.1 nM, 0.03 nM or 0.01 nM, and, after 24 hours, the degree of MyD88 mRNA expression was determined using real-time PCR. The mean and standard deviation of three repeat experiments are depicted.

The level of MyD88 inhibition by each of the 6 asiRNAs is provided in FIG. 3. 21 nucleotide antisense of asiMyD88 (26) and asiMyD88(27) exhibited the highest levels of MyD88 inhibition. 21 nucleotide antisense were selected for use in follow-up studies.

Example 4: Inhibition of MyD88 Protein Using MyD88-Specific asiRNAs

The efficacy of asiMyD88 for the inhibition of MyD88 protein was tested.

The asiRNAs were incubated at 95° C. for 2 minutes and at 37° C. for 1 hour in 1×siRNA duplex buffer (STpharm). Proper strand annealing was confirmed via gel electrophoresis.

A549 cells (ATCC) and HeLa cells (ATCC) were used that had been cultured in Dulbecco's modified Eagle's medium (Gibco) containing 10% fetal bovine serum (Gibco) and 100 µg/ml penicillin/streptomycin in a 100 mm cell culture dish. One day prior to transfection, $5.0 \times 10^4$ A549 cells or HeLa cells were seeded in 12-well plates. A549 cells and HeLa cells were transfected with 10 nM and 3 nM of the asiRNAs using Lipofectamine™ RNAiMAX (Invitrogen) according to the manufacturer's instructions. After 24 hours, OPTI-MEM media was replaced with a serum-containing media.

After 48 hours of asiRNA transfection, the level of MyD88 protein expression was determined via western blot. Briefly, the transfected A549 cells and HeLa cells were lysed with RIPA buffer (GE). 15 µg of the total protein extract of A549 cells or 30 µg of the total protein extract of HeLa cells were loaded onto a 12% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-MyD88 antibody (Abcam) and anti-β-actin antibody (Santa Cruz). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The MyD88 and β-actin bands were then imaged using a Chemidoc instrument (Bio-rad).

Figure 4:
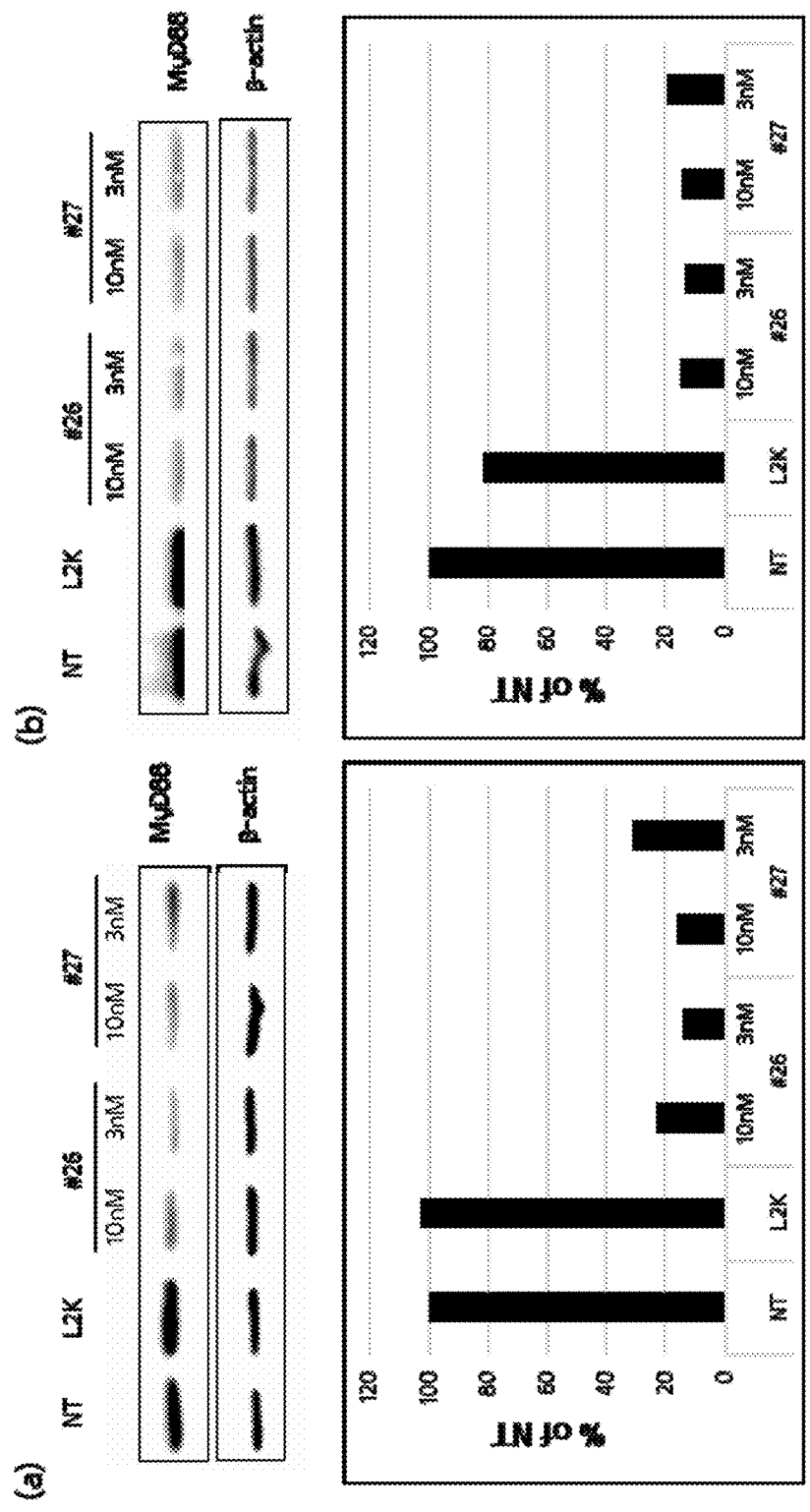
FIG. 4 shows the inhibition of MyD88 protein expression by exemplary asiRNAs that target MyD88. The asiRNAs were transfected into A549 or HeLa cells at a concentration of 3 nM or 10 nM, and, after 48 hours, protein was extracted and a western blot performed. Panel (a) depicts the MyD88 protein expression level in A549 cells 48 hours after transfection. Panel (b) depicts the MyD88 protein expression level in in HeLa cells 48 hours after transfection. (NT=no treatment, L2K=transfection control).

The results of the western blot assay are depicted in FIG. 4. In all asiMyD88 transfection cell lines of A549 cells and HeLa cells, 80% or more of MyD88 protein inhibition were confirmed. (FIG. 4).

Example 5: Chemical Modification of MyD88 asiRNAs

Chemical modifications were applied to the asiRNAs. As described below, certain of the modifications improved endocytosis and stability of the asiRNAs. Four asiRNAs (Table 3) were tested for MyD88 mRNA inhibition in HeLa cells

TABLE 3

Modified asiRNA sequences. m = 2'-O-Methyl RNA

MyD88#26(16S-1):                                    (SEQ ID NO: 100)
5' mGUmGAmCUmUCmCAmGAmCCmAA 3'

MyD88#26(19AS-1):                                   (SEQ ID NO: 101)
5' UUGGUCUGGAAGUCmAmCmAmUmU 3'

MyD88#26(21AS-1):                                   (SEQ ID NO: 102)
5' UUGGUCUGGAAGUCmAmCmAmUmUmCmC 3'

MyD88#27(16S-1):                                    (SEQ ID NO: 103)
5' mUGmUGmACmUUmCCmAGmACmCA 3'

MyD88#27(19AS-1):                                   (SEQ ID NO: 104)
5' UGGUCUGGAAGUCAmCmAmUmUmC 3'

MyD88#27(21AS-1):                                   (SEQ ID NO: 105)
5' UGGUCUGGAAGUCAmCmAmUmUmCmCmU 3'

HeLa cells (ATCC) were used that had been cultured in Dulbecco's modified Eagle's medium (Gibco) containing 10% fetal bovine serum (Gibco) and 100 μg/ml penicillin/streptomycin in a 100 mm cell culture dish. One day prior to transfection, 2.0×10⁴ HeLa cells were seeded in 24-well plates. The HeLa cells were transfected using Lipofectamine 2000 (Invitrogen) according to the manufacturer's instructions. Twenty-four hours later, MyD88 mRNA levels were in the HeLa cells were determined.

Figure 5:
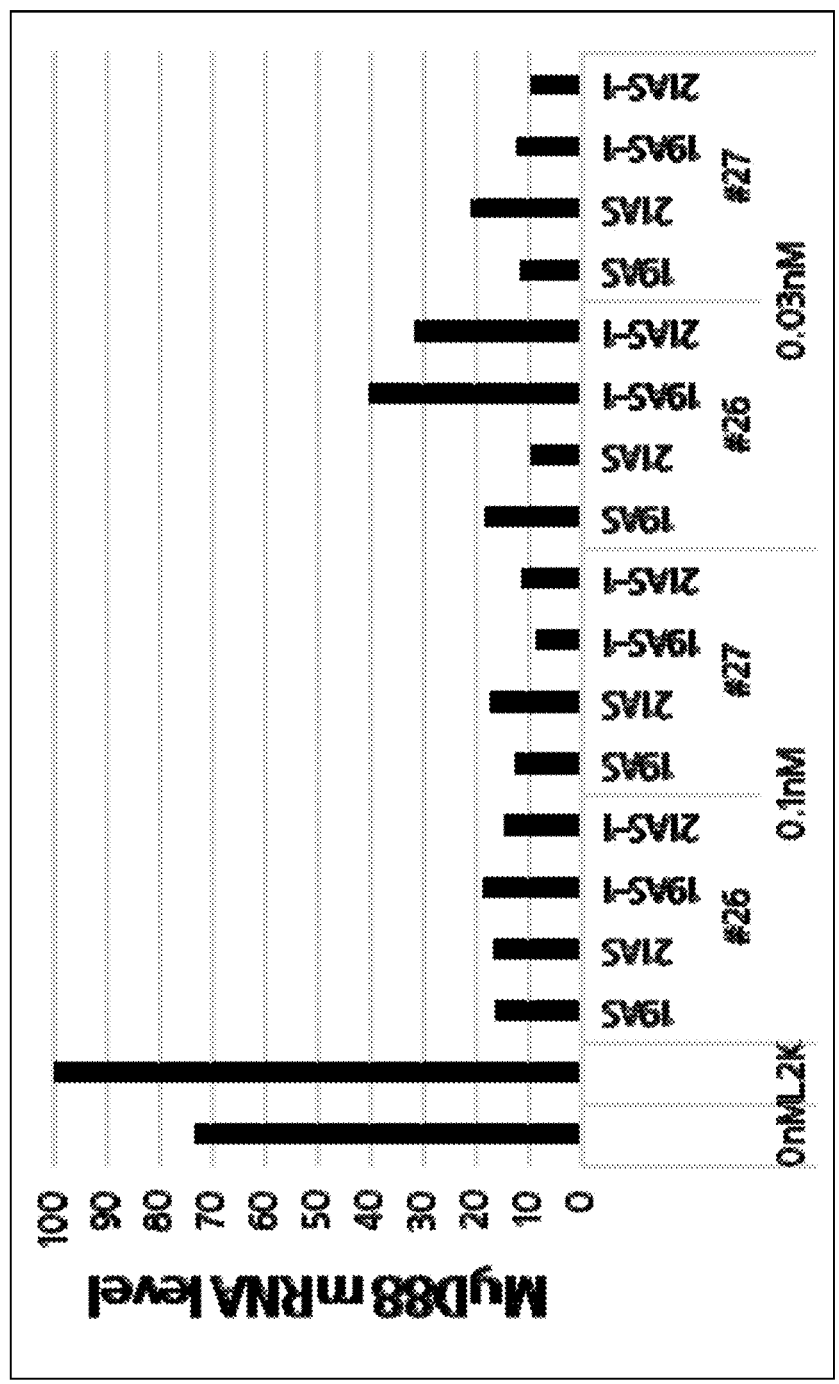
FIG. 5 shows the gene silencing efficiency of exemplary asiRNAs containing 2'-O-Methylation modifications. The asiRNAs were transfected into HeLa cells at a concentration of 0.1 nM or 0.03 nM, and, after 24 hours, the degree of MyD88 mRNA expression was determined using real-time PCR.

The level of MyD88 inhibition by each of the asiRNAs in provided in FIG. 5. Modified MyD88(27) exhibited the highest levels of MyD88 inhibition.

Example 6: Chemical Modification of asiRNAs for Self-Delivery

Chemical modifications were applied to the asiRNAs and the cellular delivery of the modified asiRNAs was tested in the absence of other delivery vehicle. As described below, certain of the modifications improved endocytosis and stability of the asiRNAs. Such cell penetrating asiRNAs (cp-asiRNAs) are able to be delivered into the cell in the absence of a delivery vehicle.

Twenty potential cp-asiRNAs (Table 4) were screened for MyD88 mRNA inhibition in HeLa cells. Each potential cp-asiRNA was incubated with HeLa cells at 1 μM without a delivery vehicle and MyD88 mRNA levels were measured by Real-Time PCR.

TABLE 4

Modified asiRNA sequences tested for self-delivery and MyD88 inhibition.
m = 2'-O-Methyl RNA, * = phosphorothioate bond.

cp-asiMyD88#26-1(S):                                (SEQ ID NO: 106)
5' GUGACUUCCAGACC*A*A*cholesterol 3' cp-asiMyD88#26-1(AS):                               (SEQ ID NO: 107)
5' UUGGUCUGGAAGUCACA*U*U*C*C 3' cp-asiMyD88#26-2(S):                                (SEQ ID NO: 108)
5' GUGACUUCCAGACC*A*A*cholesterol 3' cp-asiMyD88#26-2(AS):                               (SEQ ID NO: 109)
5' UUGGUCUGGAAGUCACA*U*mU*mC*mC 3' cp-asiMyD88#26-3(S):                                (SEQ ID NO: 110)
5' GUGACUUCCAGACC*A*A*cholesterol 3' cp-asiMyD88#26-3(AS):                               (SEQ ID NO: 111)
5' UUGGUCUGGAAGUCACmA*mU*mU*mC*mC 3' cp-asiMyD88#26-4(S):                                (SEQ ID NO: 112)
5' GUGACUUCCAGACC*A*A*cholesterol 3' cp-asiMyD88#26-4(AS):                               (SEQ ID NO: 113)
5' UUGGUCUGGAAGUCmAmCmA*mU*U*C*C 3' cp-asiMyD88#26-5(S):                                (SEQ ID NO: 114)
5' GUGACUUCCAGACC*A*A*cholesterol 3' cp-asiMyD88#26-5(AS):                               (SEQ ID NO: 115)
5' UUGGUCUGGAAGUCmAmCA*U*U*C*C 3' cp-asiMyD88#26-6(S):                                (SEQ ID NO: 116)
5' mGUmGAmCUmUCmCAmGAmCC*mA*A*cholesterol 3' cp-asiMyD88#26-6(AS):                               (SEQ ID NO: 117)
5' UUGGUCUGGAAGUCACA*U*U*C*C 3' cp-asiMyD88#26-7(S):                                (SEQ ID NO: 118)
5' mGUmGAmCUmUCmCAmGAmCC*mA*A*cholesterol 3' cp-asiMyD88#26-7(AS):                               (SEQ ID NO: 119)
5' UUGGUCUGGAAGUCACA*U*mU*mC*mC 3' cp-asiMyD88#26-8(S):                                (SEQ ID NO: 120)
5' mGUmGAmCUmUCmCAmGAmCC*mA*A*cholesterol 3' cp-asiMyD88#26-8(AS):                               (SEQ ID NO: 121)
5' UUGGUCUGGAAGUCACmA*mU*mU*mC*mC 3' cp-asiMyD88#26-9(S):                                (SEQ ID NO: 122)
5' mGUmGAmCUmUCmCAmGAmCC*mA*A*cholesterol 3' cp-asiMyD88#26-9(AS):                               (SEQ ID NO: 123)
5' UUGGUCUGGAAGUCmAmCmA*mU*U*C*C 3' cp-asiMyD88#26-10(S):                               (SEQ ID NO: 124)
5' mGUmGAmCUmUCmCAmGAmCC*mA*A*cholesterol 3' cp-asiMyD88#26-10(AS):                              (SEQ ID NO: 125)
5' UUGGUCUGGAAGUCmAmCA*U*U*C*C 3' cp-asiMyD88#27-1(S):                                (SEQ ID NO: 126)
5' UGUGACUUCCAGAC*C*A*cholesterol 3' cp-asiMyD88#27-1(AS):                               (SEQ ID NO: 127)
5' UGGUCUGGAAGUCACAU*U*C*C*U 3' cp-asiMyD88#27-2(S):                                (SEQ ID NO: 128)
5' UGUGACUUCCAGAC*C*A*cholesterol 3' cp-asiMyD88#27-2(AS):                               (SEQ ID NO: 129)
5' UGGUCUGGAAGUCACAU*U*mC*mC*mU 3'

TABLE 4-continued

Modified asiRNA sequences tested for
self-delivery and MyD88 inhibition.
m = 2'-O-Methyl RNA, * = phosphorothioate bond.

| | |
|---|---|
| cp-asiMyD88#27-3(S):<br>5' UGUGACUUCCAGAC*C*A*cholesterol 3' | (SEQ ID<br>NO: 130) |
| cp-asiMyD88#27-3(AS):<br>5' UGGUCUGGAAGUCACAmU*mU*mC*mC*mU 3' | (SEQ ID<br>NO: 131) |
| cp-asiMyD88#27-4(S):<br>5' UGUGACUUCCAGAC*C*A*cholesterol 3' | (SEQ ID<br>NO: 132) |
| cp-asiMyD88#27-4(AS):<br>5' UGGUCUGGAAGUCAmCmAmU*mU*C*C*U 3' | (SEQ ID<br>NO: 133) |
| cp-asiMyD88#27-5(S):<br>5' UGUGACUUCCAGAC*C*A*cholesterol 3' | (SEQ ID<br>NO: 134) |
| cp-asiMyD88#27-5(AS):<br>5' UGGUCUGGAAGUCAmCmAU*U*C*C*U 3' | (SEQ ID<br>NO: 135) |
| cp-asiMyD88#27-6(S):<br>5' mUGmUGmACmUUmCCmAGmAC*mC*A*choles-<br>terol 3' | (SEQ ID<br>NO: 136) |
| cp-asiMyD88#27-6(AS):<br>5' UGGUCUGGAAGUCAU*U*C*C*U 3' | (SEQ ID<br>NO: 137) |
| cp-asiMyD88#27-7(S):<br>5' mUGmUGmACmUUmCCmAGmAC*mC*A*choles-<br>terol 3' | (SEQ ID<br>NO: 138) |
| cp-asiMyD88#27-7(AS):<br>5' UGGUCUGGAAGUCACAU*U*mC*mC*mU 3' | (SEQ ID<br>NO: 139) |
| cp-asiMyD88#27-8(S):<br>5' mUGmUGmACmUUmCCmAGmAC*mC*A*choles-<br>terol 3' | (SEQ ID<br>NO: 140) |
| cp-asiMyD88#27-8(AS):<br>5' UGGUCUGGAAGUCACAmU*mU*mC*mC*mU 3' | (SEQ ID<br>NO: 141) |
| cp-asiMyD88#27-9(S):<br>5' mUGmUGmACmUUmCCmAGmAC*mC*A*choles-<br>terol 3' | (SEQ ID<br>NO: 142) |
| cp-asiMyD88#27-9(AS):<br>5' UGGUCUGGAAGUCAmCmAmU*mU*C*C*U 3' | (SEQ ID<br>NO: 143) |
| cp-asiMyD88#27-10(S):<br>5' mUGmUGmACmUUmCCmAGmAC*mC*A*choles-<br>terol 3' | (SEQ ID<br>NO: 144) |
| cp-asiMyD88#27-10(AS):<br>5' UGGUCUGGAAGUCAmCmAU*U*C*C*U 3' | (SEQ ID<br>NO: 145) |

HeLa cells (ATCC) that had been cultured in Dulbecco's modified Eagle's medium (Gibco) containing 10% fetal bovine serum (Gibco) and 100 μg/ml penicillin/streptomycin in a 100 mm cell culture dish.

The potential cp-asiRNAs listed in Table 4 were incubated at 95° C. for 2 minutes and at 37° C. for 1 hour in OPTI-MEM buffer (Gibco). Proper strand annealing was confirmed via gel electrophoresis.

One day prior to transfection, $2.0 \times 10^4$ HeLa cells were seeded in 24-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media.

After 48 hours of asiRNA treatment, the level of MyD88 mRNA expression was determined.

Figure 6:
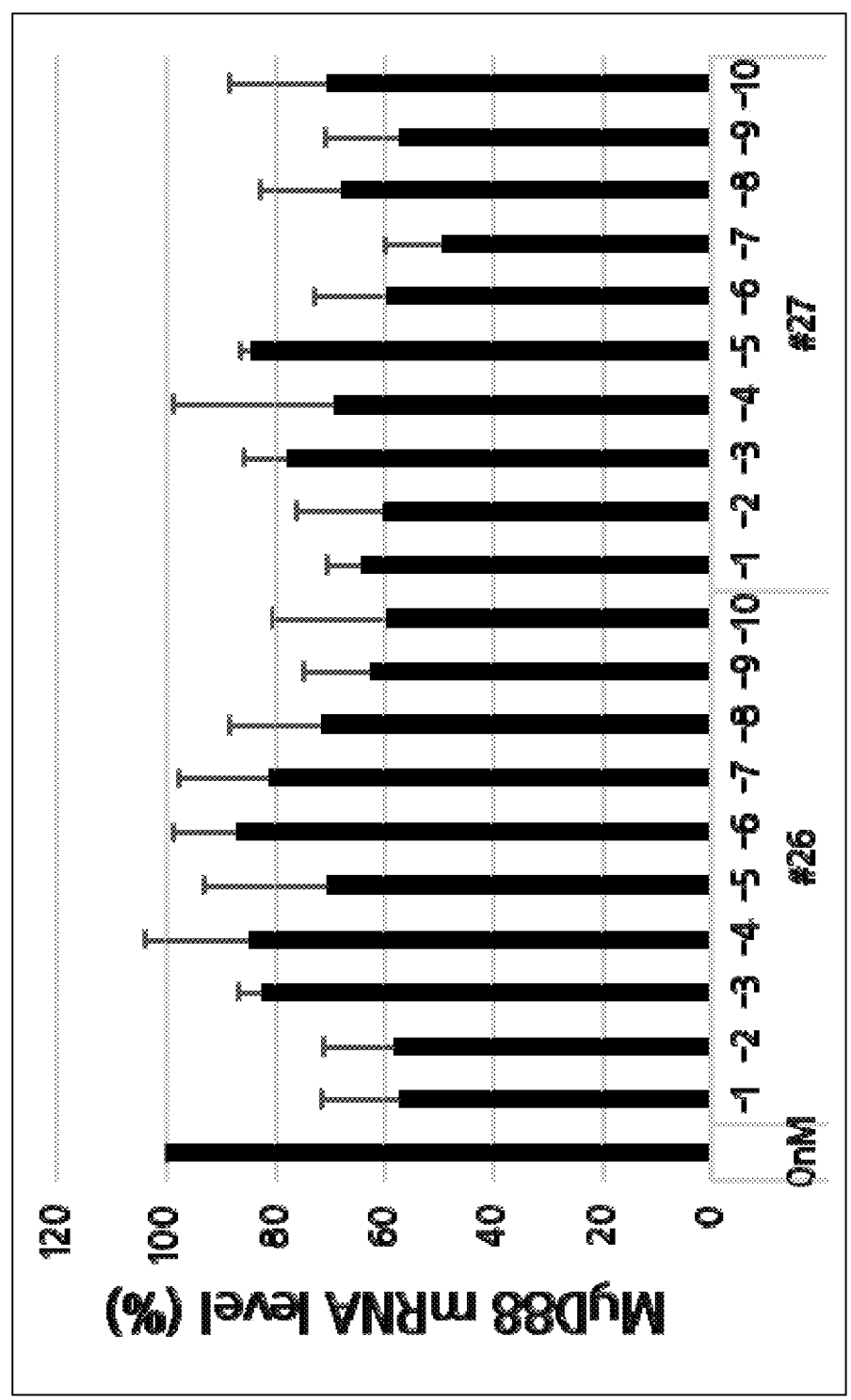
FIG. 6 shows the gene silencing efficiency of exemplary MyD88-targeting cell penetrating asiRNAs (cp-asiRNAs, or cp-asiMyD88s) to which various chemical modifications have been applied. The cp-asiRNAs were incubated without transfection vehicle in the presence of HeLa cells at a concentration of 1 μM and, after 48 hours, the degree of MyD88 mRNA expression was determined using real-time PCR. The mean and standard deviation of three repeat experiments are depicted.

The level of MyD88 inhibition by each of the 20 potential cp-asiRNAs is provided FIG. 6. Of the potential cp-asiRNAs tested, cp-asiRNA(26)-1 and cp-asiRNA(27)-7 exhibited the highest levels of MyD88 inhibition.

Example 7: Inhibition of MyD88 Protein Using MyD88-Specific Cp-asiRNAs

The efficacy of cp-asiRNAs for the inhibition of MyD88 protein was tested. Each potential cp-asiRNA was incubated with HeLa cells at 1 μM without a delivery vehicle and MyD88 protein levels were measured by western blot.

HeLa cells (ATCC) were used that had been cultured in Dulbecco's modified Eagle's medium (Gibco) containing 10% fetal bovine serum (Gibco) and 100 μg/ml penicillin/streptomycin in a 100 mm cell culture dish. The cp-asiRNAs were incubated at 95° C. for 2 minutes and at 37° C. for 1 hour in OPTI-MEM buffer (Gibco). Proper strand annealing was confirmed via gel electrophoresis. One day prior to transfection, $5.0 \times 10^4$ HeLa cells were seeded in 12-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media.

After 48 hours of asiRNA treatment, the level of MyD88 protein expression was determined via western blot. Briefly, the treated HeLa cells were lysed with RIPA buffer (GE). 30 μg of the total protein extract were loaded onto a 12% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-MyD88 antibody (Abcam) and anti-γ-tubulin (Bethyl). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The MyD88 and γ-tubulin bands were then imaged using a Chemidoc instrument (Bio-rad).

Figure 7:
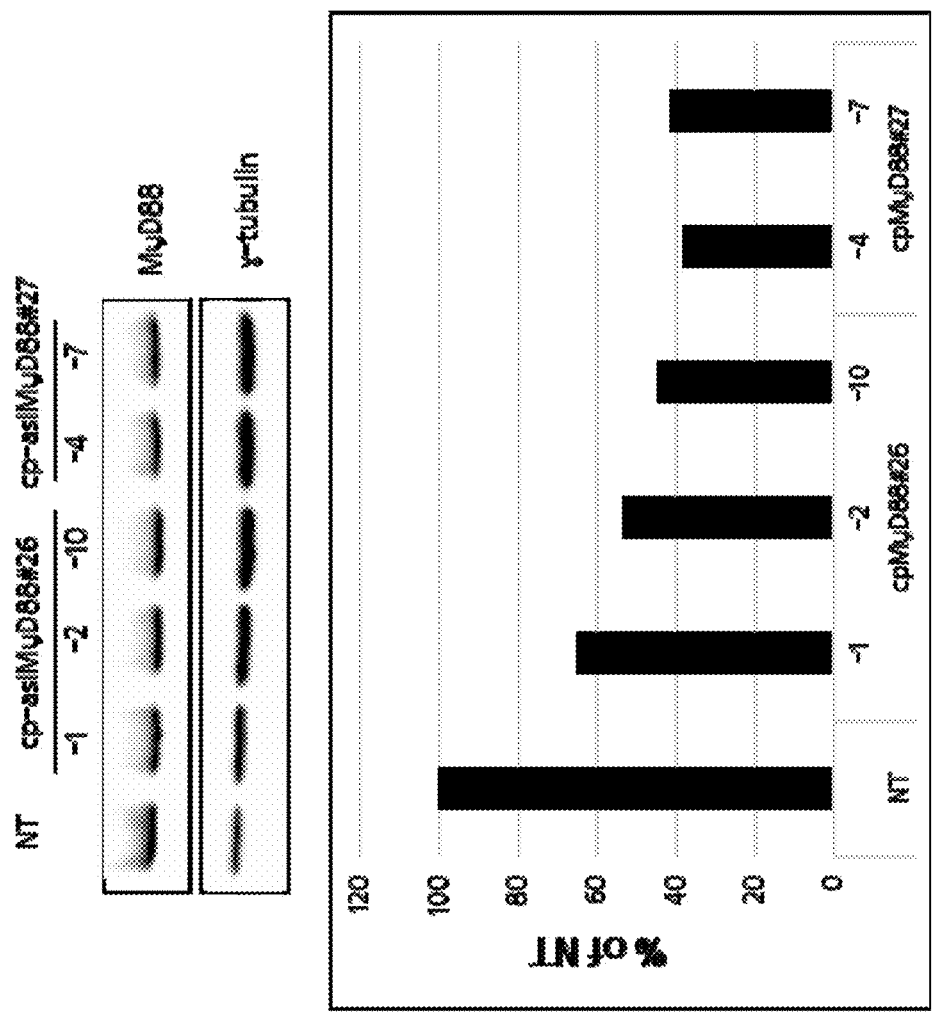
FIG. 7 shows the inhibition of MyD88 protein expression by exemplary cp-asiRNAs. The cp-asiRNAs were contacted to HeLa cells without transfection vehicle and, after 48 hours, protein was extracted and a western blot performed. (NT=no treatment).

The results of the western blot assay are depicted in FIG. 7. All cp-asiMyD88(27)-4 and cp-asiMyD88(27)-7 incubated cell lines exhibited 60% or more of MyD88 protein inhibition (FIG. 7).

Example 8: Inhibition of MyD88 Protein Using MyD88-Specific Cp-asiRNAs

A variety of potential cp-asiMyD88 structures having different number of phosphorothioate bond in antisense strand were synthesized and tested for their ability to inhibit MyD88 expression (Table 5).

TABLE 5

Additional cp-asiRNA sequences.
m = 2'-O-Methyl RNA, * = phosphorothioate bond.

| | |
|---|---|
| cp-asiMyD88#26-11(S):<br>5' GUGACUUCCAGACC*A*A*cholesterol 3' | (SEQ ID<br>NO: 146) |
| cp-asiMyD88#26-11(AS):<br>5' UUGGUCUGGAAGUCA*C*A*U*U*C*C 3' | (SEQ ID<br>NO: 147) |
| cp-asiMyD88#26-12(S):<br>5' GUGACUUCCAGACC*A*A*cholesterol 3' | (SEQ ID<br>NO: 148) |

TABLE 5-continued

Additional cp-asiRNA sequences.
m = 2'-O-Methyl RNA, * = phosphorothioate bond.

| | |
|---|---|
| cp-asiMyD88#26-12(AS):<br>5' UUGGUCUGGAAGUCA*C*mA*mU*mU*mC*mC 3' | (SEQ ID<br>NO: 149) |
| cp-asiMyD88#26-13(S):<br>5' GUGACUUCCAGACC*A*A*cholesterol 3' | (SEQ ID<br>NO: 150) |
| cp-asiMyD88#26-13(AS):<br>5' UUGGUCUGGAAGUCmA*mC*mA*mU*U*C*C 3' | (SEQ ID<br>NO: 151) |
| cp-asiMyD88#26-14(S):<br>5' GUGACUUCCAGACC*A*A*cholesterol 3' | (SEQ ID<br>NO: 152) |
| cp-asiMyD88#26-14(AS):<br>5' UUGGUCUGGAAGUCmA*mC*A*U*U*C*C 3' | (SEQ ID<br>NO: 153) |
| cp-asiMyD88#26-15(S):<br>5' mGUmGAmCUmUCmCAmGAmCC*mA*A*cholesterol 3' | (SEQ ID<br>NO: 154) |
| cp-asiMyD88#26-15(AS):<br>5' UUGGUCUGGAAGUCA*C*A*U*U*C*C 3' | (SEQ ID<br>NO: 155) |
| cp-asiMyD88#26-16(S):<br>5' mGUmGAmCUmUCmCAmGAmCC*mA*A*cholesterol 3' | (SEQ ID<br>NO: 156) |
| cp-asiMyD88#26-16(AS):<br>5' UUGGUCUGGAAGUCA*C*mA*mU*mU*mC*mC 3' | (SEQ ID<br>NO: 157) |
| cp-asiMyD88#26-17(S):<br>5' mGUmGAmCUmUCmCAmGAmCC*mA*A*cholesterol 3' | (SEQ ID<br>NO: 158) |
| cp-asiMyD88#26-17(AS):<br>5' UUGGUCUGGAAGUCmA*mC*mA*mU*U*C*C 3' | (SEQ ID<br>NO: 159) |
| cp-asiMyD88#26-18(S):<br>5' mGUmGAmCUmUCmCAmGAmCC*mA*A*cholesterol 3' | (SEQ ID<br>NO: 160) |
| cp-asiMyD88#26-18(AS):<br>5' UUGGUCUGGAAGUCmA*mC*A*U*U*C*C 3' | (SEQ ID<br>NO: 161) |
| cp-asiMyD88#27-11(S):<br>5' UGUGACUUCCAGAC*C*A*cholesterol 3' | (SEQ ID<br>NO: 162) |
| cp-asiMyD88#27-11(AS):<br>5' UGGUCUGGAAGUCAC*A*U*U*C*C*U 3' | (SEQ ID<br>NO: 163) |
| cp-asiMyD88#27-12(S):<br>5' UGUGACUUCCAGAC*C*A*cholesterol 3' | (SEQ ID<br>NO: 164) |
| cp-asiMyD88#27-12(AS):<br>5' UGGUCUGGAAGUCAmC*mA*mU*mU*C*C*U 3' | (SEQ ID<br>NO: 165) |
| cp-asiMyD88#27-13(S):<br>5' mUGmUGmACmUUmCCmAGmAC*mC*A*cholesterol 3' | (SEQ ID<br>NO: 166) |
| cp-asiMyD88#27-13(AS):<br>5' UGGUCUGGAAGUCAC*A*U*U*mC*mC*mU 3' | (SEQ ID<br>NO: 167) |
| cp-asiMyD88#27-14(S):<br>5' mUGmUGmACmUUmCCmAGmAC*mC*A*cholesterol 3' | (SEQ ID<br>NO: 168) |
| cp-asiMyD88#27-14(AS):<br>5' UGGUCUGGAAGUCAmC*mA*mU*mU*C*C*U 3' | (SEQ ID<br>NO: 169) |

The ability of 1 μM of each of the potential cp-asiRNAs listed in Table 5 to inhibit MyD88 mRNA in HeLa cells was tested. HeLa cells (ATCC) were used that had been cultured in Dulbecco's modified Eagle's medium (Gibco) containing 10% fetal bovine serum (Gibco) and 100 μg/ml penicillin/streptomycin in a 100 mm cell culture dish. The potential cp-asiRNAs listed in Table 5 were incubated at 95° C. for 2 minutes and at 37° C. for 1 hour in OPTI-MEM buffer (Gibco). Proper strand annealing was confirmed via gel electrophoresis. One day prior to transfection, $2.0 \times 10^4$ HeLa cells were seeded in 24-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media. After 48 hours of asiRNA treatment, the level of MyD88 mRNA expression was determined.

Figure 8:
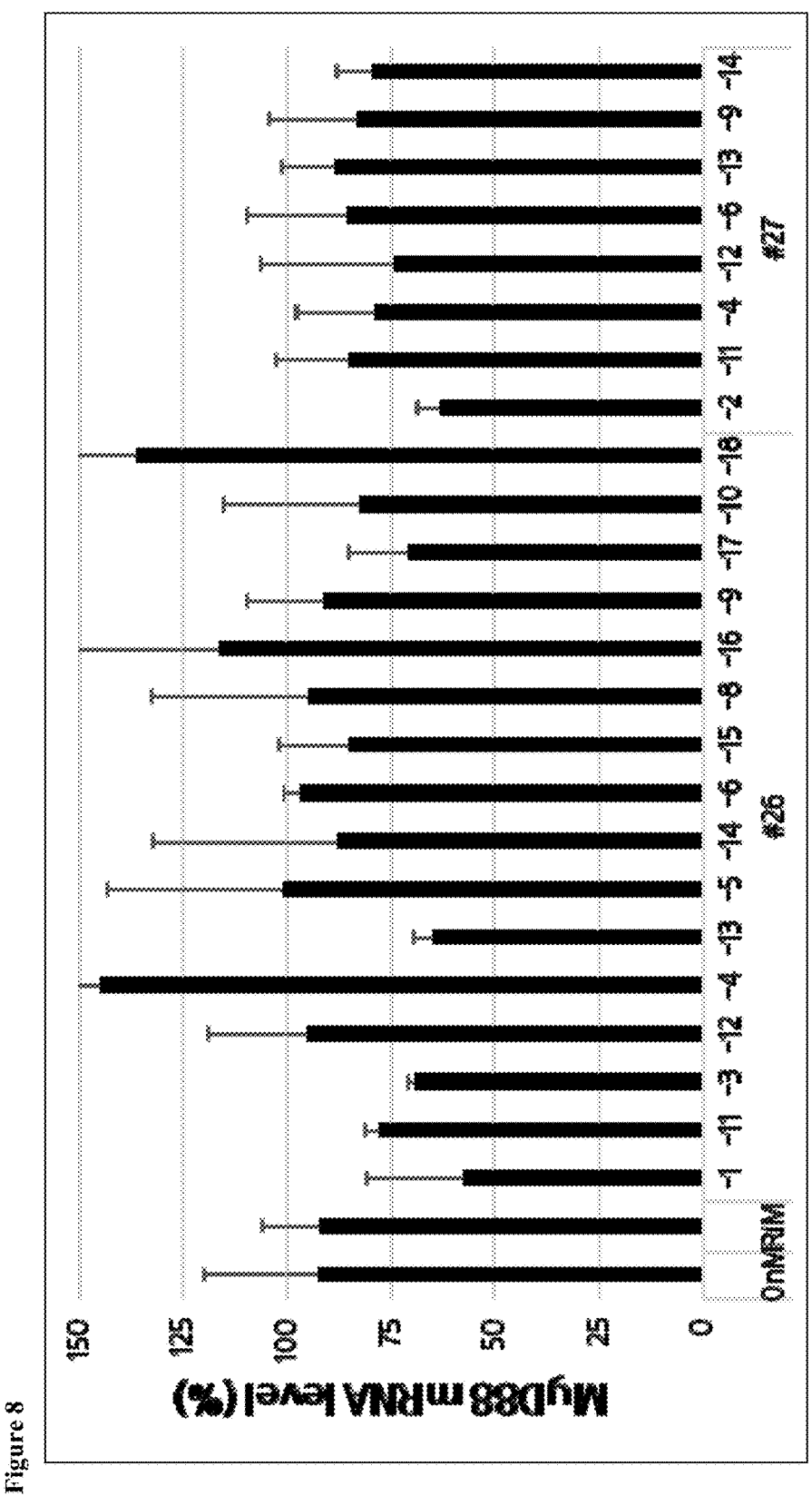
FIG. 8 shows the gene silencing efficiency of exemplary cp-asiRNAs to which various chemical modifications have been applied. The cp-asiRNAs were incubated without transfection vehicle in the presence of HeLa cells at a concentration of 1 μM and, after 48 hours, the degree of MyD88 mRNA expression was determined using real-time PCR. The mean and standard deviation of three repeat experiments are depicted.

As seen in FIG. 8, MyD88 mRNA potential cp-asiRNA (26) containing 3 phosphorothioate bond on sense strand and 4 phosphorothioate bond on antisense strand, cp-asiRNA (27) containing 3 phosphorothioate bond on sense strand and three 2'-O-Methylation and 4 phosphorothioate bond on antisense strand exhibited the highest levels of MyD88 inhibition.

Example 9: Inhibition of MyD88 Protein Using Additional MyD88-Specific Cp-asiRNAs The efficacy of cp-asiRNAs for the inhibition of MyD88 protein were tested. Each potential cp-asiRNA was incubated with HeLa cells at 3 uM without a delivery vehicle and MyD88 protein levels were measured by western blot. HeLa cells (ATCC) were used that had been cultured in Dulbecco's modified Eagle's medium (Gibco) containing 10% fetal bovine serum (Gibco) and 100 μg/ml penicillin/streptomycin in a 100 mm cell culture dish. The cp-asiRNAs were incubated at 95° C. for 2 minutes and at 37° C. for 1 hour in OPTI-MEM buffer (Gibco). Proper strand annealing was confirmed via gel electrophoresis. One day prior to transfection, $5.0 \times 10^4$ HeLa cells were seeded in 12-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media.

After 48 hours of asiRNA treatment, the level of MyD88 protein expression was determined via western blot. Briefly, the treated HeLa cells were lysed with RIPA buffer (GE). 30 μg of the total protein extract were loaded onto a 12% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-MyD88 antibody (Abcam) and anti-γ-tubulin (Bethyl). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The MyD88 and γ-tubulin bands were then imaged using a Chemidoc instrument (Bio-rad).

Figure 9:
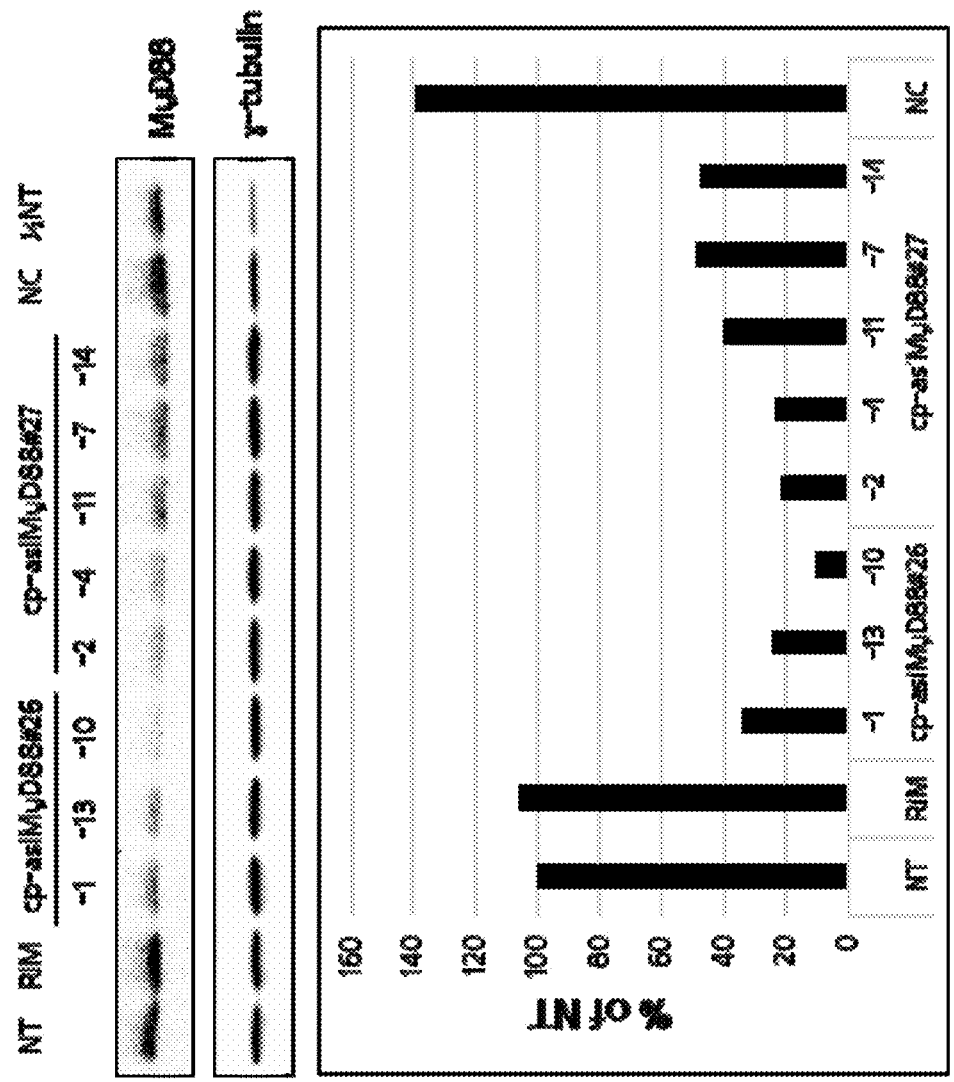
FIG. 9 shows the inhibition of MyD88 protein expression by exemplary cp-asiRNAs. The cp-asiRNAs were contacted to HeLa cells without transfection vehicle and, after 48 hours, protein was extracted and a western blot performed. (NT=no treatment, RiM=transfection reagent only, NC=negative control).

The results of the western blot assay are depicted in FIG. 9. All cp-asiMyD88 incubated cell lines exhibited 50% or more of MyD88 protein inhibition. In addition, the cp-asiMyD88(26)-10 and cp-asiMyD88(27)-2 were shown to have a higher efficiency in the MyD88 inhibition ability than other cp-asiMD88s (FIG. 9).

Example 10: Additional MyD88 cp-asiRNA Structures

A variety of potential cp-asiMyD88 structures having different strand lengths and numbers of 2'-O-methylation modifications and phosphorothioate bonds were synthesized and tested for their ability to inhibit MyD88 expression (Table 6).

TABLE 6

Additional cp-asiRNA sequences
(m= 2'-O-Methyl RNA,*= phosphorothioate bond).

| | |
|---|---|
| cp-asiMyD88#26-13(S):<br>5' GUGACUUCCAGACC*A*A*cholesterol 3' | (SEQ ID<br>NO: 170) |
| cp-asiMyD88#26-13(AS):<br>5' UUGGUCUGGAAGUCmA*mC*mA*mU*U*C*C 3' | (SEQ ID<br>NO: 171) |
| cp-asiMyD88#26-19(S):<br>5' GUGACUUCCAGACC*A*A*cholesterol 3' | (SEQ ID<br>NO: 172) |
| cp-asiMyD88#26-19(AS):<br>5' UUGGUCUGGAAGU*C*mA*mC*mA*mU*U 3' | (SEQ ID<br>NO: 173) |
| cp-asiMyD88#27-14(S):<br>5' mUGmUGmACmUUmCCmAGmAC*mC*A*cholesterol 3' | (SEQ ID<br>NO: 174) |
| cp-asiMyD88#27-14(AS):<br>5' UGGUCUGGAAGUCAmC*mA*mU*mU*C*C*U 3' | (SEQ ID<br>NO: 175) |
| cp-asiMyD88#27-15(S):<br>5' mUGmUGmACmUUmCCmAGmAC*mC*A*cholesterol 3' | (SEQ ID<br>NO: 176) |
| cp-asiMyD88#27-15(AS):<br>5' UGGUCUGGAAGUC*A*mC*mA*mU*mU*C 3' | (SEQ ID<br>NO: 177) |

The ability of 1 μM or 3 μM of each of the potential cp-asiRNAs listed in Table 6 to inhibit MyD88 mRNA in HeLa cells was tested. HeLa cells (ATCC) were used that had been cultured in Dulbecco's modified Eagle's medium (Gibco) containing 10% fetal bovine serum (Gibco) and 100 μg/ml penicillin/streptomycin in a 100 mm cell culture dish. The potential cp-asiRNAs listed in Table 6 were incubated at 95° C. for 2 minutes and at 37° C. for 1 hour in OPTI-MEM buffer (Gibco). Proper strand annealing was confirmed via gel electrophoresis. One day prior to transfection, $2.0 \times 10^4$ HeLa cells were seeded in 24-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media. After 48 hours of asiRNA treatment, the level of MyD88 mRNA expression was determined.

Figure 10:
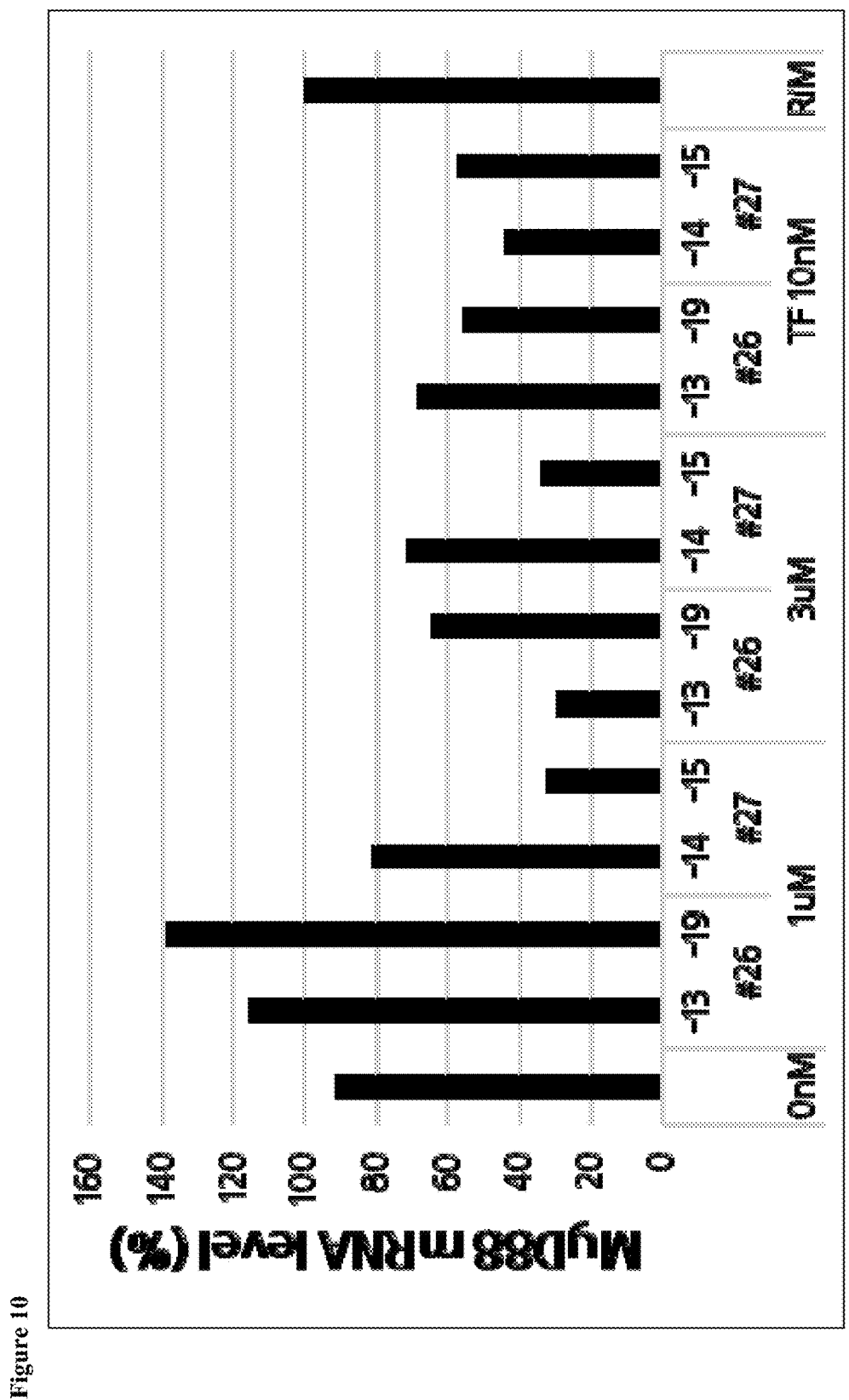
FIG. 10 shows the gene silencing efficiency of cp-asiRNAs having different antisense strand lengths (21 or 19 nucleotides) and containing 2'-O-Methylation modifications. Each cp-asiRNAs was incubated without transfection vehicle in the presence of HeLa cells at a concentration of 1 μM and, after 48 hours, the degree of MyD88 mRNA expression was determined using real-time PCR.

As seen in FIG. 10, MyD88 mRNA potential cp-asiRNA (26) containing four 2'-O-Methylation and six phosphorothioate bond on 21 nucleotide antisense strand, cp-asiRNA (27) containing four 2'-O-Methylation and six phosphorothioate bond on 19 nucleotide antisense strand exhibited the highest levels of MyD88 inhibition.

Example 11: Inhibition of MyD88 Protein Using Additional MyD88-Specific Cp-asiRNAs The efficacy of cp-asiRNAs for the inhibition of MyD88 protein were tested. Each potential cp-asiRNA was incubated with HeLa cells at 1 μM and 3 μM without a delivery vehicle and MyD88 protein levels were measured by western blot. HeLa cells (ATCC) were used that had been cultured in Dulbecco's modified Eagle's medium (Gibco) containing 10% fetal bovine serum (Gibco) and 100 μg/ml penicillin/streptomycin in a 100 mm cell culture dish. The cp-asiRNAs were incubated at 95° C. for 2 minutes and at 37° C. for 1 hour in OPTI-MEM buffer (Gibco). Proper strand annealing was confirmed via gel electrophoresis.

One day prior to transfection, $5.0 \times 10^4$ HeLa cells were seeded in 12-well plates. Immediately before treatment, the HeLa cells were washed with 1×DPBS (Gibco) then cultured in the presence of the potential cp-asiRNAs in OPTI-MEM buffer for 24 hours, at which point the asiRNA-containing OPTI-MEM media was replaced with a serum-containing media. After 48 hours of asiRNA treatment, the level of MyD88 protein expression was determined via western blot. Briefly, the treated HeLa cells were lysed with RIPA buffer (GE). 30 μg of the total protein extract were loaded onto a 12% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-MyD88 antibody (Abcam) and anti-γ-tubulin (Bethyl). The membrane was then washed with 1×TBST for 10 minutes three times and was incubated for 1 hour at the room temperature in 5% skim milk with HRP-conjugated secondary antibody. The membrane was washed with 1×TBST for 10 minutes and treated with 1×ECL for 1 minute. The MyD88 and γ-tubulin bands were then imaged using a Chemidoc instrument (Bio-rad).

Figure 11:
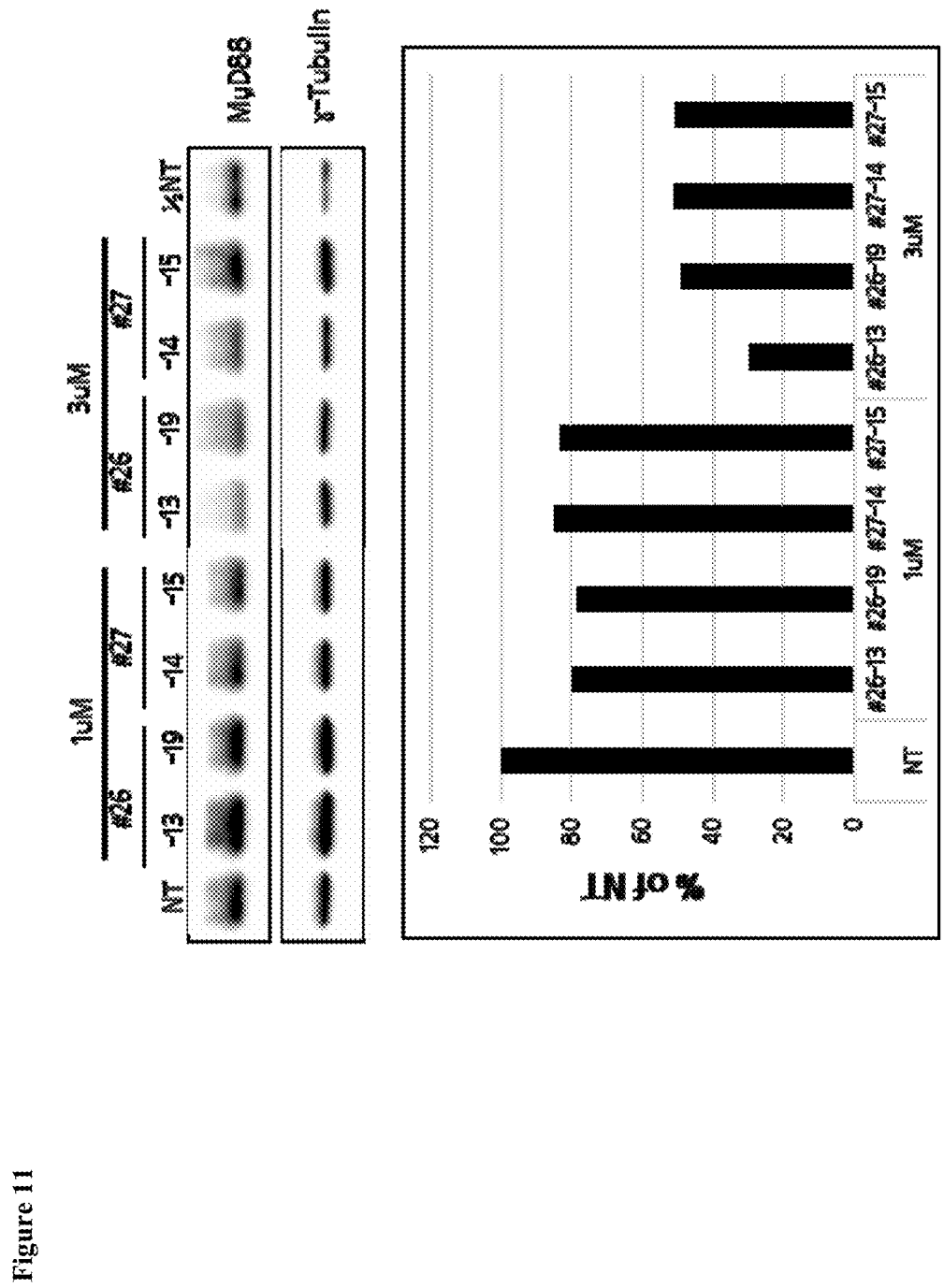
FIG. 11 shows the inhibition of MyD88 protein expression by exemplary cp-asiRNAs. The cp-asiRNAs were incubated without transfection vehicle in the presence of HeLa cells at a concentration of 1 uM or 3 uM and, after 48 hours, protein was extracted and a western blot performed. (NT=no treatment).

The results of the western blot assay are depicted in FIG. 11. All 3 μM cp-asiMyD88 incubated cell lines exhibited 50% or more of MyD88 protein inhibition. In addition, the cp-asiMyD88(26)-13 were shown to have a higher efficiency in the MyD88 inhibition ability than other cp-asiMD88s (FIG. 11).

Example 12: Screening for Toll-Like Receptor 3 Specific Asymmetric Small Interfering RNAs To identify asymmetric small interfering RNAs (asiR-NAs) that inhibit Toll-like receptor 3 with high efficiency, 100 asiRNAs were synthesized and screened. The nucleic acid sequences of the screened asiRNAs are provided in Table 7.

TABLE 7

Nucleic acid sequences for exemplary Toll-like receptor 3 targeting asiRNA.
TLR3 asiRNA Sequence

| Name | Sequence (5'-3') | SEQ ID NO: | Name | Sequence (5'-3') | SEQ ID NO: |
|---|---|---|---|---|---|
| TLR3asiRNA<br>S(1) | AUCUUUCCUA<br>CAACAA | 178 | TLR3asiRNA<br>AS(1) | UUGUUGUAGGAAA<br>GAUCGAGC | 179 |
| TLR3asiRNA<br>S(2) | UCUUUCCUAC<br>AACAAC | 180 | TLR3asiRNA<br>AS(2) | GUUGUUGUAGGAA<br>AGAUCGAG | 181 |

TABLE 7-continued

Nucleic acid sequences for exemplary Toll-like receptor 3 targeting asiRNA.
TLR3 asiRNA Sequence

| Name | Sequence (5'-3') | SEQ ID NO: | Name | Sequence (5'-3') | SEQ ID NO: |
|---|---|---|---|---|---|
| TLR3asiRNA S(3) | GGCCCUUAAA AAUGUG | 182 | TLR3asiRNA AS(3) | CACAUUUUUAAGG GCCACCCU | 183 |
| TLR3asiRNA S(4) | GCCCUUAAAAA UGUGG | 184 | TLR3asiRNA AS(4) | CCACAUUUUUAAG GGCCACCC | 185 |
| TLR3asiRNA S(5) | CCCUUAAAAAU GUGGA | 186 | TLR3asiRNA AS(5) | UCCACAUUUUUAA GGGCCACC | 187 |
| TLR3asiRNA S(6) | CCUUAAAAAUG UGGAU | 188 | TLR3asiRNA AS(6) | AUCCACAUUUUUA AGGGCCAC | 189 |
| TLR3asiRNA S(7) | CUUAAAAAUGU GGAUA | 190 | TLR3asiRNA AS(7) | UAUCCACAUUUUU AAGGGCCA | 191 |
| TLR3asiRNA S(8) | UCGUAACUUG ACCAUU | 192 | TLR3asiRNA AS(8) | AAUGGUCAAGUUA CGAAGAGG | 193 |
| TLR3asiRNA S(9) | CGUAACUUGA CCAUUC | 194 | TLR3asiRNA AS(9) | GAAUGGUCAAGUU ACGAAGAG | 195 |
| TLR3asiRNA S(10) | GUAACUUGAC CAUUCU | 196 | TLR3asiRNA AS(10) | AGAAUGGUCAAGU UACGAAGA | 197 |
| TLR3asiRNA S(11) | UAACUUGACCA UUCUG | 198 | TLR3asiRNA AS(11) | CAGAAUGGUCAAG UUACGAAG | 199 |
| TLR3asiRNA S(12) | AACUUGACCAU UCUGG | 200 | TLR3asiRNA AS(12) | CCAGAAUGGUCAA GUUACGAA | 201 |
| TLR3asiRNA S(13) | ACUUGACCAU UCUGGA | 202 | TLR3asiRNA AS(13) | UCCAGAAUGGUCA AGUUACGA | 203 |
| TLR3asiRNA S(14) | AACAACAACAU AGCCA | 204 | TLR3asiRNA AS(14) | UGGCUAUGUUGUU GUUGCUUA | 205 |
| TLR3asiRNA S(15) | ACAACAACAUA GCCAA | 206 | TLR3asiRNA AS(15) | UUGGCUAUGUUGU UGUUGCUU | 207 |
| TLR3asiRNA S(16) | CAACAACAUAG CCAAC | 208 | TLR3asiRNA AS(16) | GUUGGCUAUGUUG UUGUUGCU | 209 |
| TLR3asiRNA S(17) | AACAACAUAGC CAACA | 210 | TLR3asiRNA AS(17) | UGUUGGCUAUGUU GUUGUUGC | 211 |
| TLR3asiRNA S(18) | ACAACAUAGCC AACAU | 212 | TLR3asiRNA AS(18) | AUGUUGGCUAUGU UGUUGUUG | 213 |
| TLR3asiRNA S(19) | CAACAUAGCCA ACAUA | 214 | TLR3asiRNA AS(19) | UAUGUUGGCUAUG UUGUUGUU | 215 |
| TLR3asiRNA S(20) | AACAUAGCCAA CAUAA | 216 | TLR3asiRNA AS(20) | UUAUGUUGGCUAU GUUGUUGU | 217 |
| TLR3asiRNA S(21) | ACAUAGCCAAC AUAAA | 218 | TLR3asiRNA AS(21) | UUUAUGUUGGCUA UGUUGUUG | 219 |
| TLR3asiRNA S(22) | AUAGCCAACAU AAAUG | 220 | TLR3asiRNA AS(22) | CAUUUAUGUUGGC UAUGUUGU | 221 |
| TLR3asiRNA S(23) | UAGCCAACAUA AAUGA | 222 | TLR3asiRNA AS(23) | UCAUUUAUGUUGG CUAUGUUG | 223 |
| TLR3asiRNA S(24) | AAUCUCUCAAA UUUUG | 224 | TLR3asiRNA AS(24) | CAAAAUUUGAGAG AUUGGUCU | 225 |
| TLR3asiRNA S(25) | UGCACUCUGU UUGCGA | 226 | TLR3asiRNA AS(25) | UCGCAAACAGAGU GCAUGGU | 227 |
| TLR3asiRNA S(26) | GCACUCUGUU UGCGAA | 228 | TLR3asiRNA AS(26) | UUCGCAAACAGAG UGCAUGGU | 229 |
| TLR3asiRNA S(27) | CACUCUGUUU GCGAAG | 230 | TLR3asiRNA AS(27) | CUUCGCAAACAGA GUGCAUGG | 231 |

TABLE 7-continued

Nucleic acid sequences for exemplary Toll-like receptor 3 targeting asiRNA.
TLR3 asiRNA Sequence

| Name | Sequence (5'-3') | SEQ ID NO: | Name | Sequence (5'-3') | SEQ ID NO: |
| --- | --- | --- | --- | --- | --- |
| TLR3asiRNA S(28) | ACUCUGUUUG CGAAGA | 232 | TLR3asiRNA AS(28) | UCUUCGCAAACAG AGUGCAUG | 233 |
| TLR3asiRNA S(29) | CUCUGUUUGC GAAGAG | 234 | TLR3asiRNA AS(29) | CUCUUCGCAAACA GAGUGCAU | 235 |
| TLR3asiRNA S(30) | UCUGUUUGCG AAGAGG | 236 | TLR3asiRNA AS(30) | CCUCUUCGCAAAC AGAGUGCA | 237 |
| TLR3asiRNA S(31) | CUGUUUGCGA AGAGGA | 238 | TLR3asiRNA AS(31) | UCCUCUUCGCAAA CAGAGUGC | 239 |
| TLR3asiRNA S(32) | UGUUUGCGAA GAGGAA | 240 | TLR3asiRNA AS(32) | UUCCUCUUCGCAA ACAGAGUG | 241 |
| TLR3asiRNA S(33) | GUUUGCGAAG AGGAAU | 242 | TLR3asiRNA AS(33) | AUUCCUCUUCGCA AACAGAGU | 243 |
| TLR3asiRNA S(34) | UUUGCGAAGA GGAAUG | 244 | TLR3asiRNA AS(34) | CAUUCCUCUUCGC AAACAGAG | 245 |
| TLR3asiRNA S(35) | UUGCGAAGAG GAAUGU | 246 | TLR3asiRNA AS(35) | ACAUUCCUCUUCG CAAACAGA | 247 |
| TLR3asiRNA S(36) | UGCGAAGAGG AAUGUU | 248 | TLR3asiRNA AS(36) | AACAUUCCUCUUC GCAAACAG | 249 |
| TLR3asiRNA S(37) | GCGAAGAGGA AUGUUU | 250 | TLR3asiRNA AS(37) | AAACAUUCCUCUU CGCAAACA | 251 |
| TLR3asiRNA S(38) | CGAAGAGGAA UGUUUA | 252 | TLR3asiRNA AS(38) | UAAACAUUCCUCU UCGCAAAC | 253 |
| TLR3asiRNA S(39) | GAAGAGGAAU GUUUAA | 254 | TLR3asiRNA AS(39) | UUAAACAUUCCUC UUCGCAAA | 255 |
| TLR3asiRNA S(40) | AAGAGGAAUG UUUAAA | 256 | TLR3asiRNA AS(40) | UUUAAACAUUCCU CUUCGCAA | 257 |
| TLR3asiRNA S(41) | AGAGGAAUGU UUAAAU | 258 | TLR3asiRNA AS(41) | AUUUAAACAUUCC UCUUCGCA | 259 |
| TLR3asiRNA S(42) | GAGGAAUGUU UAAAUC | 260 | TLR3asiRNA AS(42) | GAUUUAAACAUUC CUCUUCGC | 261 |
| TLR3asiRNA S(43) | AGGAAUGUUU AAAUCU | 262 | TLR3asiRNA AS(43) | AGAUUUAAACAUU CCUCUUCG | 263 |
| TLR3asiRNA S(44) | GGAAUGUUUA AAUCUC | 264 | TLR3asiRNA AS(44) | GAGAUUUAAACAU UCCUCUUC | 265 |
| TLR3asiRNA S(45) | CUUGAACUGG CCAGUU | 266 | TLR3asiRNA AS(45) | AACUGGCCAGUUC AAGAUGCA | 267 |
| TLR3asiRNA S(46) | UUGAACUGGC CAGUUC | 268 | TLR3asiRNA AS(46) | GAACUGGCCAGUU CAAGAUGC | 269 |
| TLR3asiRNA S(47) | UGAACUGGCC AGUUCA | 270 | TLR3asiRNA AS(47) | UGAACUGGCCAGU UCAAGAUG | 271 |
| TLR3asiRNA S(48) | GAACUGGCCA GUUCAG | 272 | TLR3asiRNA AS(48) | CUGAACUGGCCAG UUCAAGAU | 273 |
| TLR3asiRNA S(49) | AACUGGCCAG UUCAGA | 274 | TLR3asiRNA AS(49) | UCUGAACUGGCCA GUUCAAGA | 275 |
| TLR3asiRNA S(50) | ACUGGCCAGU UCAGAA | 276 | TLR3asiRNA AS(50) | UUCUGAACUGGCC AGUUCAAG | 277 |
| TLR3asiRNA S(51) | CUGGCCAGUU CAGAAA | 278 | TLR3asiRNA AS(51) | UUUCUGAACUGGC CAGUUCAA | 279 |
| TLR3asiRNA S(52) | UGGCCAGUUC AGAAAG | 280 | TLR3asiRNA AS(52) | CUUUCUGAACUGG CCAGUUCA | 281 |

TABLE 7-continued

Nucleic acid sequences for exemplary Toll-like receptor 3 targeting asiRNA.
TLR3 asiRNA Sequence

| Name | Sequence (5'-3') | SEQ ID NO: | Name | Sequence (5'-3') | SEQ ID NO: |
|---|---|---|---|---|---|
| TLR3asiRNA S(53) | GGCCAGUUCA GAAAGA | 282 | TLR3asiRNA AS(53) | UCUUUCUGAACUG GCCAGUUC | 283 |
| TLR3asiRNA S(54) | GCCAGUUCAG AAAGAA | 284 | TLR3asiRNA AS(54) | UUCUUUCUGAACU GGCCAGUU | 285 |
| TLR3asiRNA S(55) | CCAGUUCAGA AAGAAC | 286 | TLR3asiRNA AS(55) | GUUCUUUCUGAAC UGGCCAGU | 287 |
| TLR3asiRNA S(56) | CAGUUCAGAAA GAACG | 288 | TLR3asiRNA AS(56) | CGUUCUUUCUGAA CUGGCCAG | 289 |
| TLR3asiRNA S(57) | AGUUCAGAAA GAACGG | 290 | TLR3asiRNA AS(57) | CCGUUCUUUCUGA ACUGGCCA | 291 |
| TLR3asiRNA S(58) | GUUCAGAAAG AACGGA | 292 | TLR3asiRNA AS(58) | UCCGUUCUUUCUG AACUGGCC | 293 |
| TLR3asiRNA S(59) | UUCAGAAAGAA CGGAU | 294 | TLR3asiRNA AS(59) | AUCCGUUCUUUCU GAACUGGC | 295 |
| TLR3asiRNA S(60) | UCAGAAAGAAC GGAUA | 296 | TLR3asiRNA AS(60) | UAUCCGUUCUUUC UGAACUGG | 297 |
| TLR3asiRNA S(61) | AAUUGCAAGUA GCACU | 298 | TLR3asiRNA AS(61) | AGUGCUACUUGCA AUUUAUGA | 299 |
| TLR3asiRNA S(62) | AUUGCAAGUA GCACUU | 300 | TLR3asiRNA AS(62) | AAGUGCUACUUGC AAUUUAUG | 301 |
| TLR3asiRNA S(63) | UUGCAAGUAG CACUUG | 302 | TLR3asiRNA AS(63) | CAAGUGCUACUUG CAAUUUAU | 303 |
| TLR3asiRNA S(64) | UGCAAGUAGC ACUUGG | 304 | TLR3asiRNA AS(64) | CCAAGUGCUACUU GCAAUUUA | 305 |
| TLR3asiRNA S(65) | GCAAGUAGCA CUUGGA | 306 | TLR3asiRNA AS(65) | UCCAAGUGCUACU UGCAAUUU | 307 |
| TLR3asiRNA S(66) | CAAGUAGCAC UUGGAU | 308 | TLR3asiRNA AS(66) | AUCCAAGUGCUAC UUGCAAUU | 309 |
| TLR3asiRNA S(67) | AAGUAGCACU UGGAUC | 310 | TLR3asiRNA AS(67) | GAUCCAAGUGCUA CUUGCAAU | 311 |
| TLR3asiRNA S(68) | UGCCCCCUUU GAACUC | 312 | TLR3asiRNA AS(68) | GAGUUCAAAGGGG GCACUGUC | 313 |
| TLR3asiRNA S(69) | UCUGGGAACA UUUCUC | 314 | TLR3asiRNA AS(69) | GAGAAAUGUUCCC AGACCCAA | 315 |
| TLR3asiRNA S(70) | CAGCAUCAAAA GAAGC | 316 | TLR3asiRNA AS(70) | GCUUCUUUUGAUG CUGUUAAC | 317 |
| TLR3asiRNA S(71) | CACGUGUGAA AGUAUU | 318 | TLR3asiRNA AS(71) | AAUACUUUCACAC GUGCAAUC | 319 |
| TLR3asiRNA S(72) | GUCUCACCUC CACAUC | 320 | TLR3asiRNA AS(72) | GAUGUGGAGGUGA GACAGACC | 321 |
| TLR3asiRNA S(73) | UGUCUCACCU CCACAU | 322 | TLR3asiRNA AS(73) | AUGUGGAGGUGAG ACAGACCC | 323 |
| TLR3asiRNA S(74) | AGAUUCAAGG UACAUC | 324 | TLR3asiRNA AS(74) | GAUGUACCUUGAA UCUUUUGC | 325 |
| TLR3asiRNA S(75) | GGAAACACGC AAACCC | 326 | TLR3asiRNA AS(75) | GGGUUUGCGUGUU UCCAGAGC | 327 |
| TLR3asiRNA S(76) | UGGAAACACG CAAACC | 328 | TLR3asiRNA AS(76) | GGUUUGCGUGUUU CCAGAGCC | 329 |
| TLR3asiRNA S(77) | UUGAGAAACUA GAAAU | 330 | TLR3asiRNA AS(77) | AUUUCUAGUUUCU CAAGACCC | 331 |

TABLE 7-continued

Nucleic acid sequences for exemplary Toll-like receptor 3 targeting asiRNA.
TLR3 asiRNA Sequence

| Name | Sequence (5'-3') | SEQ ID NO: | Name | Sequence (5'-3') | SEQ ID NO: |
|---|---|---|---|---|---|
| TLR3asiRNA S(78) | CUUGAGAAACUAGAAA | 332 | TLR3asiRNA AS(78) | UUUCUAGUUUCUCAAGACCCU | 333 |
| TLR3asiRNA S(79) | AACAUCCGUUGAGAAG | 334 | TLR3asiRNA AS(79) | CUUCUCAACGGAUGUUAUGAG | 335 |
| TLR3asiRNA S(80) | GUGCCCCCUUUGAACU | 336 | TLR3asiRNA AS(80) | AGUUCAAAGGGGCACUGUCU | 337 |
| TLR3asiRNA S(81) | AGUGCCCCCUUUGAAC | 338 | TLR3asiRNA AS(81) | GUUCAAAGGGGCACUGUCUU | 339 |
| TLR3asiRNA S(82) | CAGUGCCCCCUUUGAA | 340 | TLR3asiRNA AS(82) | UUCAAAGGGGCACUGUCUUU | 341 |
| TLR3asiRNA S(83) | GGAGGAUAUCUUUUUA | 342 | TLR3asiRNA AS(83) | UAAAAAGAUAUCCUCCAGCCC | 343 |
| TLR3asiRNA S(84) | UGGAGGAUAUCUUUUU | 344 | TLR3asiRNA AS(84) | AAAAAGAUAUCCUCCAGCCCU | 345 |
| TLR3asiRNA S(85) | ACUGAACCAUGCACUC | 346 | TLR3asiRNA AS(85) | GAGUGCAUGGUUCAGUUUAUA | 347 |
| TLR3asiRNA S(86) | UGAACCAUGCACUCUG | 348 | TLR3asiRNA AS(86) | CAGAGUGCAUGGUUCAGUUUA | 349 |
| TLR3asiRNA S(87) | GAACCAUGCACUCUGU | 350 | TLR3asiRNA AS(87) | ACAGAGUGCAUGGUUCAGUUU | 351 |
| TLR3asiRNA S(88) | AACCAUGCACUCUGUU | 352 | TLR3asiRNA AS(88) | AACAGAGUGCAUGGUUCAGUU | 353 |
| TLR3asiRNA S(89) | ACCAUGCACUCUGUUU | 354 | TLR3asiRNA AS(89) | AAACAGAGUGCAUGGUUCAGU | 355 |
| TLR3asiRNA S(90) | CCAUGCACUCUGUUUG | 356 | TLR3asiRNA AS(90) | CAAACAGAGUGCAUGGUUCAG | 357 |
| TLR3asiRNA S(91) | CAUGCACUCUGUUUGC | 358 | TLR3asiRNA AS(91) | GCAAACAGAGUGCAUGGUUCA | 359 |
| TLR3asiRNA S(92) | CUGCAUCUUGAACUGG | 360 | TLR3asiRNA AS(92) | CCAGUUCAAGAUGCAGUGAGA | 361 |
| TLR3asiRNA S(93) | ACUGCAUCUUGAACUG | 362 | TLR3asiRNA AS(93) | CAGUUCAAGAUGCAGUGAGAU | 363 |
| TLR3asiRNA S(94) | CACUGCAUCUUGAACU | 364 | TLR3asiRNA AS(94) | AGUUCAAGAUGCAGUGAGAUU | 365 |
| TLR3asiRNA S(95) | UCACUGCAUCUUGAAC | 366 | TLR3asiRNA AS(95) | GUUCAAGAUGCAGUGAGAUUU | 367 |
| TLR3asiRNA S(96) | UAAAUUGCAAGUAGCA | 368 | TLR3asiRNA AS(96) | UGCUACUUGCAAUUUAUGACG | 369 |
| TLR3asiRNA S(97) | AUAAAUUGCAAGUAGC | 370 | TLR3asiRNA AS(97) | GCUACUUGCAAUUUAUGACGA | 371 |
| TLR3asiRNA S(98) | CGUCAUAAAUUGCAAG | 372 | TLR3asiRNA AS(98) | CUUGCAAUUUAUGACGAAAGG | 373 |
| TLR3asiRNA S(99) | UCGUCAUAAAUUGCAA | 374 | TLR3asiRNA AS(99) | UUGCAAUUUAUGACGAAAGGC | 375 |
| TLR3asiRNA S(100) | UUCGUCAUAAAUUGCA | 376 | TLR3asiRNA AS(100) | UGCAAUUUAUGACGAAAGGCA | 377 |

The asiRNAs listed in Table 7 were incubated at 95° C. for 2 minutes and at 37° C. for 1 hour in annealing buffer (Bioneer Inc. Korea). Proper strand annealing was confirmed via gel electrophoresis using UV transilluminator. For the screen, 5×10³ HaCaT cells (ATCC) that had been cultured in Dulbecco's modified Eagle's medium (DMEM, Gibco) containing 10% fetal bovine serum (FBS, Gibco) and 100 units/ml Penicillin and 100 µg/ml Streptomycin in a 100 mm cell culture dish were seeded in 96 well plates. The HaCaT cells were transfected with 0.1 nM of the asiRNAs using RNAiMAX (Invitrogen Inc.) according to the manufacturer's instructions. The TLR3 mRNA levels in the transfected cells were measured 24 hours after transfection using qRT-PCR. Specifically, total RNA were extracted using TOYOBO lysis reagent and then ⅕ volume of the reaction mixture was used for cDNA synthesis using the TOYOBO RT reagent (TOYOBO SuperPrep). The synthesized cDNA was diluted and then quantitative RT-PCR was performed using THUNDERBIRD® Probe qPCR Mix (TOYOBO). Amplification of the target gene was detected using TLR3 TaqMan® Probe (Hs01551078_ml) and 18S TaqMan® Probe (Hs03928985_1).

Figure 12:
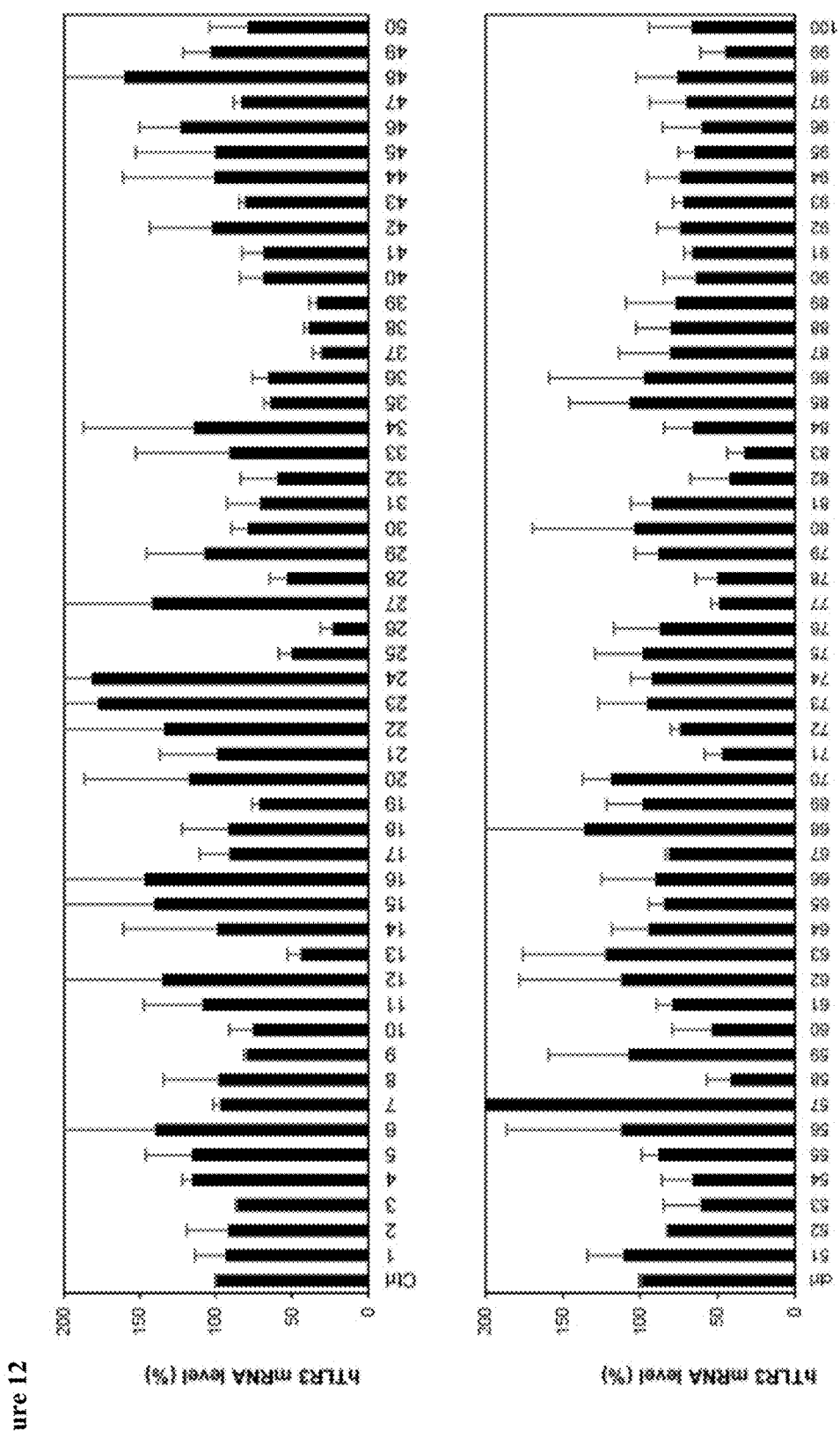
FIG. 12 shows the gene silencing efficiency of exemplary asiRNAs that target Toll-like receptor 3 (TLR3). The asiRNAs were transfected into HaCaT cells at a concentration of 0.1 nM, and, after 24 hours, the degree of TLR3 mRNA expression was determined using qRT-PCR. The mean and standard deviation of two repeat experiments are depicted.

The expression level of TLR3 inhibition by each of the 100 asiRNAs is provided in FIG. 12. 17 of the asiRNA sequences, asiRNA (13), asiRNA (25), asiRNA (26), asiRNA (28), asiRNA (32), asiRNA (33), asiRNA (37), asiRNA (38), asiRNA (39), asiRNA (53), asiRNA (58), asiRNA (60), asiRNA (71), asiRNA (77), asiRNA (78), asiRNA (82) and asiRNA (83), were selected for use in follow-up studies.

Example 13: Chemical Modification of asiRNAs for Self-Delivery

Figure 13:
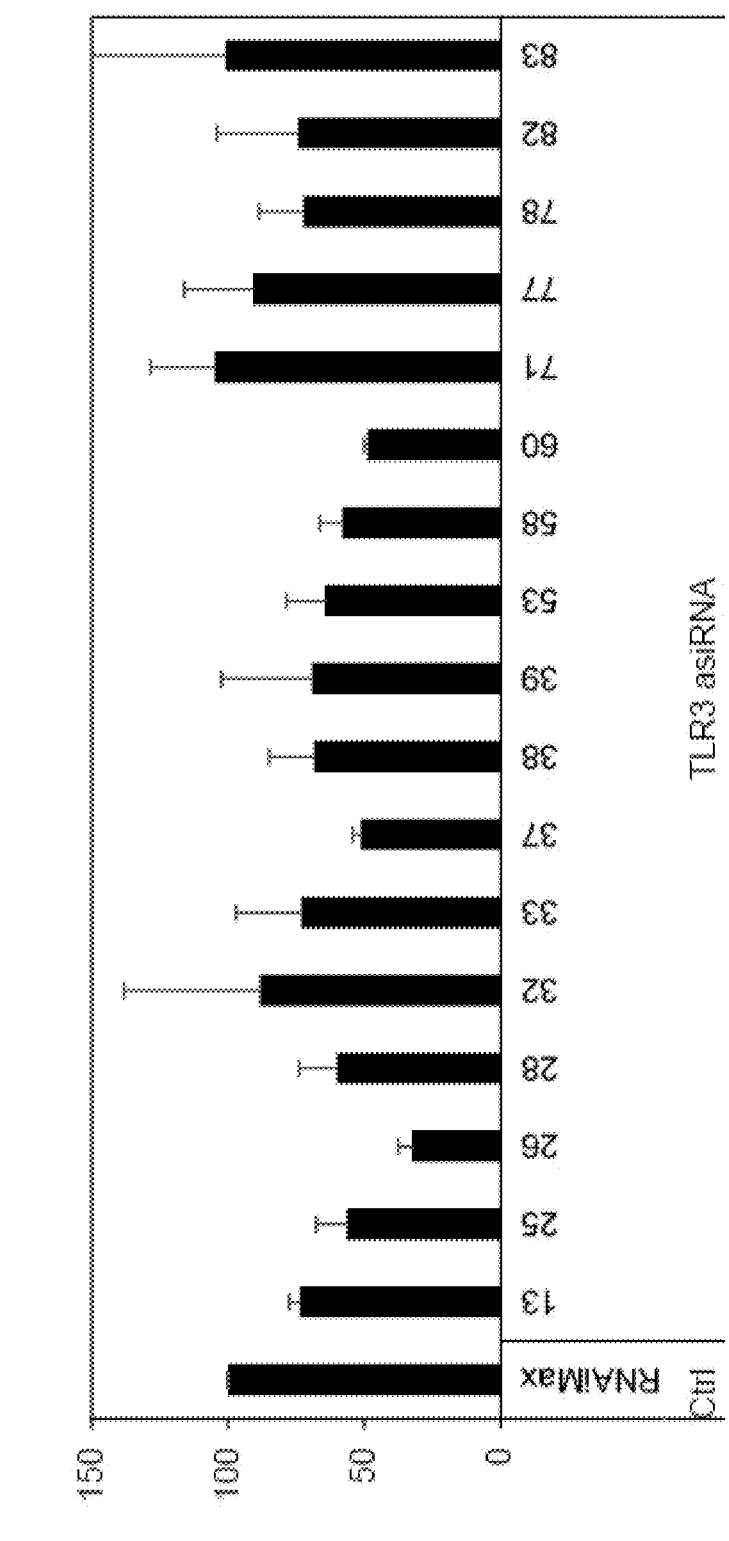
FIG. 13 shows the gene silencing efficiency of exemplary asiRNAs that target TLR3. The asiRNAs were transfected into HaCaT cells at a concentration of 0.1 nM and, after 24 hours, the degree of TLR3 mRNA expression was determined using qRT-PCR. The mean and standard deviation of two repeat experiments are depicted.
Figure 14:
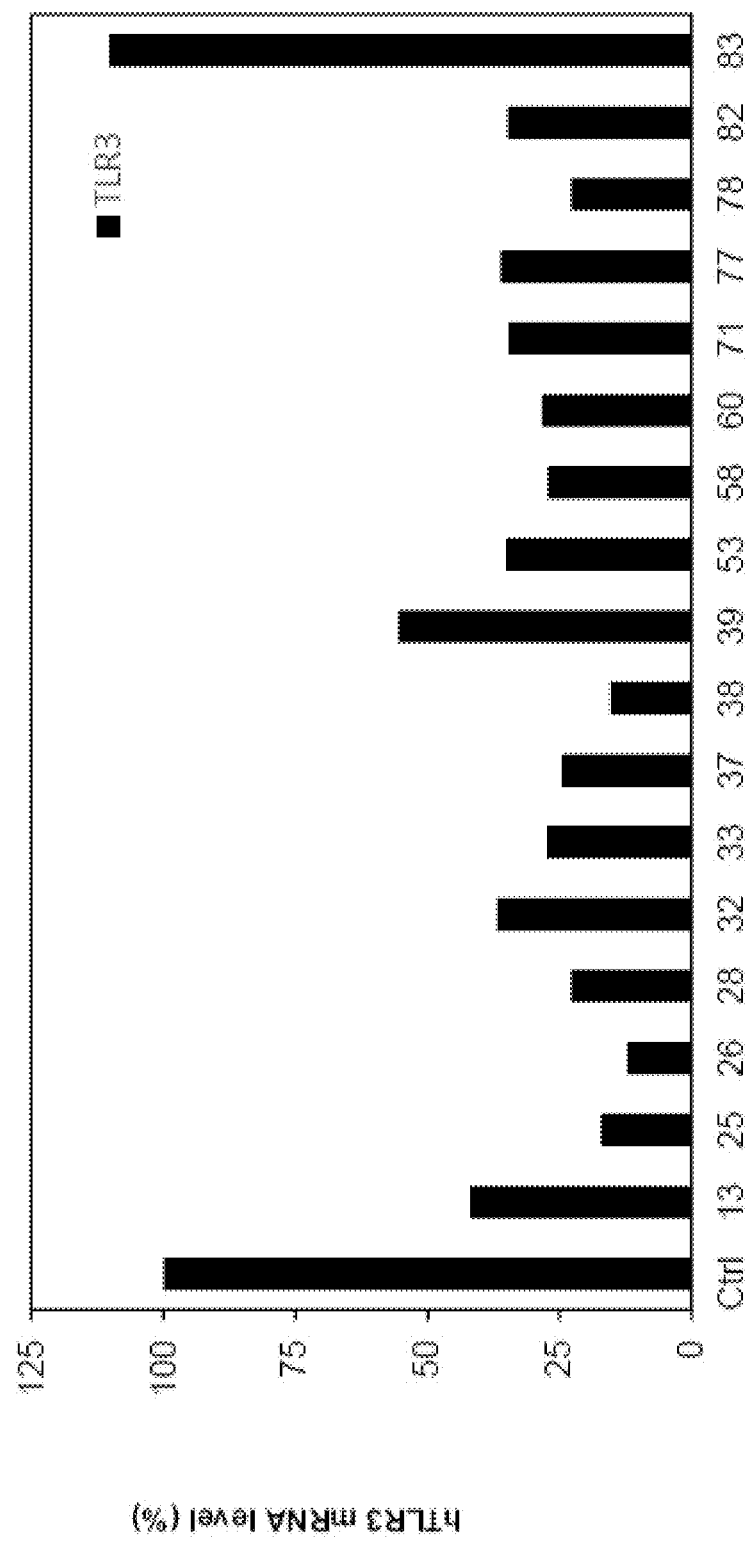
FIG. 14 shows the gene silencing efficiency of exemplary asiRNAs that target TLR3. The asiRNAs were transfected into HaCaT cells at a concentration of 0.3 nM and, after 24 hours, the degree of TLR3 mRNA expression was measured using qRT-PCR.
Figure 15:
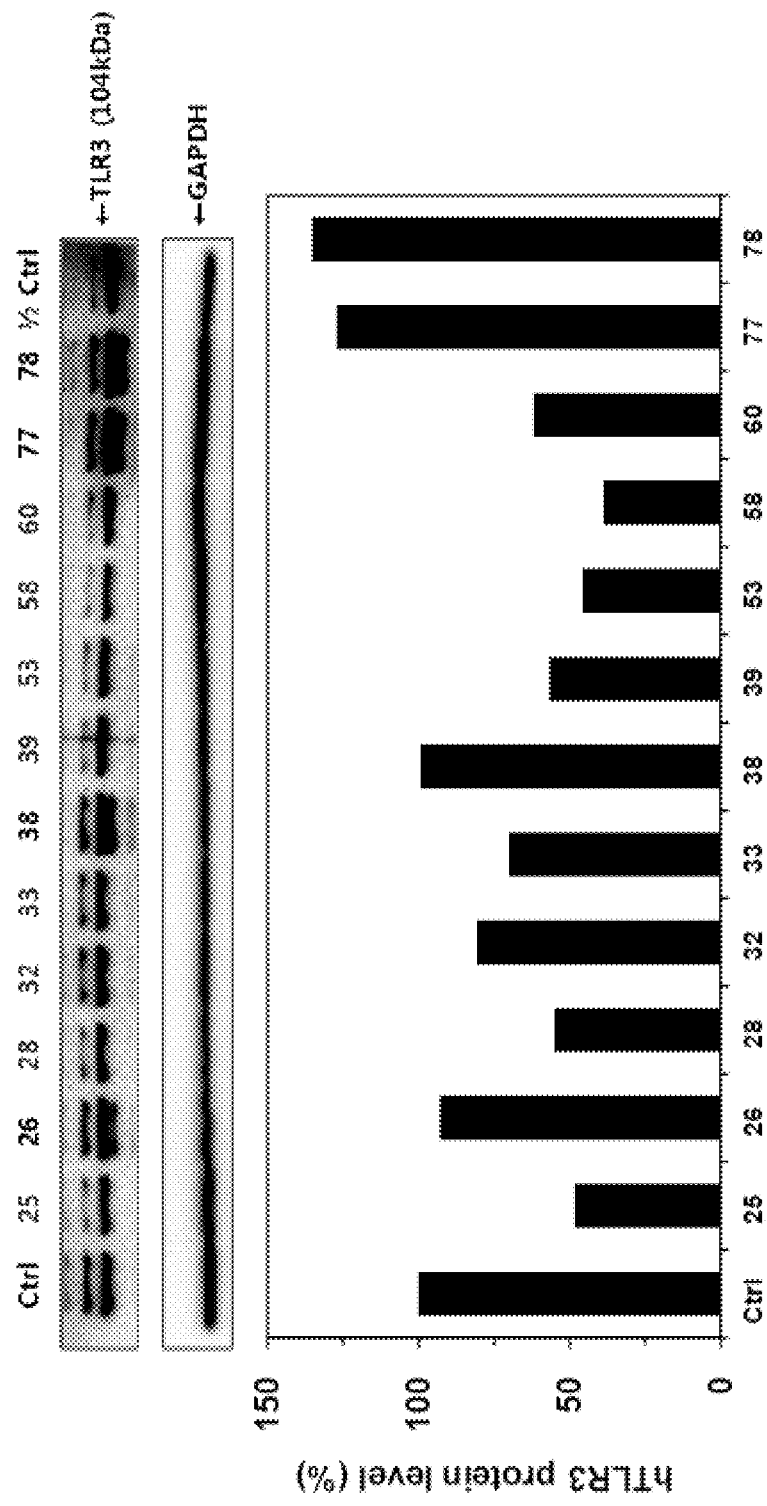
FIG. 15 shows the inhibition of TLR3 protein expression by exemplary asiRNAs. The asiRNAs were transfected into HaCaT cells at a concentration of 10 nM and, after 48 hours, the degree of TLR3 protein expression was determined using western blot.
Figure 16:
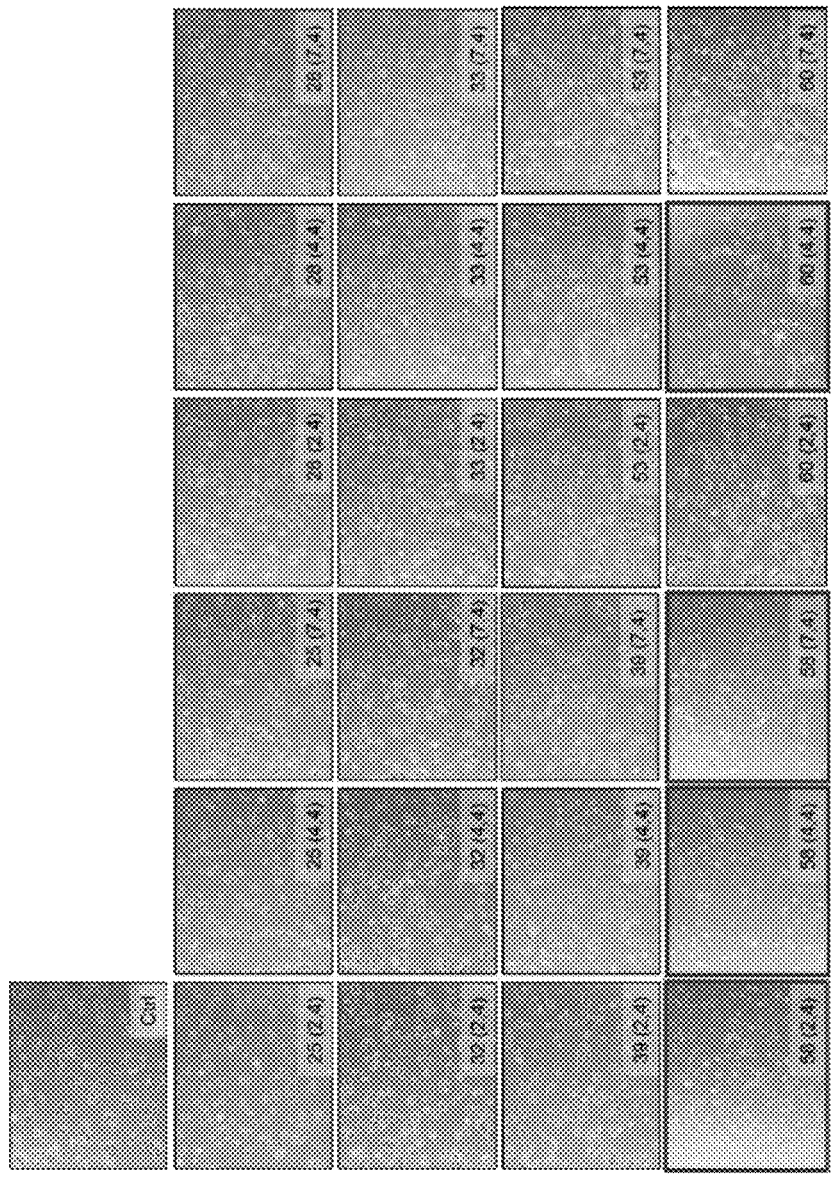
FIG. 16 shows images of HaCaT cells treated by exemplary cp-asiRNAs for 24 hours. The cp-asiRNAs were incubation of 1 uM and, after 24 hours, the morphology of the HaCaT cells was imaged by ECLIPSE 100 (Nikon).

Chemical modifications were applied to the asiRNAs selected in Example 12 and the cellular delivery of the modified asiRNAs was tested in the absence of other delivery vehicle. As described below, certain of the modifications improved endocytosis and stability of asiRNAs. Such cell penetrating asiRNAs (cp-asiRNAs) are able to be delivered into the cell in the absence of a delivery vehicle. The expression of TLR3 mRNA by the cells is provided in FIGS. 13 and 14 and the TLR3 protein levels are provided in FIG. 15, as determined using methods described above. The morphology of the cells is depicted in FIG. 16.

Potential cp-asiRNA (Table 8) were screened for Toll-like receptor 3 (TLR3) mRNA inhibition in HaCaT cells. Each potential cp-asiRNA was incubated with HaCaT cells, human skin keratinocyte cell line, at 1 µM and 3 µM without a delivery vehicle and TLR3 expression levels were measured by qRT-PCR and western blot study.

TABLE 8

Modified asiRNA sequences tested for self-delivery and TLR3 inhibition.
(m = 2'-O-Methyl RNA. * = phosphorothioate bond).

| Name | Sense(5' to 3') | SEQ ID NO: |
|---|---|---|
| TLR3cp-asiRNA S 25 | mUGmCAmCUmCUmGUmUUmGC*mG*A*cholesterol | 378 |
| TLR3cp-asiRNA AS 25(2,4) | UCGCAAACAGAGUGmCmAU*G*G*U*U | 379 |
| TLR3cp-asiRNA AS 25(4,4) | UCGCAAACAGAGUGmCmAmU*mG*G*U*U | 380 |
| TLR3cp-asiRNA AS 25(7,4) | UCGCAAACAGAGUGmCmAmU*mG*mG*mU*mU | 381 |
| TLR3cp-asiRNA S 28 | mACmUCmUGmUUmUGmCGmAA*mG*A*cholesterol | 382 |
| TLR3cp-asi RNA AS 28(2,4) | UCUUCGCAAACAGAmGmUG*C*A*U*G | 383 |
| TLR3cp-asiRNA AS 28(4,4) | UCUUCGCAAACAGAmGmUmG*mC*A*U*G | 384 |
| TLR3cp-asiRNA AS 28(7,4) | UCUUCGCAAACAGAmGmUmG*mC*mA*mU*mG | 385 |
| TLR3cp-asiRNA S 32 | mUGmUUmUGmCGmAAmGAmGG*mA*A*cholesterol | 386 |
| TLR3cp-asiRNA AS 32(2,4) | UUCCUCUUCGCAAAmCmAG*A*G*U*G | 387 |
| TLR3cp-asiRNA AS 32(4,4) | UUCCUCUUCGCAAAmCmAmG*mA*G*U*G | 388 |
| TLR3cp-asiRNA AS 32(7,4) | UUCCUCUUCGCAAAmCmAmG*mA*mG*mU*mG | 389 |
| TLR3cp-asiRNA S 33 | mGUmUUmGCmGAmAGmAGmGA*mA*U*cholesterol | 390 |
| TLR3cp-asiRNA AS 33(2,4) | AUUCCUCUUCGCAAmAmCA*G*A*G*U | 391 |
| TLR3cp-asiRNA AS 33(4,4) | AUUCCUCUUCGCAAmAmCmA*mG*A*G*U | 392 |
| TLR3cp-asiRNA AS 33(7,4) | AUUCCUCUUCGCAAmAmCmA*mG*mA*mG*mU | 393 |
| TLR3cp-asiRNA S 39 | mGAmAGmAGmGAmAUmGUmUU*mA*A*cholesterol | 394 |
| TLR3cp-asiRNA AS 39(2,4) | UUAAACAUUCCUCUmUmCG*C*A*A*A | 395 |
| TLR3cp-asiRNA AS 39(4,4) | UUAAACAUUCCUCUmUmCmG*mC*A*A*A | 396 |
| TLR3cp-asiRNA AS 39(7,4) | UUAAACAUUCCUCUmUmCmG*mC*mA*mA*mA | 397 |
| TLR3cp-asiRNA S 53 | mGGmCCmAGmUUmCAmGAmAA*mG*A*cholesterol | 398 |

TABLE 8-continued

Modified asiRNA sequences tested for
self-delivery and TLR3 inhibition.
(m = 2'-O-Methyl RNA. * = phosphorothioate bond).

| Name | Sense(5' to 3') | SEQ ID NO: |
|---|---|---|
| TLR3cp-asiRNA AS 53(2,4) | UCUUUCUGAACUGGmCmCA*G*U*U*C | 399 |
| TLR3cp-asiRNA AS 53(4,4) | UCUUUCUGAACUGGmCmCmA*mG*U*U*C | 400 |
| TLR3cp-asiRNA AS 53(7,4) | UCUUUCUGAACUGGmCmCmA*mG*mU*mU*mC | 401 |
| TLR3cp-asiRNA S 58 | mGUmUCmAGmAAmAGmAAmCG*mG*A*cholesterol | 402 |
| TLR3cp-asiRNA AS 58(2,4) | UCCGUUCUUUCUGAmAmCU*G*G*C*C | 403 |
| TLR3cp-asiRNA AS 58(4,4) | UCCGUUCUUUCUGAmAmCmU*mG*G*C*C | 404 |
| TLR3cp-asiRNA AS 58(7,4) | UCCGUUCUUUCUGAmAmCmU*mG*mG*mC*mC | 405 |
| TLR3cp-asiRNA S 60 | mUCmAGmAAmAGmAAmCGmGA*mU*A*cholesterol | 406 |
| TLR3cp-asiRNA AS 60(2,4) | UAUCCGUUCUUUCUmGmAA*C*U*G*G | 407 |
| TLR3cp-asiRNA AS 60(4,4) | UAUCCGUUCUUUCUmGmAmA*mC*U*G*G | 408 |
| TLR3cp-asiRNA AS 60(7,4) | UAUCCGUUCUUUCUmGmAmA*mC*mU*mG*mG | 409 |

HaCaT cells (ATCC) were cultured in Dulbecco's modified Eagle's medium (DMEM, Gibco) containing 10% fetal bovine serum (FBS, Gibco) and 100 units/ml Penicillin 100 μg/ml Streptomycin in a 100 mm cell culture dish. The potential cp-asiRNAs listed in Table 8 were incubated at 95° C. for 2 minutes and at 37° C. for 1 hour in Opti-MEM (Gibco). Proper strand annealing of the potential cp-asiRNAs was confirmed by gel electrophoresis.

On that day cp-asiRNAs treatment, 5×10⁴ cells were seeded into 24 well plates and then cultured in the presence of the potential cp-asiRNAs in Opti-MEM for 24 hours, at which point the cp-asiRNA-containing Opti-MEM media was replaced with a serum-containing media. Twenty-four hours later, TLR3 mRNA levels in HaCaT cells were determined using qRT-PCR. Specifically, total RNA were extracted using RNAiPlus® (TaKaRa) and then 500 ng of the reaction mixture was used for cDNA synthesis using the High-capacity cDNA reverse transcription kit (Applied Biosystems). The synthesized cDNA was diluted and then quantitative RT-PCR was performed using power SYBR green PCR master Mix (Applied Biosystems). The following primer sequences were used:

After 48 hours of cp-asiRNAs incubation, the level of TLR3 protein expression was determined via western blot. Briefly, the treated HaCaT cells were lysed with Mammalian protein Extraction Buffer (GE Healthcare). 10 μg of the total protein extract were loaded onto an 8% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-TLR3 antibody (Abcam) and anti-γ-tubulin antibody (Bethyl). The membrane was then washed with TBST for 10 minutes three times and was incubated for 1 hour at the room temperature in 5% skim milk with HRP-conjugated secondary antibody (Santa Cruz). The membrane was washed with TBST for 10 minutes and treated with ECL substrate (Thermo scientific). The Target protein bands were then imaged using a Chemi-doc instrument (Bio-rad).

Figure 17:
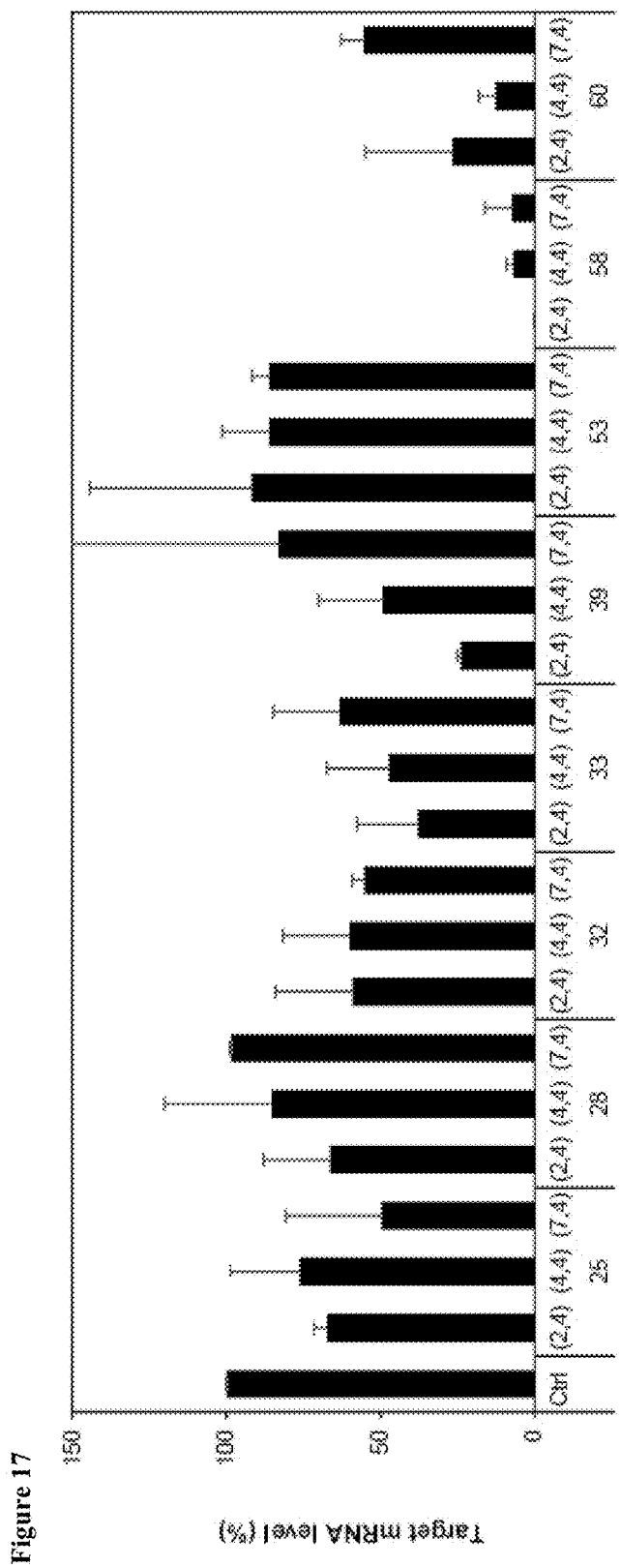
FIG. 17 shows the gene silencing efficiency of exemplary TLR3-targeting cell penetrating asiRNAs (cp-asiRNA, or cp-asiTLR3s) to which various chemical modifications have been applied. The cp-asiRNAs at a concentration of 1 μM were incubated with HaCaT cells and, after 48 hours, the degree of TLR3 mRNA expression was measured using qRT-PCR. The mean and standard deviation of two repeat experiments are depicted.
Figure 18:
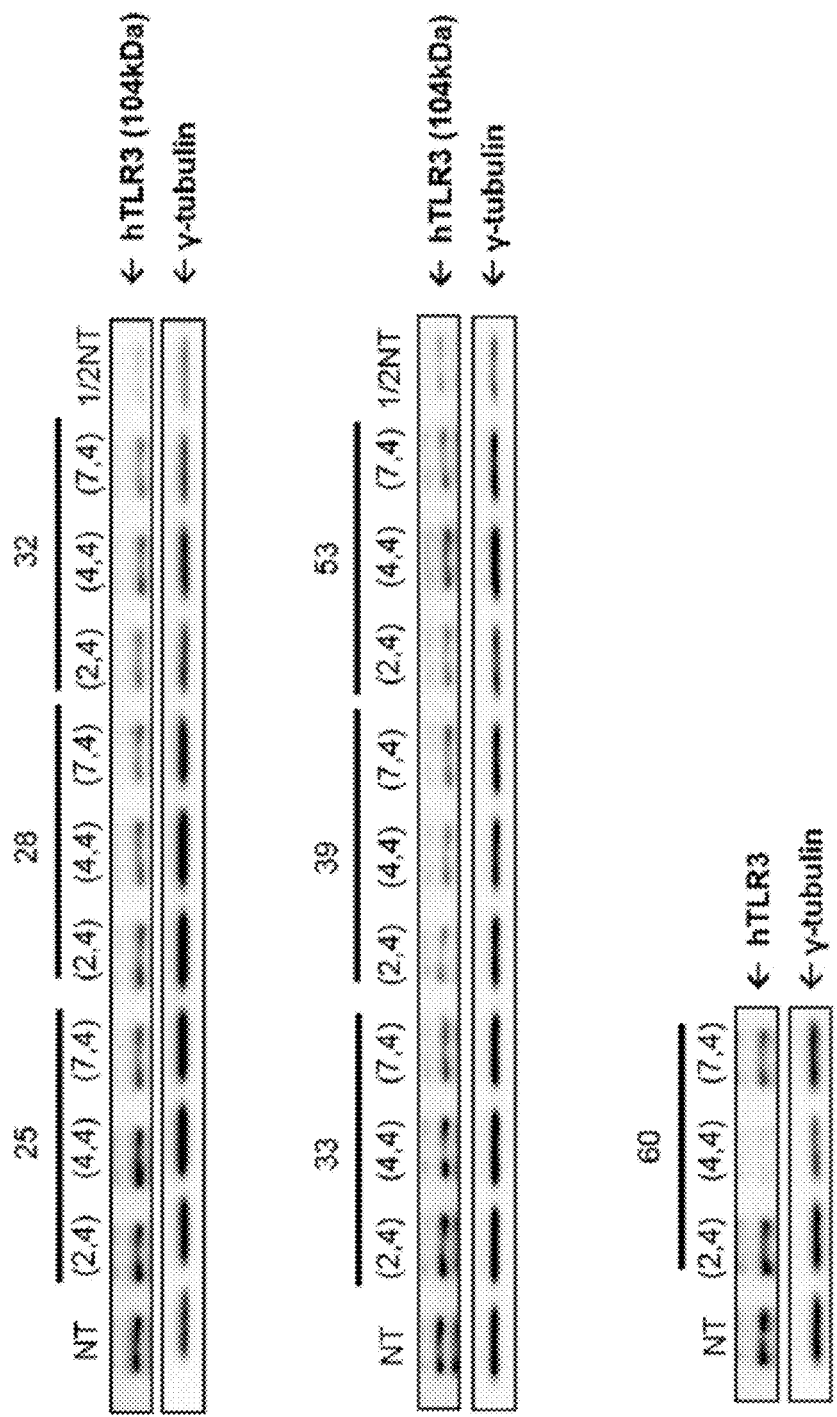
FIG. 18 shows the inhibition of TLR3 protein expression by exemplary cp-asiRNAs. The indicated cp-asiRNAs were contacted to HaCaT cells without transfection vehicle and, after 48 hours, protein was extracted and a western blot performed. (NT=no treatment).

The levels of TLR3 inhibition by each of the 24 potential cp-asiRNAs is provided in FIGS. 17 and 18 From among the potential cp-asiRNAs tested, cp-asiTLR3 39 (2, 4) was selected for further study.

TABLE 9

Primer sequences.

| Name | | Sequence (5'-3') | SEQ ID NO: | size |
|---|---|---|---|---|
| Human GAPDH | Forward | GAG TCA ACG GAT TTG GTC GT | 91 | 186 |
|  | Reverse | GAC AAG CTT CCC GTT CTC AG | 92 |  |
| Human TLR3 | Forward | TGC CCC CTT TGA ACT CTT TT | 410 | 298 |
| (Toll-like receptor 3) | Reverse | AAA AAC ACC CGC CTC AAA GT | 411 |  |

Example 14: Additional TLR3 cp-asiRNA Structures

Other potential cp-asiTLR3 structure having different strand length was synthesized and tested for its ability to inhibit TLR3 expression (Table 10)

TABLE 10

Additional cp-asiRNA sequences
(m = 2'-O-Methyl RNA. * = phosphorothioate bond).

| Name | Sequence(5' to 3') | SEQ ID NO: |
|---|---|---|
| TLR3cp-asiRNA S 39 | mGAmAGmAGmGAmAUmGUmUU*mA*A*cholesterol | 412 |
| TLR3cp-asiRNA AS 39(19) | UUAAACAUUCCUCUmU*mC*G*C*A | 413 |
| TLR3cp-asiRNA AS 39(2,4) | UUAAACAUUCCUCUmUmCG*C*A*A*A | 414 |

The ability of dose dependent of each of the potential cp-asiRNAs listed in Table 10 to inhibit TLR3 expression in HaCaT cells was tested. HaCaT cells were cultured in Dulbecco's modified Eagle's medium (DMEM, Gibco) containing 10% fetal bovine serum (FBS, Gibco) and 100 units/ml Penicillin 100 μg/ml Streptomycin. The potential cp-asiRNAs listed in Table 10 were incubated at 95° C. for 2 minutes and at 37° C. for 1 hour in Opti-MEM (Gibco). Proper strand annealing of the potential cp-asiRNAs was confirmed by gel electrophoresis. On that day cp-asiRNAs treatment, $5 \times 10^4$ cells were seeded 24 well plates then cultured in the presence of the potential cp-asiRNAs in Opti-MEM for 24 hours, at which point the cp-asiRNA-containing Opti-MEM media was replaced with a serum-containing media. Twenty-four hours later, TLR3 expression levels in HaCaT cells were determined.

Figure 19:
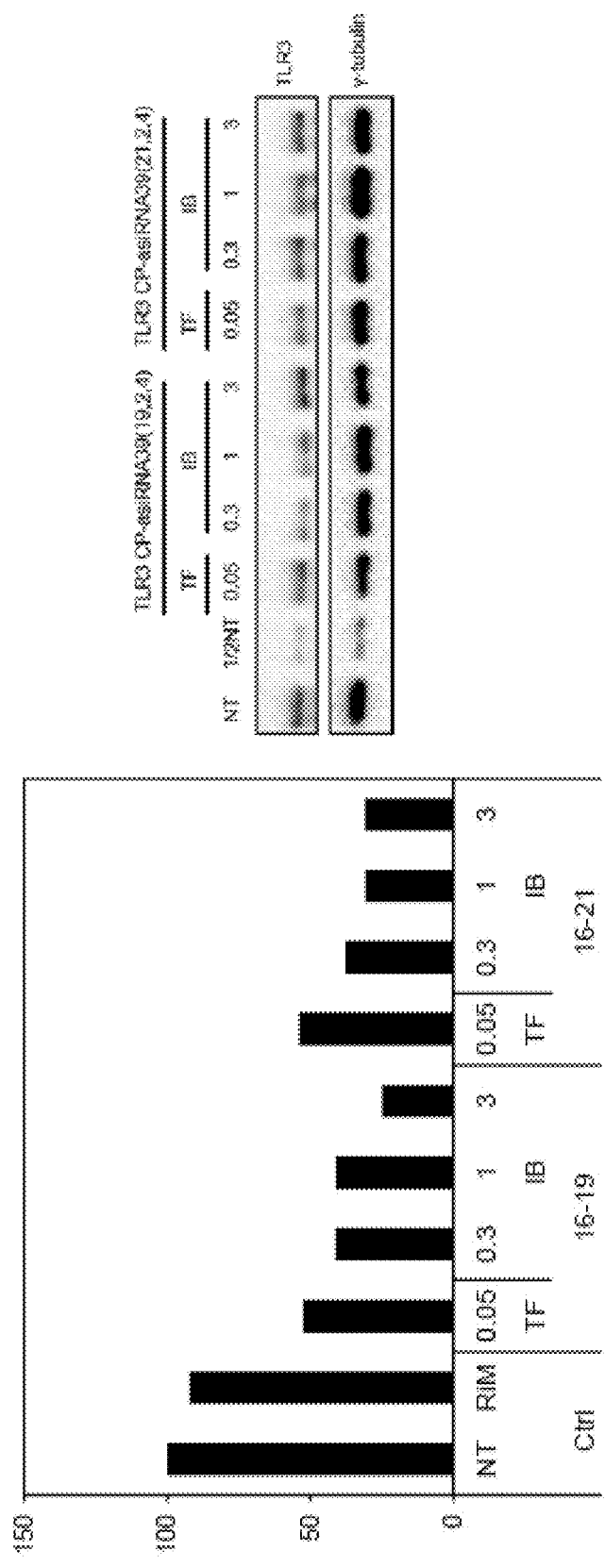
FIG. 19 shows the inhibition of TLR3 mRNA and protein expression by exemplary cp-asiRNAs. The indicated cp-asiRNAs were contacted to HaCaT cells without transfection vehicle and, after 48 hours, the degree of TLR3 expression was determined using qRT-PCR and Western blot.

As seen the FIG. 19, TLR3 expression potential cp-asiRNAs consist of 21 nucleotide antisense strands and potential cp-asiRNAs consist of 19 nucleotide antisense strands exhibited the similar levels of TLR3 inhibition. The cp-asiTLR3 (39) 21 and cp-asiTLR3 (39) 19 were selected for future experimentation.

The efficacy of cp-asiTLR3 (39) 21 and cp-asiTLR3 (39) 19 in low concentration on the production TLR3 protein was tested. The cp-asiRNAs were incubated at 95° C. for 2 minutes and at 37° C. for 1 hour in Opti-MEM (Gibco). Proper strand annealing of the potential cp-asiRNAs was confirmed by gel electrophoresis. HaCaT cells were cultured in Dulbecco's modified Eagle's medium (DMEM, Gibco) containing 10% fetal bovine serum (FBS, Gibco) and 100 units/ml Penicillin and 100 ug/ml Streptomycin. On the day of treatment, $5 \times 10^4$ HaCaT cells were seeded in 12-well plates then cultured in the presence of the potential cp-asiRNAs in Opti-MEM.

Twenty-four hours later, TLR3 protein levels in HaCaT were determined via western blot. Briefly, the treated HaCaT cells were lysed with Mammalian protein Extraction Buffer (GE Healthcare). 10 ug of the total protein extract were loaded onto an 8% SDS-PAGE gel and electrophoresed at 120 V. After electrophoresis, the proteins were transferred to PVDF membrane (Bio-rad) already activated by methanol (Merck) for 1 hour at 300 mA. The membrane was blocked for 1 hour at the room temperature with 5% skim milk (Seoul Milk) and then incubated overnight at 4° C. in 5% skim milk containing anti-TLR3 antibody (Abcam) and anti-γ-tubulin antibody (Bethyl). The membrane was then washed with TBST for 10 minutes three times and was incubated for 1 hour at the room temperature in 5% skim milk with HRP-conjugated secondary antibody (Santa Cruz). The membrane was washed with TBST for 10 minutes and treated with ECL substrate (Thermo scientific). The Target protein bands were then imaged using a Chemidoc instrument (Bio-rad).

Figure 20:
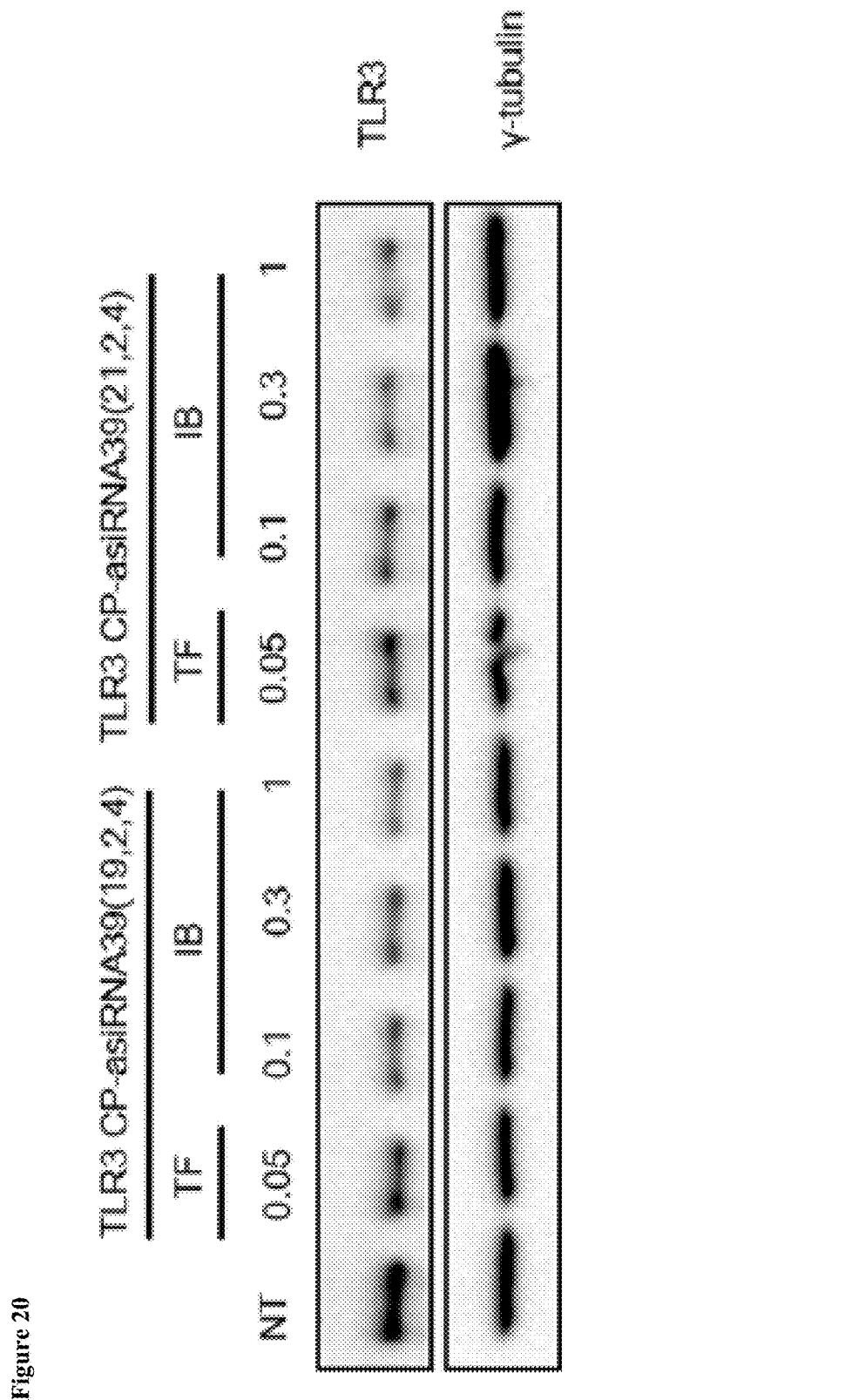
FIG. 20 shows the inhibition of TLR3 protein expression by exemplary cp-asiRNAs. The indicated cp-asiRNAs were contacted to HaCaT cells without transfection vehicle and, after 48 hours, protein was extracted and a western blot performed. (NT=no treatment).

As seen in FIG. 20, TLR3 expression potential cp-asiRNAs having 21 nucleotide antisense strands and potential cp-asiRNAs having 19 nucleotide antisense strands exhibited the similar levels of TLR3 inhibition in low concentration.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An RNA duplex of an antisense strand of at least 19 nucleotides (nt) in length and a sense strand of 16 nt in length, wherein:
   the sequence of the antisense strand comprises SEQ ID NO: 54 or SEQ ID NO: 56;
   the sequence of the sense strand is SEQ ID NO: 53 or SEQ ID NO: 55;
   a cholesterol moiety is attached to the 3' end of the sense strand; and
   the antisense strand and the sense strand form a complex in which the 5' end of the antisense strand and the 3' end of the sense strand form a blunt end.

2. The RNA duplex of claim 1, wherein the antisense strand is 19 to 21 nt in length.

3. The RNA duplex of claim 1, wherein the antisense strand is 24 to 121 nt in length.

4. The RNA duplex of claim 1, wherein the RNA duplex is capable of inhibiting MyD88 expression by a cell.

5. The RNA duplex of claim 1, wherein the RNA duplex further comprises a 2'-O-methylated nucleoside or a phosphorothioate bond.

6. The RNA duplex of claim 5, wherein the RNA duplex comprises a 2'-O-methylated nucleoside positioned at the 3' end of the sense strand or at the 3' end of the antisense strand.

7. The RNA duplex of claim 5, wherein the RNA duplex comprises a phosphorothioate bond.

8. The RNA duplex of claim 5, wherein the RNA duplex is capable of penetrating the cellular membrane of a cell in the absence of a delivery vehicle.

9. A method of inhibiting MyD88 expression by a cell, comprising contacting the cell with an RNA duplex of claim 1.

10. A pharmaceutical composition comprising an RNA duplex of claim 1 and a pharmaceutically acceptable carrier.

11. The RNA duplex of claim 1, wherein the sequence of the antisense strand is SEQ ID NO: 54 or SEQ ID NO: 95, and sequence of the sense strand is SEQ ID NO: 53.

12. The RNA duplex of claim 1, wherein the sequence of the antisense strand is SEQ ID NO: 56 or SEQ ID NO: 98, and the sequence of the sense strand is SEQ ID NO: 55.

13. The RNA duplex of claim 2, wherein the RNA duplex comprises a 2'-O-methylated nucleoside positioned at the 3' end of the sense strand or at the 3' end of the antisense strand.

14. The RNA duplex of claim 2, wherein the RNA duplex comprises a phosphorothioate bond.

15. The RNA duplex of claim 2, wherein the RNA duplex is capable of penetrating the cellular membrane of a cell in the absence of a delivery vehicle.

16. The RNA duplex of claim 2, wherein the RNA duplex is capable of inhibiting MyD88 expression by a cell.

17. The RNA duplex of claim 3, wherein the RNA duplex comprises a 2'-O-methylated nucleoside positioned at the 3' end of the sense strand or at the 3' end of the antisense strand.

18. The RNA duplex of claim 3, wherein the RNA duplex comprises a phosphorothioate bond.

19. The RNA duplex of claim 11, wherein the RNA duplex further comprises a 2'-O-methylated nucleoside or a phosphorothioate bond.

20. The RNA duplex of claim 12, wherein the RNA duplex further comprises a 2'-O-methylated nucleoside or a phosphorothioate bond.

* * * * *